United States Patent
Cui et al.

(10) Patent No.: US 11,654,144 B2
(45) Date of Patent: May 23, 2023

(54) CRYSTALLINE FORMS OF 5-BROMO-2,6-DI(1H-PYRAZOL-1-YL)PYRIMIDIN-4-AMINE AND NEW SALTS

(71) Applicants: Novartis AG, Basel (CH); Palobiofarma S.L., Barcelona (ES)

(72) Inventors: Kai Cui, Jiangsu (CN); Julio Cesar Castro-Palomino Laria, Barcelona (ES); Weiyong Kong, Jiangsu (CN)

(73) Assignees: Novartis AG, Basel (CH); Palobiofarma S.L., Barcelona (ES)

( * ) Notice: Subject to any disclaimer, the term of this patent is extended or adjusted under 35 U.S.C. 154(b) by 198 days.

(21) Appl. No.: 17/156,785

(22) Filed: Jan. 25, 2021

(65) Prior Publication Data

US 2021/0145831 A1 May 20, 2021

Related U.S. Application Data

(63) Continuation of application No. 16/616,844, filed as application No. PCT/IB2018/053839 on May 30, 2018, now Pat. No. 10,933,064.

(30) Foreign Application Priority Data

May 31, 2017 (CN) ................. PCT/CN2017/086624

(51) Int. Cl.
| | |
|---|---|
| A61K 31/506 | (2006.01) |
| A61K 39/395 | (2006.01) |
| A61K 45/06 | (2006.01) |
| C07D 403/14 | (2006.01) |
| C07K 16/28 | (2006.01) |
| A61K 39/00 | (2006.01) |

(52) U.S. Cl.
CPC ........ *A61K 31/506* (2013.01); *A61K 39/3955* (2013.01); *A61K 45/06* (2013.01); *C07D 403/14* (2013.01); *C07K 16/2818* (2013.01); *C07K 16/2827* (2013.01); *A61K 2039/545* (2013.01); *C07B 2200/13* (2013.01); *C07K 2317/565* (2013.01)

(58) Field of Classification Search
CPC ... C07D 403/14; C07D 233/88; A61K 31/506
See application file for complete search history.

(56) References Cited

U.S. PATENT DOCUMENTS

| | | | | |
|---|---|---|---|---|
| 8,168,179 | B2 | 5/2012 | Honjo et al. | |
| 8,796,284 | B2 | 8/2014 | Camacho Gomez | |
| 10,561,653 | B2 * | 2/2020 | Bilic | A61K 39/3955 |
| 10,933,064 | B2 * | 3/2021 | Cui | C07K 16/2818 |
| 11,078,191 | B2 * | 8/2021 | Bilic | A61K 45/06 |

FOREIGN PATENT DOCUMENTS

| | | |
|---|---|---|
| WO | 2005/058883 | 6/2005 |
| WO | 2008/110891 | 9/2008 |
| WO | 2008/116186 | 9/2008 |
| WO | 2011/121418 | 10/2011 |
| WO | 2017/025918 | 2/2017 |

OTHER PUBLICATIONS

Caira M R, "Crystalline Polymorphism of Organic Compounds", Topics in Current Chemistry, Springer, Berlin DE, vol. 198, ISSN 0340-1022, pp. 163-208, 1998.
PubChem CID 53466958 https://pubchem.ncbi.nlm.nih.gov/compund/5-Bromo-2_6-di_1H-pyrazol-1-yl-pyrimidin-4-amine) disclosed 5-bromo-2,6-di(1H-pyrazol-1-yl)pyrimidin-4-amine, Jan. 8, 2022.
Brittain, Harry G. "Polymorphism in Pharmaceutical Solids", Drugs and the Pharmaceutical Sciences, vol. 192, Second Edition, pp. 333-338, 2009.
PCT International Search and Preliminary Examination Guidelines of 2004 (Year 2004).
Shook et al. (ACS Chemical Neuroscience vol. 2 p. 555-567 published 2011) Year 2011.
Byrn, Stephen et al., "Pharmaceutical Solids: A Strategic Approach to Regulatory Considerations", Pharmaceutical Research, vol. 12, No. 7, pp. 945-954, 1995.
Berge et al. "Pharmaceutical Salts" Journal of Pharmaceutical Sciences, vol. 66 No. 1, pp. 1-19, 1977.

* cited by examiner

*Primary Examiner* — Theodore R. Howell
*Assistant Examiner* — George W Kosturko
(74) *Attorney, Agent, or Firm* — Michelle Han

(57) ABSTRACT

This application relates to various crystalline forms of 5-bromo-2,6-di(1H-pyrazol-1-yl)pyrimidin-4-amine and salt thereof, as well as compositions and methods of using the same. In some embodiments the crystalline forms also contain water ("hydrates"). These materials are useful in the treatment of various diseases, including carcinomas, specifically lung cancer and more specifically non-small cell lung cancer.

25 Claims, 14 Drawing Sheets

Specification includes a Sequence Listing.

SEQUENCE LISTING

<160> NUMBER OF SEQ ID NOS: 63

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Thr Tyr Trp Met His

```
<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Ile Tyr Pro Gly Thr Gly Gly Ser Asn Phe Asp Glu Lys Phe Lys
1               5                   10                  15

Asn

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Thr Thr Gly Thr Gly Ala Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Thr Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Gly Thr Gly Gly
1               5

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
                20                  25                  30

Trp Met His Trp Val Arg Gln Ala Thr Gly Gln Gly Leu Glu Trp Met
            35                  40                  45
```

-continued

Gly Asn Ile Tyr Pro Gly Thr Gly Gly Ser Asn Phe Asp Glu Lys Phe
            50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
                100                 105                 110

Val Thr Val Ser Ser
        115

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaggtgcagc tggtgcagtc aggcgccgaa gtgaagaagc ccggcgagtc actgagaatt     60
agctgtaaag gttcaggcta caccttcact acctactgga tgcactgggt ccgccaggct    120
accggtcaag gcctcgagtg gatgggtaat atctaccccg gcaccggcgg ctctaacttc    180
gacgagaagt ttaagaatag agtgactatc accgccgata agtctactag caccgcctat    240
atggaactgt ctagcctgag atcagaggac accgccgtct actactgcac taggtggact    300
accggcacag gcgcctactg gggtcaaggc actaccgtga ccgtgtctag c             351

<210> SEQ ID NO 8
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Thr Tyr
                20                  25                  30

Trp Met His Trp Val Arg Gln Ala Thr Gly Gln Gly Leu Glu Trp Met
            35                  40                  45

Gly Asn Ile Tyr Pro Gly Thr Gly Gly Ser Asn Phe Asp Glu Lys Phe
        50                  55                  60

Lys Asn Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 9
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata gtctactagc accgcctat     240 atggaactgt ctagcctgag atcagaggac accgccgtct actactgcac taggtggact     300
accggcacag cgcctactg gggtcaaggc actaccgtga ccgtgtctag cgctagcact     360
aagggcccgt ccgtgttccc cctggcacct tgtagccgga gcactagcga atccaccgct     420

```
gccctcggct gcctggtcaa ggattacttc ccggagcccg tgaccgtgtc ctggaacagc    480
ggagccctga cctccggagt gcacaccttc cccgctgtgc tgcagagctc cgggctgtac    540
tcgctgtcgt cggtggtcac ggtgccttca tctagcctgg gtaccaagac ctacacttgc    600
aacgtggacc acaagccttc caacactaag gtggacaagc gcgtcgaatc gaagtacggc    660
ccaccgtgcc cgccttgtcc cgcgccggag ttcctcggcg tccctcggt ctttctgttc    720 ccaccgaagc ccaaggacac tttgatgatt cccgcaccc ctgaagtgac atgcgtggtc    780
gtggacgtgt cacaggaaga tccggaggtg cagttcaatt ggtacgtgga tggcgtcgag    840
gtgcacaacg ccaaaaccaa gccgagggag gagcagttca actccactta ccgcgtcgtg    900
tccgtgctga cggtgctgca tcaggactgg ctgaacggga aggagtacaa gtgcaaagtg    960
tccaacaagg gacttcctag ctcaatcgaa aagaccatct cgaaagccaa gggacagccc   1020
cgggaacccc aagtgtatac cctgccaccg agccaggaag aaatgactaa gaaccaagtc   1080
tcattgactt gccttgtgaa gggcttctac ccatcggata tcgccgtgga atgggagtcc   1140
aacggccagc cggaaaacaa ctacaagacc acccctccgg tgctggactc agacggatcc   1200
ttcttcctct actcgcggct gaccgtggat aagagcagat ggcaggaggg aaatgtgttc   1260
agctgttctg tgatgcatga agccctgcac aaccactaca ctcagaagtc cctgtccctc   1320
tccctggga                                                          1329
```

```
<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ser Ser Gln Ser Leu Leu Asp Ser Gly Asn Gln Lys Asn Phe Leu
1               5                   10                  15

Thr

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asn Asp Tyr Ser Tyr Pro Tyr Thr
1               5

<210> SEQ ID NO 13
```

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Ser Leu Leu Asp Ser Gly Asn Gln Lys Asn Phe
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ala Ser
1

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Tyr Ser Tyr Pro Tyr
1               5

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 17
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gagatcgtcc tgactcagtc acccgctacc ctgagcctga gccctggcga gcgggctaca    60
ctgagctgta atctagtca gtcactgctg gatagcggta atcagaagaa cttcctgacc    120
tggtatcagc agaagcccgg taaagcccct aagctgctga tctactgggc ctctactaga   180
gaatcaggcg tgccctctag gtttagcggt agcggtagtg gcaccgactt caccttcact   240
atctctagcc tgcagcccga ggatatcgct acctactact gtcagaacga ctatagctac   300
ccctacacct tcggtcaagg cactaaggtc gagattaag                          339

<210> SEQ ID NO 18
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 19
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300
ccctacacct tcggtcaagg cactaaggtc gagattaagc gtacggtggc cgctcccagc     360
gtgttcatct ccccccccag cgacgagcag ctgaagagcg gcaccgccag cgtggtgtgc     420
ctgctgaaca acttctaccc ccgggaggcc aaggtgcagt ggaaggtgga caacgccctg     480
cagagcggca acagccagga gagcgtcacc gagcaggaca gcaaggactc cacctacagc     540
ctgagcagca ccctgaccct gagcaaggcc gactacgaga agcataaggt gtacgcctgc     600
gaggtgaccc accagggcct gtccagcccc gtgaccaaga gcttcaacag gggcgagtgc     660
```

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 21
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg tcaagcccct agactgctga tctactgggc ctctactaga     180
gaatcaggcg tgccctctag gtttagcggt agcggtagtg gcaccgactt caccttcact     240
atctctagcc tggaagccga ggacgccgct acctactact gtcagaacga ctatagctac     300
```

```
cccctacacct tcggtcaagg cactaaggtc gagattaag                                339
```

<210> SEQ ID NO 22
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys Lys Ser Gln Ser Leu Leu Asp Ser
            20                  25                  30

Gly Asn Gln Lys Asn Phe Leu Thr Trp Tyr Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 23
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gagatcgtcc tgactcagtc acccgctacc ctgagcctga gccctggcga gcgggctaca        60
ctgagctgta aatctagtca gtcactgctg gatagcggta atcagaagaa cttcctgacc       120
tggtatcagc agaagcccgg tcaagcccct agactgctga tctactgggc ctctactaga       180
gaatcaggcg tgccctctag gtttagcggt agcggtagtg gcaccgactt caccttcact       240
atctctagcc tggaagccga ggacgccgct acctactact gtcagaacga ctatagctac       300
ccctacacct tcggtcaagg cactaaggtc gagattaagc gtacggtggc cgctcccagc       360
```

```
gtgttcatct tccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca acagccagga gagcgtcacc gagcaggaca gcaaggactc cacctacagc    540
ctgagcagca ccctgaccct gagcaaggcc gactacgaga gcataaggt gtacgcctgc    600 gaggtgaccc accagggcct gtccagcccc gtgaccaaga gcttcaacag gggcgagtgc    660
```

```
<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acctactgga tgcac                                                     15

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aatatctacc ccggcaccgg cggctctaac ttcgacgaga gtttaagaa t               51

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tggactaccg gcacaggcgc ctac                                           24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggctacacct tcactaccta c                                              21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taccccggca ccggcggc                                                  18

<210> SEQ ID NO 29
<211> LENGTH: 51
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 29
aaatctagtc agtcactgct ggatagcggt aatcagaaga acttcctgac c              51

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgggcctcta ctagagaatc a                                              21

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagaacgact atagctaccc ctacacc                                        27

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agtcagtcac tgctggatag cggtaatcag aagaacttc                           39

<210> SEQ ID NO 33
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 tgggcctct                                                             9

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gactatagct acccctac                                                  18

<210> SEQ ID NO 35
<211> LENGTH: 440
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 35

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
```

```
                        385                 390                 395                 400
Ser Arg Leu Thr Val Asp Lys Ser Arg Trp Gln Glu Gly Asn Val Phe
                    405                 410                 415

Ser Cys Ser Val Met His Glu Ala Leu His Asn His Tyr Thr Gln Lys
                420                 425                 430

Ser Leu Ser Leu Ser Leu Gly Lys
            435                 440

<210> SEQ ID NO 36
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
```

-continued

```
                    20                  25                  30
Tyr Met Tyr Trp Val Arg Gln Ala Pro Gly Gln Gly Leu Glu Trp Met
                35                  40                  45
Gly Gly Ile Asn Pro Ser Asn Gly Thr Asn Phe Asn Glu Lys Phe
        50                  55                  60
Lys Asn Arg Val Thr Leu Thr Thr Asp Ser Thr Thr Thr Ala Tyr
65                  70                  75                  80
Met Glu Leu Lys Ser Leu Gln Phe Asp Thr Ala Val Tyr Tyr Cys
                85                  90                  95
Ala Arg Arg Asp Tyr Arg Phe Asp Met Gly Phe Asp Tyr Trp Gly Gln
                100                 105                 110
Gly Thr Thr Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
            435                 440                 445
```

```
<210> SEQ ID NO 38
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 39
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80
```

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 40
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 40

Glu Ile Val Leu Thr Gln Ser Pro Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Tyr Thr Phe Thr Thr Tyr Trp Met His
1               5                   10

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Lys Gly
```

```
                    50                  55                  60
Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                     85                  90                  95

Ile Lys Leu Gly Thr Val Thr Val Asp Tyr Trp Gly Gln Gly Thr
                100                 105                 110

Leu Val Thr Val Ser Ser
            115

<210> SEQ ID NO 43
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                     85                  90                  95

Ser Thr Arg Val Phe Gly Thr Gly Thr Lys Val Thr Val Leu
                100                 105                 110

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Tyr Trp Met Tyr
  1               5

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ile Asp Pro Asn Ser Gly Ser Thr Lys Tyr Asn Glu Lys Phe Lys
  1               5                  10                  15

Asn

<210> SEQ ID NO 46
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Tyr Arg Lys Gly Leu Tyr Ala Met Asp Tyr
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Tyr Thr Phe Thr Ser Tyr
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Pro Asn Ser Gly Ser
1               5

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ala Ser Gln Asp Val Gly Thr Ala Val Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Ala Ser Thr Arg His Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Asn Ser Tyr Pro Leu Thr
```

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Gln Asp Val Gly Thr Ala
1               5

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Ala Ser
1

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Asn Ser Tyr Pro Leu
1               5

<210> SEQ ID NO 55
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
                100                 105                 110

Gly Thr Thr Val Thr Val Ser Ser
        115                 120

<210> SEQ ID NO 56
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
gaggtccagc tggtacagtc tggggctgag gtgaagaagc ctggggctac agtgaaaatc    60
tcctgcaagg tttctggcta caccttcacc agttactgga tgtactgggt gcgacaggct   120
cgtggacaac gccttgagtg gataggtagg attgatccta atagtgggag tactaagtac   180
aatgagaagt tcaagaacag attcaccatc tccagagaca attccaagaa cacgctgtat   240
cttcaaatga acagcctgag agccgaggac acggccgtgt attactgtgc aagggactat   300
agaaaggggc tctatgctat ggactactgg ggccagggca ccaccgtgac cgtgtcctcc   360
```

<210> SEQ ID NO 57
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gaggtccagc tggtacagtc tggggctgag gtgaagaagc ctggggctac agtgaaaatc    60
tcctgcaagg tttctggcta caccttcacc agttactgga tgtactgggt gcgacaggct   120
cgtggacaac gccttgagtg gataggtagg attgatccta atagtgggag tactaagtac   180
aatgagaagt tcaagaacag attcaccatc tccagagaca attccaagaa cacgctgtat   240
cttcaaatga acagcctgag agccgaggac acggccgtgt attactgtgc aagggactat   300
agaaaggggc tctatgctat ggactactgg ggccagggca ccaccgtgac cgtgtcctcc   360
gcttccacca agggcccatc cgtcttcccc ctggcgccct gctccaggag cacctccgag   420
agcacagccg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacgaagacc   600
tacacctgca acgtagatca caagcccagc aacaccaagg tggacaagag agttgagtcc   660
aaatatggtc cccatgccc accgtgccca gcacctgagt tcctgggggg accatcagtc   720
ttcctgttcc ccccaaaacc caaggacact ctcatgatct cccggacccc tgaggtcacg   780
tgcgtggtgg tggacgtgag ccaggaagac cccgaggtcc agttcaactg gtacgtggat   840
ggcgtggagg tgcataatgc caagacaaag ccgcgggagg agcagttcaa cagcacgtac   900
cgtgtggtca gcgtcctcac cgtcctgcac caggactggc tgaacggcaa ggagtacaag   960
tgcaaggtgt ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggcta accgtggaca agagcaggtg gcaggagggg  1260
aatgtcttct catgctccgt gatgcatgag gctctgcaca accactacac acagaagagc  1320
ctctccctgt ctctgggtaa a                                             1341
```

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcacctttα ccatcagtag cctggaagct     240
gaagatgctg caacatatta ctgtcagcag tataacagct atcctctcac gttcggccaa     300
gggaccaagg tggaaatcaa a                                               321

<210> SEQ ID NO 60
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Gln Tyr Asn Ser Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcaccttta ccatcagtag cctggaagct     240
gaagatgctg caacatatta ctgtcagcag tataacagct atcctctcac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 62
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

-continued

Trp Met Tyr Trp Val Arg Gln Ala Arg Gly Gln Arg Leu Glu Trp Ile
         35                  40                  45

Gly Arg Ile Asp Pro Asn Ser Gly Ser Thr Lys Tyr Asn Glu Lys Phe
         50                  55                  60

Lys Asn Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Arg Asp Tyr Arg Lys Gly Leu Tyr Ala Met Asp Tyr Trp Gly Gln
                 100                 105                 110

Gly Thr Thr Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
         180                 185                 190

Ser Ser Ser Leu Gly Thr Lys Thr Tyr Thr Cys Asn Val Asp His Lys
         195                 200                 205

Pro Ser Asn Thr Lys Val Asp Lys Arg Val Glu Ser Lys Tyr Gly Pro
         210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser Gln Glu Asp Pro Glu
         260                 265                 270

Val Gln Phe Asn Trp Tyr Val Asp Gly Val Glu Val His Asn Ala Lys
         275                 280                 285

Thr Lys Pro Arg Glu Glu Gln Phe Asn Ser Thr Tyr Arg Val Val Ser
         290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                 325                 330                 335

Ser Lys Ala Lys Gly Gln Pro Arg Glu Pro Gln Val Tyr Thr Leu Pro
                 340                 345                 350

Pro Ser Gln Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                 405                 410                 415

Trp Gln Glu Gly Asn Val Phe Ser Cys Ser Val Met His Glu Ala Leu
                 420                 425                 430

His Asn His Tyr Thr Gln Lys Ser Leu Ser Leu Ser Leu Gly Lys
         435                 440                 445

```
<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Tyr Thr Phe Thr Ser Tyr Trp Met Tyr
1               5                   10
```

CRYSTALLINE FORMS OF 5-BROMO-2,6-DI(1H-PYRAZOL-1-YL)PYRIMIDIN-4-AMINE AND NEW SALTS

FIELD OF INVENTION

The present disclosure generally relates to crystalline forms of 5-bromo-2,6-di(1H-pyrazol-1-yl)pyrimidin-4-amine and new salts. The present disclosure also generally relates to a pharmaceutical composition comprising the crystalline forms, as well of methods of using the crystalline forms in the treatment of particular cancers, and methods for obtaining such crystalline forms.

BACKGROUND 5-bromo-2,6-di(1H-pyrazol-1-yl)pyrimidin-4-amine was first disclosed in WO2011/121418, filed Mar. 29, 2011, which is incorporated by reference in its entirety, and is an Adenosine 2a receptor inhibitor having the structure of Formula I:

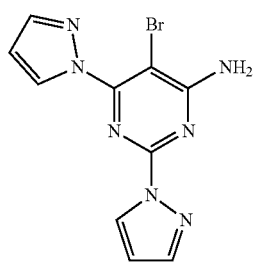

Formula I

The compound of Formula I is useful in the treatment of various disease states associated with the inhibition of the activity of Adenosine A2a receptor. As such, the compound of Formula I is therefore useful in the treatment of certain cancers, including, for example, a lung cancer, a melanoma, a renal cancer, a liver cancer, a myeloma, a prostate cancer, a breast cancer, a colorectal cancer, a pancreatic cancer, a head and neck cancer, anal cancer, gastro-esophageal cancer, thyroid cancer, cervical cancer, a lymphoproliferative disease or a hematological cancer, T-cell lymphoma, B-cell lymphoma, a non-Hogdkin lymphoma, or a leukemia. Additionally, Compound of Formula I is also useful in the treatment of neurodegenerative diseases such as Parkinson's disease, Huntington's or Alzheimer diseases, neuropsychiatric disorders and dysfunctions such as depression, excessive daytime sleepiness, restless legs syndrome, attention deficit hyperactivity disorder and cognitive fatigue.

It is well known that the solid state form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability. It is not yet possible to predict whether a particular compound or salt of a compound will form polymorphs, whether any such polymorphs will be suitable for commercial use in a therapeutic composition, or which polymorphs will display such desirable properties.

SUMMARY

The present disclosure provides crystalline forms of 5-bromo-2,6-di(1H-pyrazol-1-yl)pyrimidin-4-amine hydrochloride salts. In a particular embodiment, the hydrochloride salts further include water (referred to herein as hydrates). The present disclosure also provides crystalline forms of 5-bromo-2,6-di(1H-pyrazol-1-yl)pyrimidin-4-amine sulfate salt and 2 mesylate salt forms.

The present disclosure further provide two crystalline forms of 5-bromo-2,6-di(1H-pyrazol-1-yl)pyrimidin-4-amine in its free form (or non-salt form). Embodiments of these crystalline forms include those forms designated herein as Form A, Form B, Form C, Form D, Form E, Form F and Form G. The names used herein to identify a specific form, e.g. "Form A" etc., should not be considered limiting with respect to any other substance possessing similar or identical physical and chemical characteristics, but rather it should be understood that these designations are mere identifiers that should be interpreted according to the characterization information also presented herein.

Figure 1:
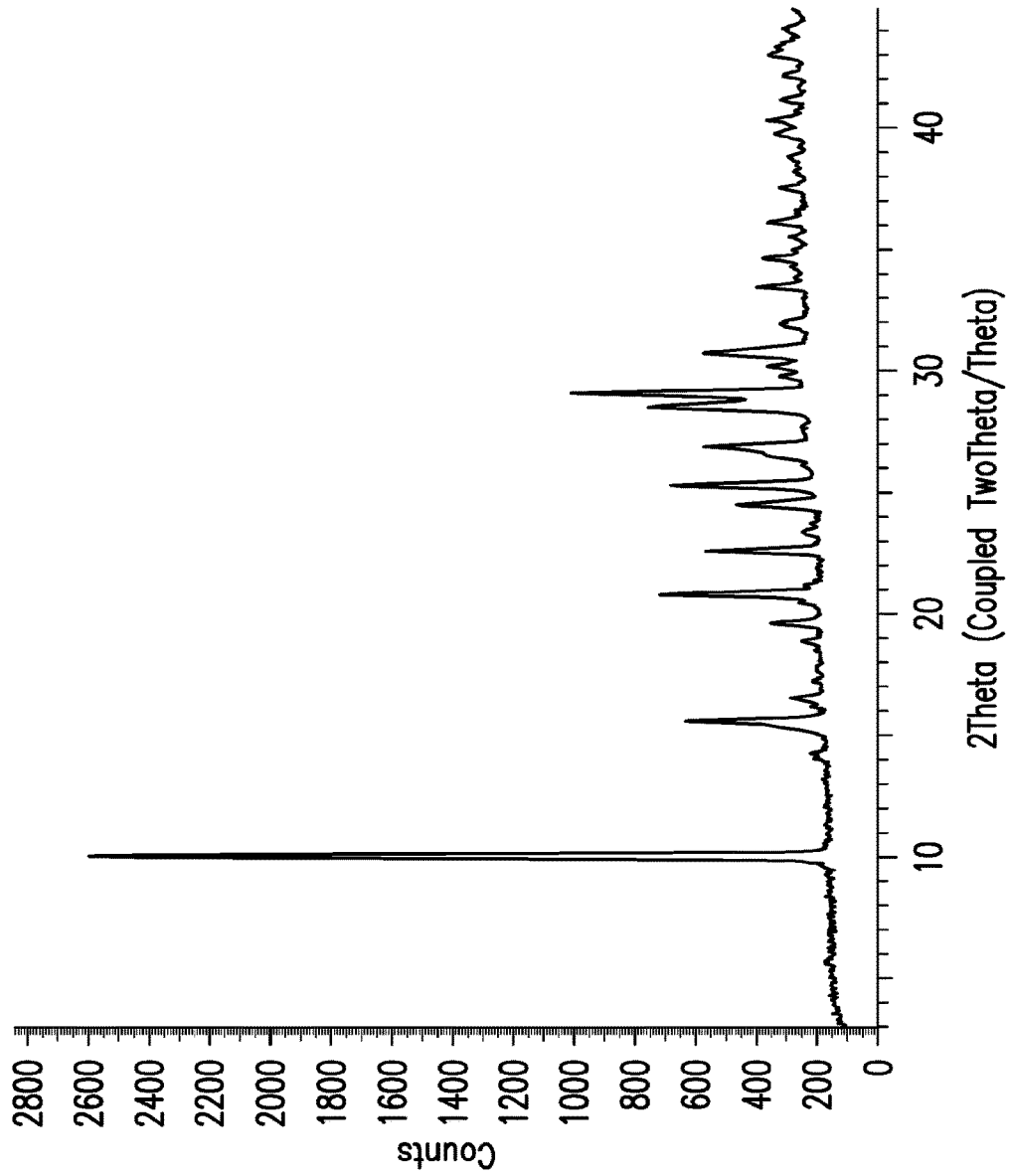
FIG. 1 provides an illustrative XRPD spectrum for the mono-hydrochloride hydrate salt of the compound of Formula I, designated herein as Form A, showing degrees 2θ (2-theta) on the X-axis and relative intensity on the Y-axis.

More detailed listings of the XRPD peaks for each of forms A through G are set forth in Tables 1 through 7, respectively below, in which the % relative intensity ($I/I_0 \times 100$) is also provided. It should be understood that in the X-ray powder diffraction spectra or pattern that there is inherent variability in the values measured in degrees 2θ (°2θ) as a result of, for example, instrumental variation (including differences between instruments). As such, it should be understood that there is a variability of up to ±0.2°2θ in XRPD peak measurements and yet such peak values would still be considered to be representative of a particular solid state form of the crystalline materials described herein. It should also be understood that other measured values from XRPD experiments and DSC/TGA experiments, such as relative intensity and water content, can vary as a result of, for example, sample preparation and/or storage and/or environmental conditions, and yet the measured values will still be considered to be representative of a particular solid state form of the crystalline materials described herein.

DETAILED DESCRIPTION OF THE DISCLOSURE

The present disclosure relates to crystalline forms of various salts of 5-bromo-2,6-di(1H-pyrazol-1-yl)pyrimidin-4-amine (the compound of Formula I), which are described and characterized herein. The present invention also relates to various crystalline forms of the free form of 5-bromo-2,6-di(1H-pyrazol-1-yl)pyrimidin-4-amine, which are described and characterized herein.

In embodiment 1, the present disclosure provides a crystalline form of the mono-hydrochloride hydrate salt of 5-bromo-2,6-di(1H-pyrazol-1-yl)pyrimidin-4-amine (Form A) having an X-ray powder diffraction (XRPD) pattern comprising a representative peak, in terms of ° 2θ, at 10.0±0.2°2θ. In another embodiment, the XRPD pattern further comprises one or more additional representative peaks chosen from 29.1±0.2°2θ, 28.5±0.2°2θ, and 20.8±0.2°2θ. Accordingly, the XRPD pattern for the crystalline form of the mono-hydrochloride hydrate salt of the compound of Formula I may comprise one, two, three, or four representative peaks above. In another embodiment, the crystalline form of the mono-hydrochloride hydrate salt of the compound of Formula I has an XRPD pattern that may further include one or more additional representative peaks chosen from 25.3±0.2°2θ and 15.6±0.2°2θ. Thus, the XRPD pattern for the crystalline form of the mono-hydrochloride hydrate salt of the compound of Formula I may comprise one, two, three, four, five or six representative peaks disclosed above or disclosed in table 1.

In another embodiment, the mono-hydrochloride hydrate form is characterized by a x-ray powder diffraction pattern comprising four or more 2θ values (CuKα λ=1.54184 Å) selected from the group consisting of 10.0±0.2°, 15.6±0.2°, 20.8±0.2°, 22.6±0.2°, 24.5±0.2°, 25.3±0.2°, 28.5±0.2°, 29.1±0.2°, 30.70.2, measured at a temperature of about 25° C. and an x-ray wavelength, λ, of 1.54184 Å.

In yet another embodiment, a crystalline form of the mono-hydrochloride hydrate salt of the compound of Formula I has an XRPD pattern substantially as shown in FIG. 1. It should be understood that the water content of Form A can be in the range of about 3.0% to about 5.0% and still be considered to be a monohydrate having the XRPD pattern comprising the one, two, three, four, five or six representative peaks described above. The water content for Form A is 4.87%.

The crystalline form of the mono-hydrochloride hydrate salt of 5-bromo-2,6-di(1H-pyrazol-1-yl)pyrimidin-4-amine may be characterized thermally. In one embodiment, a crystalline form of the mono-hydrochloride hydrate salt of the compound of Formula I has a differential thermogravimetric profile comprising an endothermic peak starting at about 78.16° C. with an enthalpy ΔH of 300.87 J/g (corresponding to the dehydration) and an endothermic peak starting at about 212.48° C. with an enthalpy ΔH of 86.83 J/g (corresponding to the melting).

Figure 2:
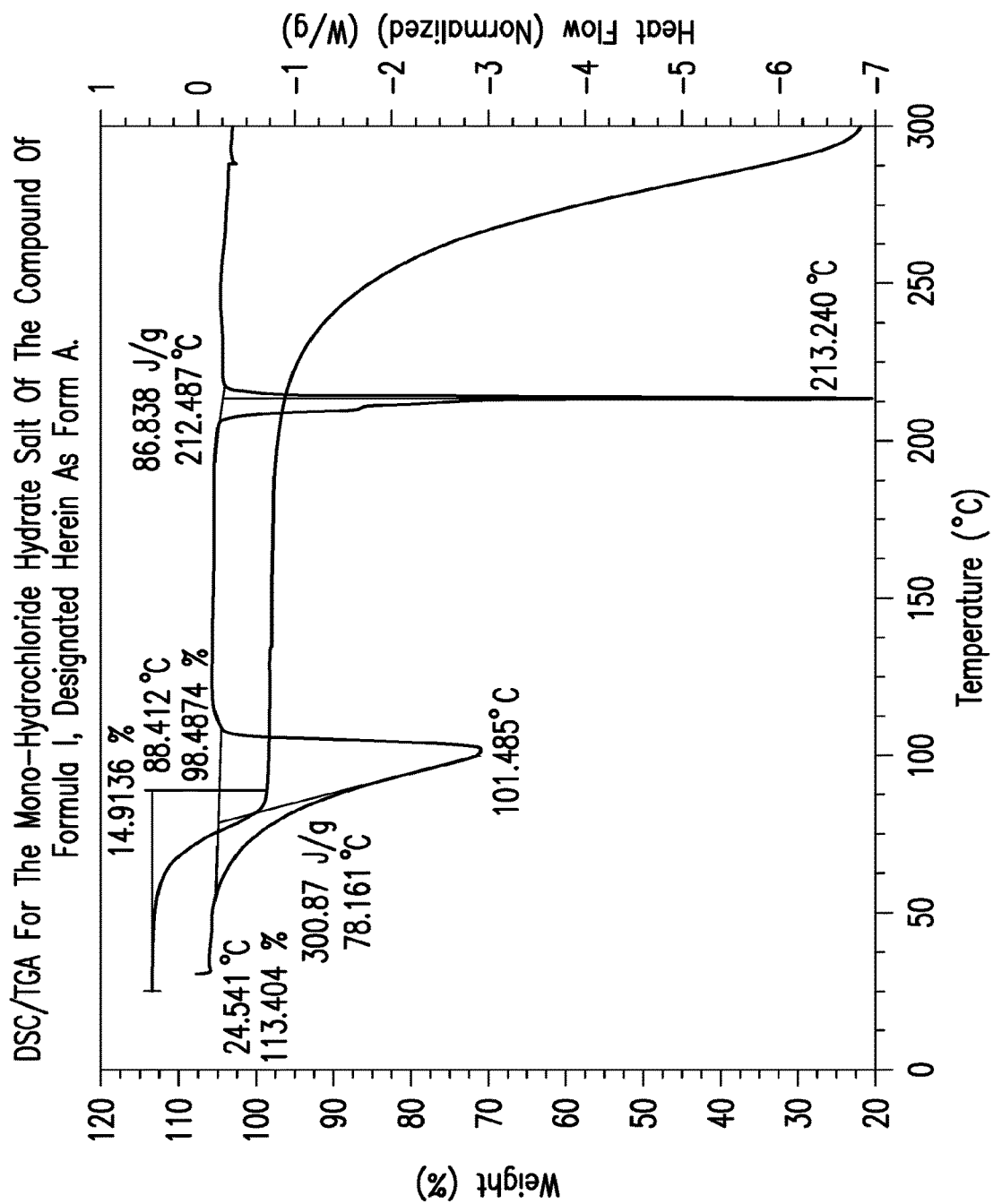
FIG. 2 provides an illustrative DSC/TGA for the mono-hydrochloride hydrate salt of the compound of Formula I, designated herein as Form A.

In another embodiment, a crystalline form of the mono-hydrochloride hydrate salt of the compound of Formula I has a DSC thermogram that is substantially as shown in FIG. 2. It should be understood that hydrated forms may yield different thermograms (in terms of peak shape and profile) depending on instrument parameters, thus the same material may have thermograms that look substantially different from each other when the data is generated on two different instruments.

In another embodiment, a crystalline form of the mono-hydrochloride hydrate salt of the compound of Formula I has a thermo gravimetric analysis (TGA) diagram substantially the same as that shown in shown in FIG. 2. The weight loss by TGA is about 14.9% at 88° C.

In yet another embodiment, the crystalline form A is substantially phase pure.

In embodiment 2, the present disclosure provides a crystalline form of the di-hydrochloride hydrate salt of 5-bromo-2,6-di(1H-pyrazol-1-yl)pyrimidin-4-amine (Form B) having an X-ray powder diffraction (XRPD) pattern comprising a representative peak, in terms of °2θ, at 26.4±0.2°2θ. In another embodiment, the XRPD pattern further comprises one or more additional representative peaks chosen from 9.6±0.2°2θ, 22.1±0.2°2θ, 28.4±0.2°2θ and 30.6±0.2°2θ. Accordingly, the XRPD pattern for the crystalline form of the di-hydrochloride hydrate salt of the compound of Formula I may comprise one, two, three, or four representative peaks above. In another embodiment, the crystalline form of the di-hydrochloride hydrate salt of the compound of Formula I has an XRPD pattern that may further include one or more additional representative peaks chosen from 22.4±0.2°2θ, 27.4±0.2°2θ and 27.9±0.2°2θ. Thus, the XRPD pattern for the crystalline form of the di-hydrochloride monohydrate salt of the compound of Formula I may comprise one, two, three, four, five or six representative peaks disclosed above or disclosed in table 2.

In another aspect of embodiment 2, the di-hydrochloride hydrate form is characterized by a x-ray powder diffraction pattern comprising four or more 2θ values (CuKα

λ=1.54184 Å) selected from the group consisting of 9.6±0.2°, 16.1±0.2°, 21.5±0.2°, 22.1±0.2°, 22.4±0.2°, 23.1±0.2°, 26.4±0.2°, 27.4±0.2°, 27.9±0.2, 28.4±0.2, 30.6±0.2 and 34.8±0.2, measured at a temperature of about 25° C. and an x-ray wavelength, λ, of 1.54184 Å.

Figure 3:
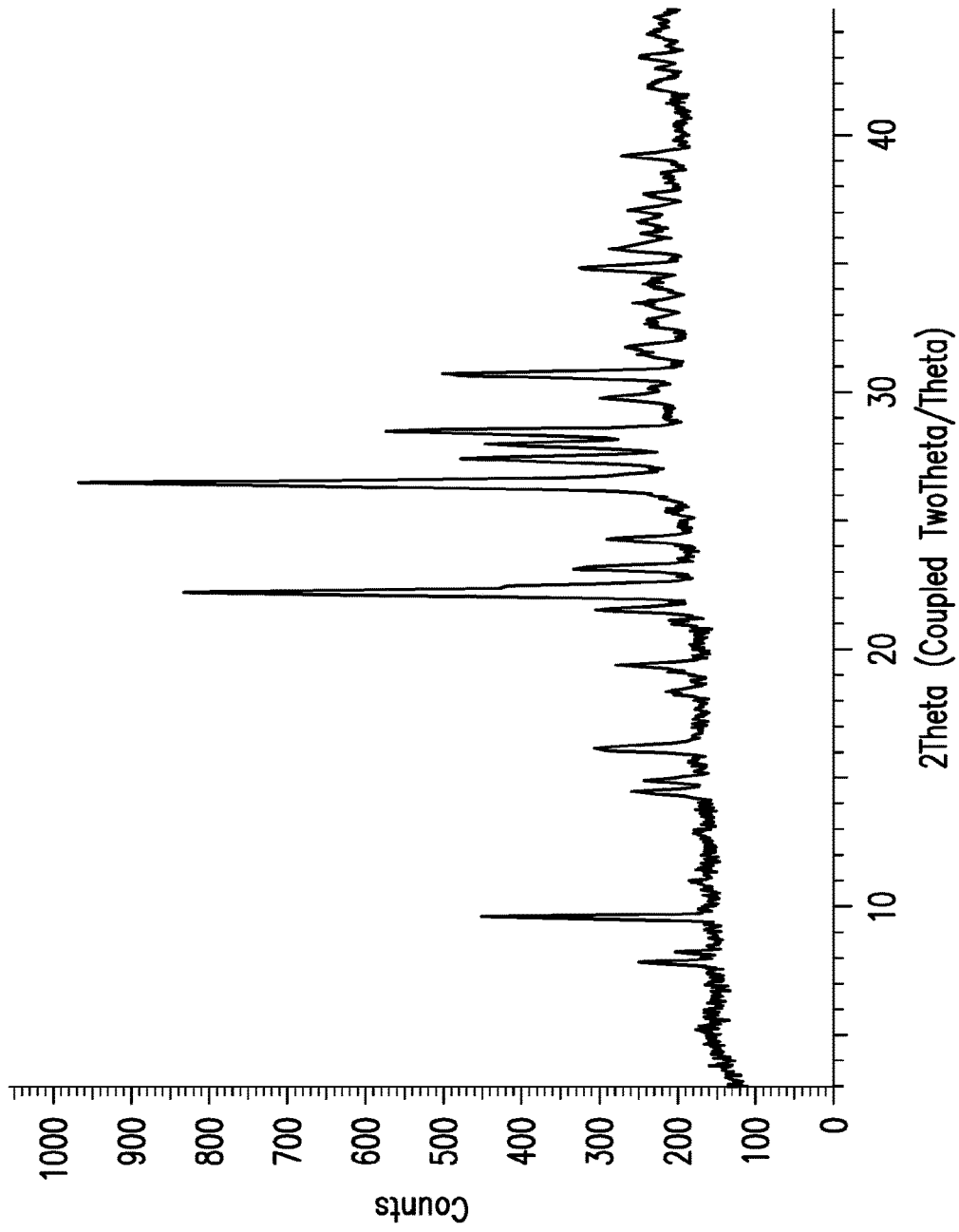
FIG. 3 provides an illustrative XRPD spectrum for the di-hydrochloride hydrate salt of the compound of Formula I, designated herein as Form B, showing degrees 2θ (2-theta) on the X-axis and relative intensity on the Y-axis.

In yet another aspect of embodiment 2, a crystalline form of the di-hydrochloride monohydrate salt of the compound of Formula I has an XRPD pattern substantially as shown in FIG. 3. It should be understood that the water content of Form B can be in the range of about 3.0% to about 5.0% and still be considered to be a monohydrate having the XRPD pattern comprising the one, two, three, four, five or six representative peaks described above. The water content for Form B is 4.5%.

The crystalline form of the di-hydrochloride hydrate salt of 5-bromo-2,6-di(1H-pyrazol-1-yl)pyrimidin-4-amine may be characterized thermally. In one embodiment, a crystalline form of the di-hydrochloride hydrate salt of the compound of Formula I has a differential thermogravimetric profile comprising an endothermic peak starting at about 78.92° C. with enthalpy ΔH of 399.81 J/g, and an endothermic peak starting at about 212.18° C. with enthalpy ΔH of 81.06 J/g.

Figure 4:
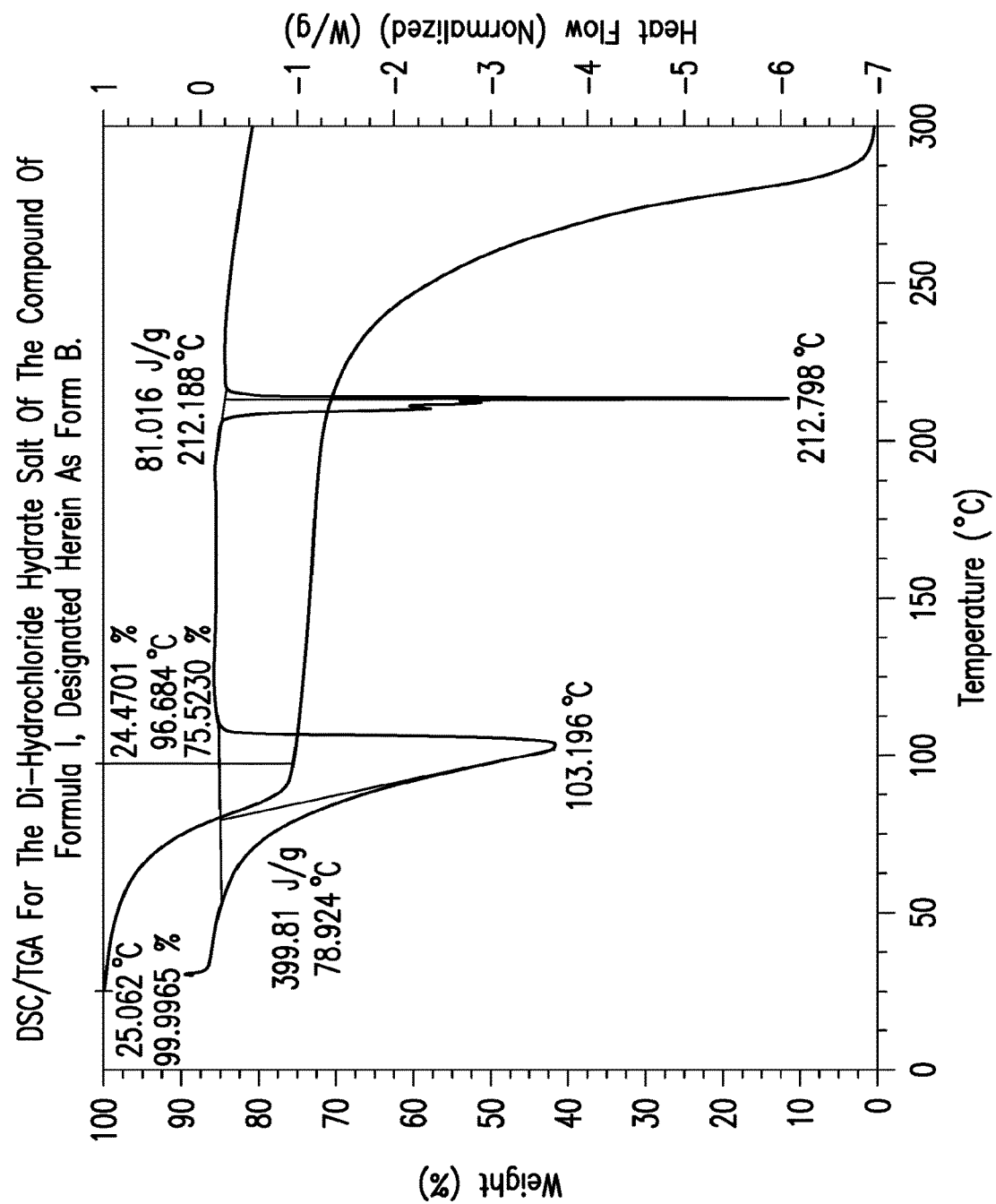
FIG. 4 provides an illustrative DSC/TGA for the di-hydrochloride hydrate salt of the compound of Formula I, designated herein as Form B.

In another aspect of embodiment 2, a crystalline form of the di-hydrochloride hydrate salt of the compound of Formula I has a DSC thermogram that is substantially as shown in FIG. 4. It should be understood that hydrated forms may yield different thermograms (in terms of peak shape and profile) depending on instrument parameters, thus the same material may have thermograms that look substantially different from each other when the data is generated on two different instruments.

In another aspect of embodiment 2, a crystalline form of the di-hydrochloride hydrate salt of the compound of Formula I has a thermo gravimetric analysis (TGA) diagram substantially the same as that shown in shown in FIG. 4. The weight loss by TGA is about 24.4% at 96° C.

In yet another embodiment, the crystalline form B is substantially phase pure.

In embodiment 3, the present disclosure provides a crystalline form of the sulfate salt of 5-bromo-2,6-di(1H-pyrazol-1-yl)pyrimidin-4-amine (Form C) having an X-ray powder diffraction (XRPD) pattern comprising a representative peak, in terms of ° 2θ, at 9.4±0.2°2θ. In another embodiment, the XRPD pattern further comprises one or more additional representative peaks chosen from 23.2±0.2°2θ, 24.8±0.2°2θ and 26.8±0.2°2θ. Accordingly, the XRPD pattern for the crystalline form of the sulfate salt of the compound of Formula I may comprise one, two, three, or four representative peaks above. In another embodiment, the crystalline form of the sulfate salt of the compound of Formula I has an XRPD pattern that may further include one or more additional representative peaks chosen from 12.3±0.2°2θ, 17.1±0.2°2θ, 26.5±0.2°2θ and 26.1±0.2°2θ. Thus, the XRPD pattern for the crystalline form of the sulfate salt of the compound of Formula I may comprise one, two, three, four, five or six representative peaks disclosed above or disclosed in table 3.

In another aspect of embodiment 3, the sulfate form is characterized by a x-ray powder diffraction pattern comprising four or more 2θ values (CuKα λ=1.54184 Å) selected from the group consisting of 9.4±0.2°, 12.3±0.2°, 12.7±0.2°, 17.1±0.2°, 23.2±0.2°, 24.8±0.2°, 26.1±0.2°, 26.4±0.2°, 26.8±0.2, and 29.9±0.2, measured at a temperature of about 25° C. and an x-ray wavelength, λ, of 1.54184 Å.

Figure 5:
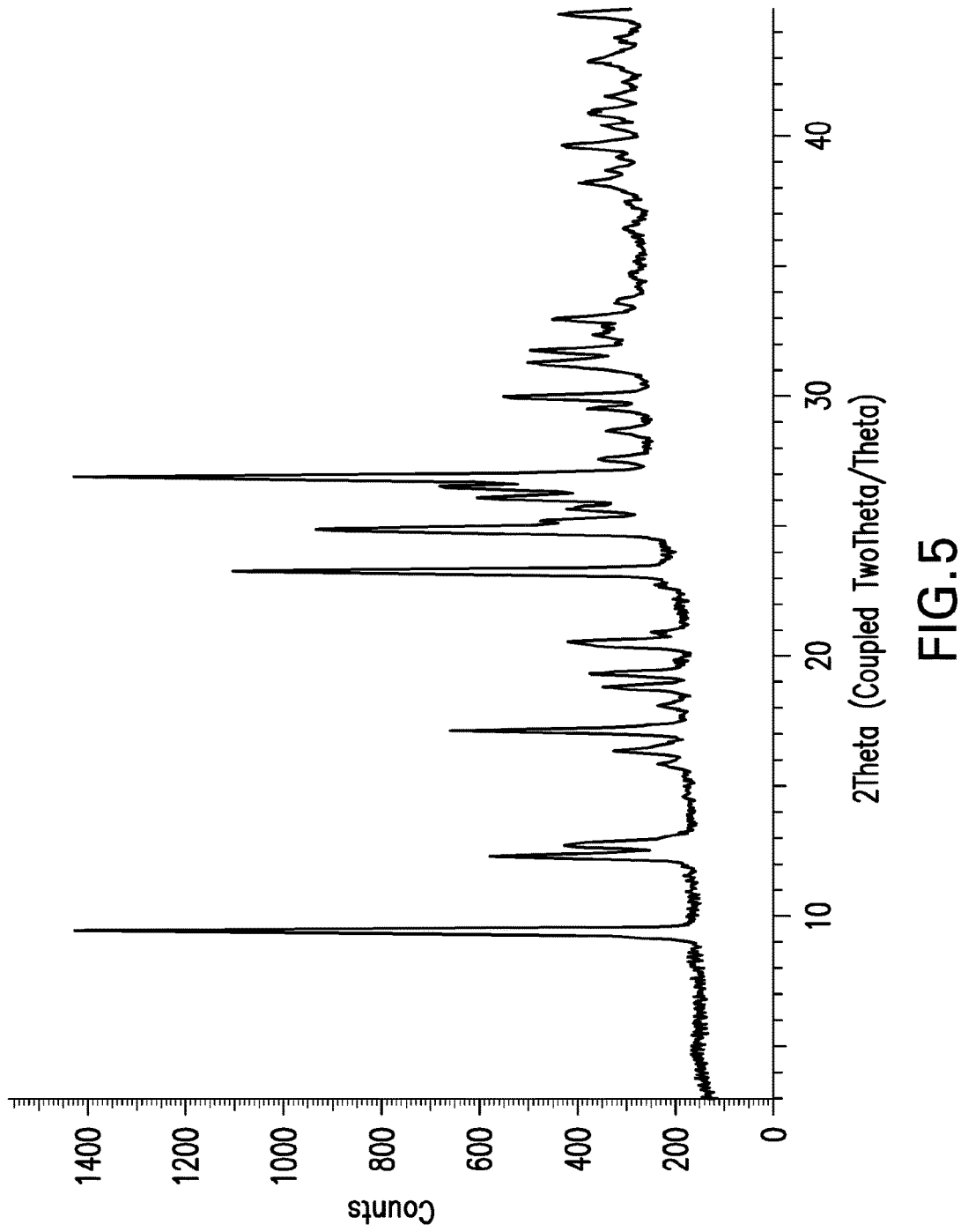
FIG. 5 provides an illustrative XRPD spectrum for the sulfate salt of the compound of Formula I, designated herein as Form C, showing degrees 2θ (2-theta) on the X-axis and relative intensity on the Y-axis.

In yet another aspect of embodiment 3, a crystalline form of the sulfate salt of the compound of Formula I has an XRPD pattern substantially as shown in FIG. 5.

The crystalline form of the sulfate salt of 5-bromo-2,6-di(1H-pyrazol-1-yl)-pyrimidin-4-amine may be characterized thermally. In one embodiment, a crystalline form of the sulfate salt of the compound of Formula I has a differential thermogravimetric profile comprising an endothermic peak starting at about 188.44° C. with an enthalpy ΔH of 117.42 J/g.

Figure 6:
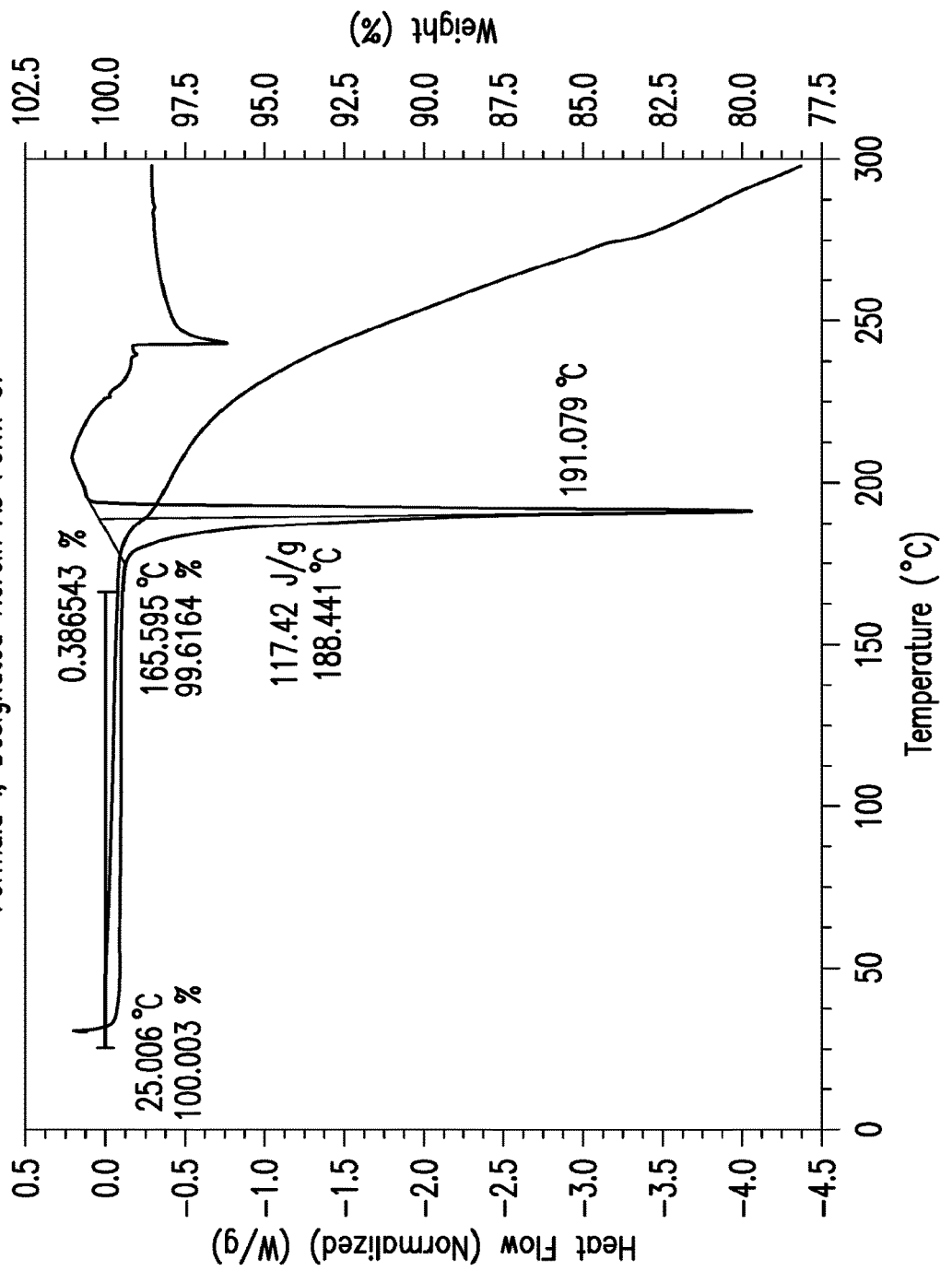
FIG. 6 provides an illustrative DSC/TGA for the sulfate salt of the compound of Formula I, designated herein as Form C.

In another aspect of embodiment 3, a crystalline form of the sulfate salt of the compound of Formula I has a DSC thermogram that is substantially as shown in FIG. 6. It should be understood that hydrated forms may yield different thermograms (in terms of peak shape and profile) depending on instrument parameters, thus the same material may have thermograms that look substantially different from each other when the data is generated on two different instruments.

In another aspect of embodiment 3, a crystalline form of the sulfate salt of the compound of Formula I has a thermo gravimetric analysis (TGA) diagram substantially the same as that shown in shown in FIG. 6. The weight loss is 0.4% at 166° C. by TGA.

In yet another embodiment, the crystalline form C is substantially phase pure.

In embodiment 4, the present disclosure provides a crystalline form of the mesylate salt of 5-bromo-2,6-di(1H-pyrazol-1-yl)pyrimidin-4-amine (modification 1=Form D) having an X-ray powder diffraction (XRPD) pattern comprising a representative peak, in terms of °2θ, at 24.0±0.2°2θ. In another aspect of embodiment 4, the XRPD pattern further comprises one or more additional representative peaks chosen from 20.3±0.2°2θ, and 10.1±0.2°2θ. Accordingly, the XRPD pattern for the crystalline form 1 (also referred to as modification 1) of the mesylate salt of the compound of Formula I may comprise one, two or three representative peaks above. In another embodiment, the crystalline form 1 of the mesylate salt of the compound of Formula I has an XRPD pattern that may further include one or more additional representative peaks chosen from 17.9±0.2°2θ, 26.4±0.2°2θ and 33.3±0.2°2θ. Thus, the XRPD pattern for the crystalline form 1 of the mesylate salt of the compound of Formula I may comprise one, two, three, four, five or six representative peaks disclosed above or disclosed in table 4.

In another aspect of embodiment 4, the mesylate form is characterized by a x-ray powder diffraction pattern comprising four or more 2θ values (CuKα λ=1.54184 Å) selected from the group consisting of 9.1±0.2°, 10.1±0.2°, 17.9±0.2°, 20.3±0.2°, 24.0±0.2°, 25.0±0.2°, 26.4±0.2°, and 33.3±0.2°, measured at a temperature of about 25° C. and an x-ray wavelength, λ, of 1.54184 Å.

Figure 7:
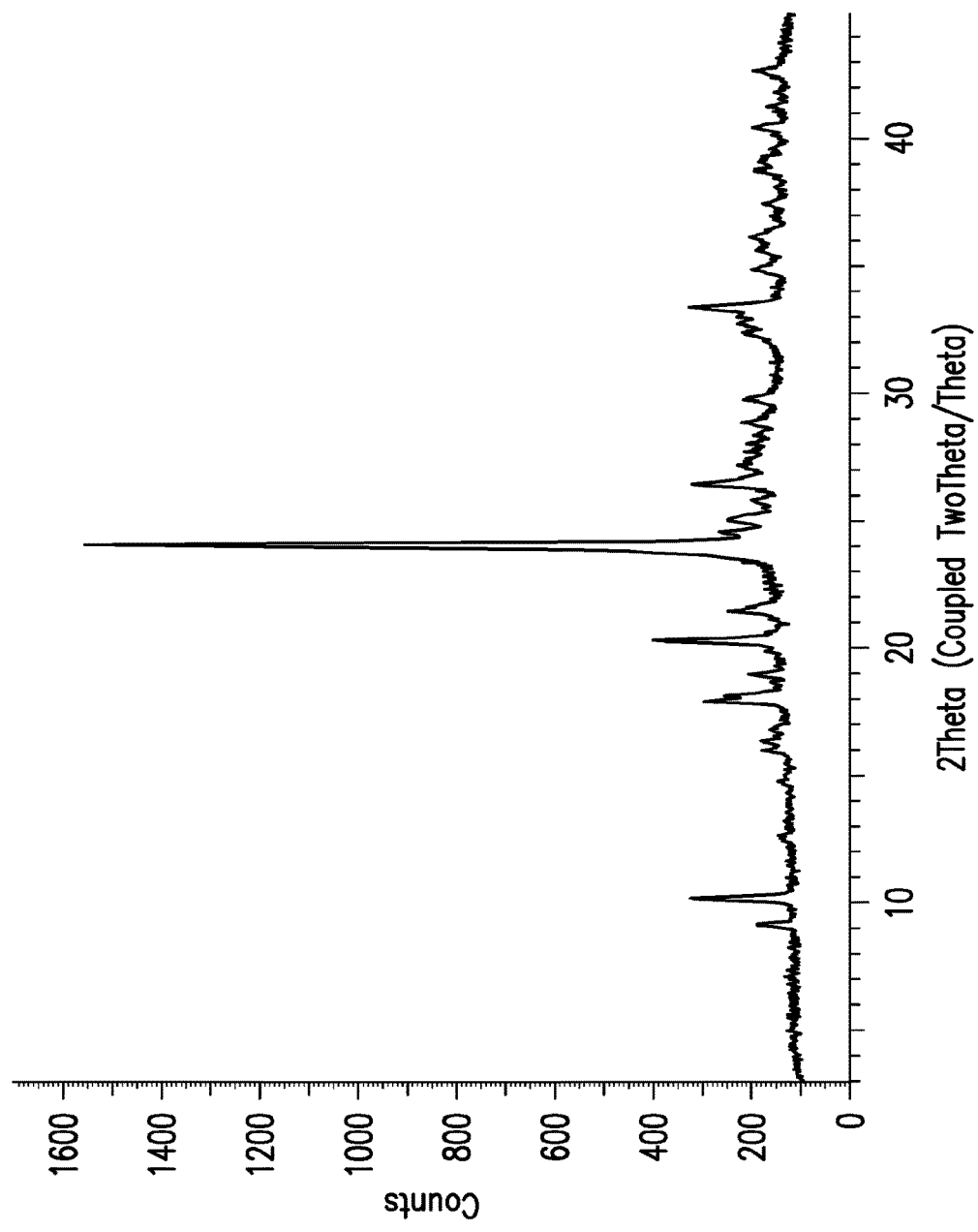
FIG. 7 provides an illustrative XRPD spectrum for the mesylate salt (Modification 1) of the compound of Formula I, designated herein as Form D, showing degrees 2θ (2-theta) on the X-axis and relative intensity on the Y-axis.

In yet another aspect of embodiment 4, a crystalline form 1 of the mesylate salt of the compound of Formula I has an XRPD pattern substantially as shown in FIG. 7.

The crystalline form 1 (also referred to as modification 1) of the mesylate salt of 5-bromo-2,6-di(1H-pyrazol-1-yl)-pyrimidin-4-amine may be characterized thermally. In one embodiment, a crystalline form of the mesylate salt of the compound of Formula I has a differential thermogravimetric profile comprising an endothermic peak starting at about 177.10° C. with enthalpy ΔH of 122.19 J/g.

Figure 8:
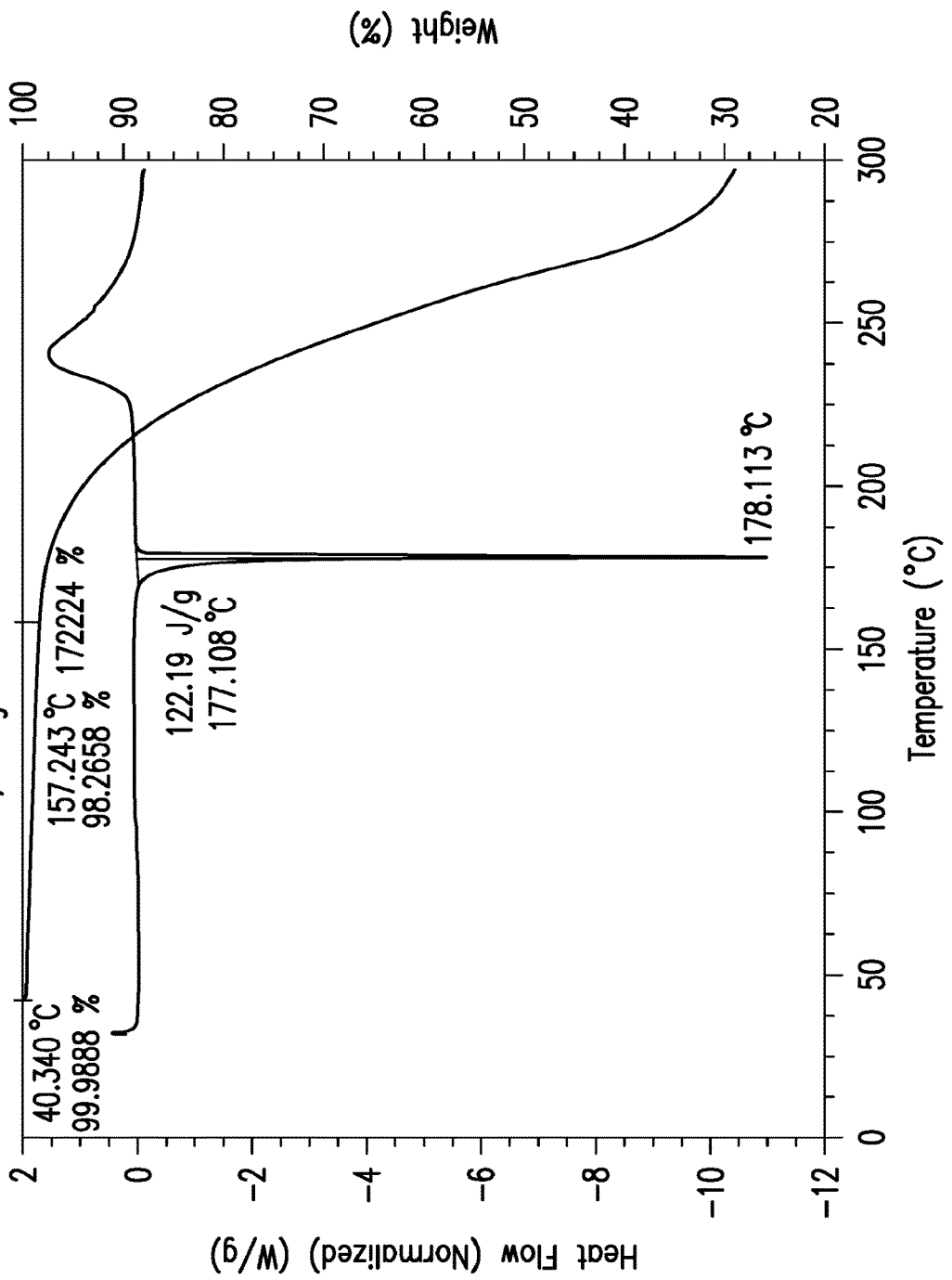
FIG. 8 provides an illustrative DSC/TGA for the mesylate salt (Modification 1) of the compound of Formula I, designated herein as Form D.

In another aspect of embodiment 4, a crystalline form 1 of the mesylate salt of the compound of Formula I has a DSC thermogram that is substantially as shown in FIG. 8. It should be understood that hydrated forms may yield different thermograms (in terms of peak shape and profile) depending on instrument parameters, thus the same material may have thermograms that look substantially different from each other when the data is generated on two different instruments.

In another aspect of embodiment 4, a crystalline form 1 of the mesylate salt of the compound of Formula I has a thermo gravimetric analysis (TGA) diagram substantially the same as that shown in shown in FIG. 8. The weight loss by TGA is about 1.7% at 157° C.

In yet another embodiment, the crystalline form D is substantially phase pure.

In embodiment 5, the present disclosure provides a crystalline form of the mesylate salt of 5-bromo-2,6-di(1H-pyrazol-1-yl)pyrimidin-4-amine (modification 2=Form E) having an X-ray powder diffraction (XRPD) pattern comprising a representative peak, in terms of °2θ, at 26.6±0.2°2θ. In another aspect of embodiment 5, the XRPD pattern further comprises one or more additional representative peaks chosen from 22.1±0.2° 2θ, 23.4±0.2°2θ and 16.6 0.2°2θ. Accordingly, the XRPD pattern for the crystalline form 2 of the mesylate salt of the compound of Formula I may comprise one, two, three or four representative peaks above. In another embodiment, the crystalline form 2 of the mesylate salt of the compound of Formula I has an XRPD pattern that may further include one or more additional representative peaks chosen from 9.0±0.2°2θ, 21.0±0.2°2θ, 24.1±0.2°2θ and 29.9±0.2°2θ. Thus, the XRPD pattern for the crystalline form 2 of the mesylate salt of the compound of Formula I may comprise one, two, three, four, five or six representative peaks disclosed above or disclosed in table 5.

In another aspect of embodiment 5, the mesylate form is characterized by a x-ray powder diffraction pattern comprising four or more 2θ values (CuKα λ=1.54184 Å) selected from the group consisting of 9.0±0.2°, 16.6±0.2°, 18.0±0.2°, 21.0±0.2°, 22.1±0.2°, 23.4±0.2°, 24.1±0.2°, 25.0±0.2°2θ, 26.7±0.2°2θ and 29.9±0.2°, measured at a temperature of about 25° C. and an x-ray wavelength, λ, of 1.54184 Å.

Figure 9:
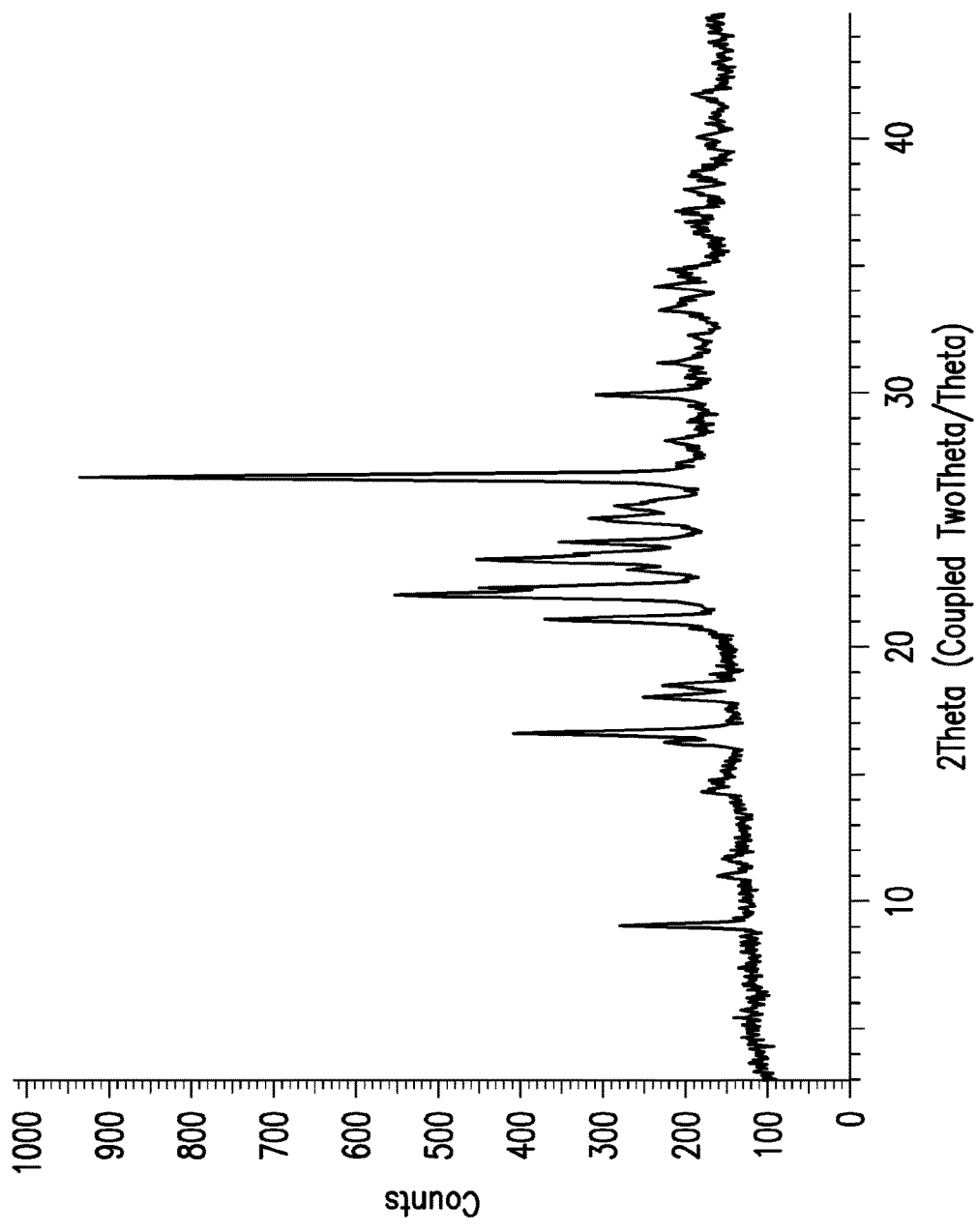
FIG. 9 provides an illustrative XRPD spectrum for the mesylate salt (Modification 2) of the compound of Formula I, designated herein as Form E, showing degrees 2θ (2-theta) on the X-axis and relative intensity on the Y-axis.

In yet another aspect of embodiment 5, a crystalline form 2 of the mesylate salt of the compound of Formula I has an XRPD pattern substantially as shown in FIG. 9.

The crystalline form 2 of the mesylate salt of 5-bromo-2,6-di(1H-pyrazol-1-yl)-pyrimidin-4-amine may be characterized thermally. In one embodiment, a crystalline form of the mesylate salt of the compound of Formula I has a differential thermogravimetric profile comprising an endothermic peak starting at about 168.84° C. with enthalpy ΔH of 113.21 J/g.

Figure 10:
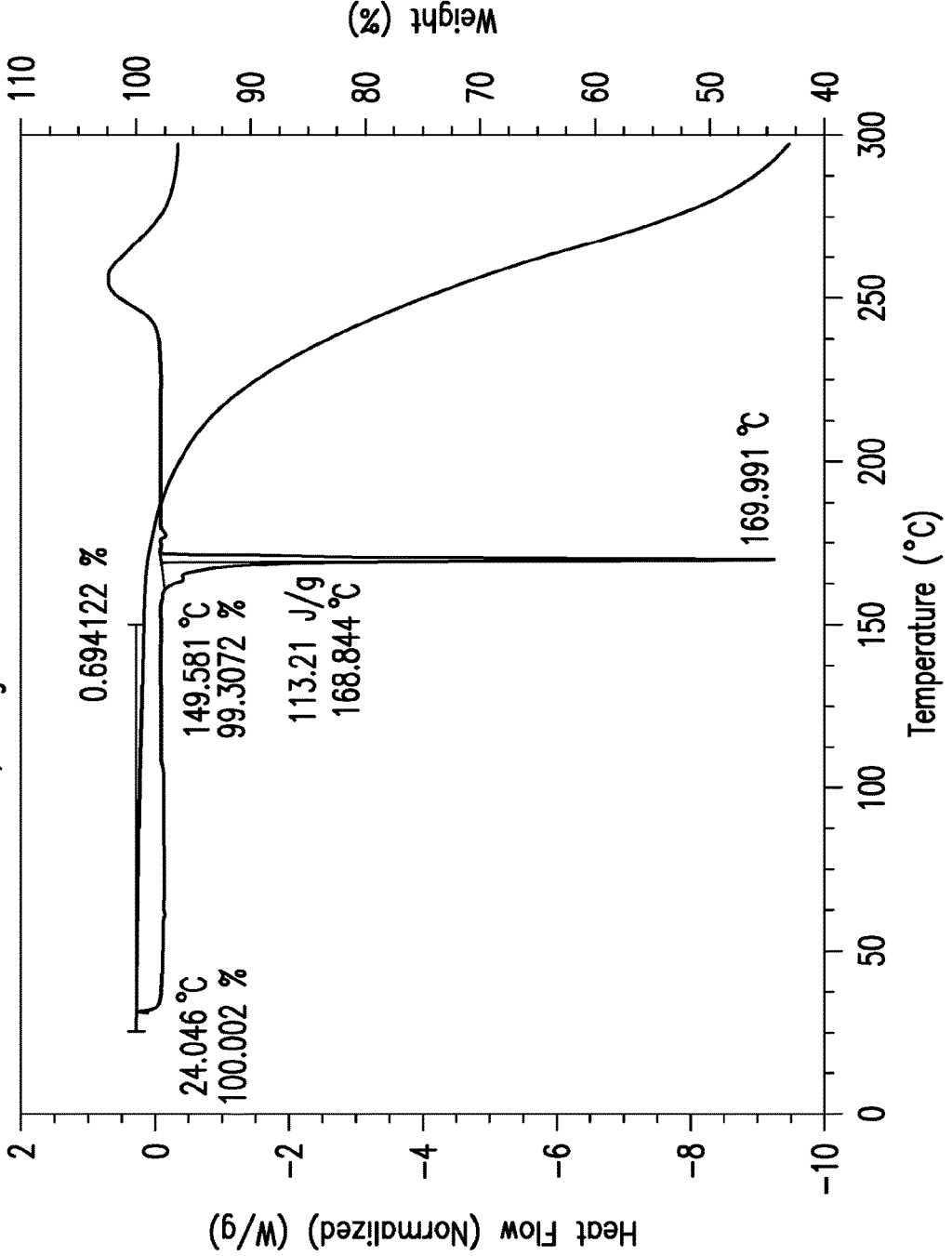
FIG. 10 provides an illustrative DSC/TGA for the mesylate salt (Modification 2) of the compound of Formula I, designated herein as Form E.

In another aspect of embodiment 5, a crystalline form 2 of the mesylate salt of the compound of Formula I has a DSC thermogram that is substantially as shown in FIG. 10. It should be understood that hydrated forms may yield different thermograms (in terms of peak shape and profile) depending on instrument parameters, thus the same material may have thermograms that look substantially different from each other when the data is generated on two different instruments.

In another aspect of embodiment 5, a crystalline form 2 of the mesylate salt of the compound of Formula I has a thermo gravimetric analysis (TGA) diagram substantially the same as that shown in shown in FIG. 10. The weight loss by TGA is about 0.7% at 150° C.

In yet another embodiment, the crystalline form E is substantially phase pure.

In embodiment 6, the present disclosure provides a crystalline form of 5-bromo-2,6-di(1H-pyrazol-1-yl)pyrimidin-4-amine in its free form (modification 1=Form F) having an X-ray powder diffraction (XRPD) pattern comprising a representative peak, in terms of °2θ, at 8.2±0.2°2θ. In another embodiment, the XRPD pattern further comprises one or more additional representative peaks chosen from 24.9±0.2°2θ, 25.7±0.2°2θ and 26.5±0.2°2θ. Accordingly, the XRPD pattern for the crystalline form 1 (also referred to as modification 1) of the free form of the compound of Formula I may comprise one, two, three or four representative peaks above. In another embodiment, the crystalline form 1 of the free form of the compound of Formula I has an XRPD pattern that may further include one or more additional representative peaks chosen from 11.5±0.2°2θ, 16.4±0.2°2θ and 30.8±0.2°2θ, and. Thus, the XRPD pattern for the crystalline form 1 of the free form of the compound of Formula I may comprise one, two, three, four, five or six representative peaks disclosed above or disclosed in table 6.

In another aspect of embodiment 6, the crystalline form 1 of the free form is characterized by a x-ray powder diffraction pattern comprising four or more 2θ values (CuKα λ=1.54184 Å) selected from the group consisting of 8.2±0.2°, 11.5±0.2°, 16.4±0.2°, 16.9±0.2°, 18.1±0.2°, 24.9±0.2°, 25.6±0.2°, 25.7±0.2°2θ, 26.5±0.2°2θ and 30.8±0.2°, measured at a temperature of about 25° C. and an x-ray wavelength, λ, of 1.54184 Å.

Figure 11:
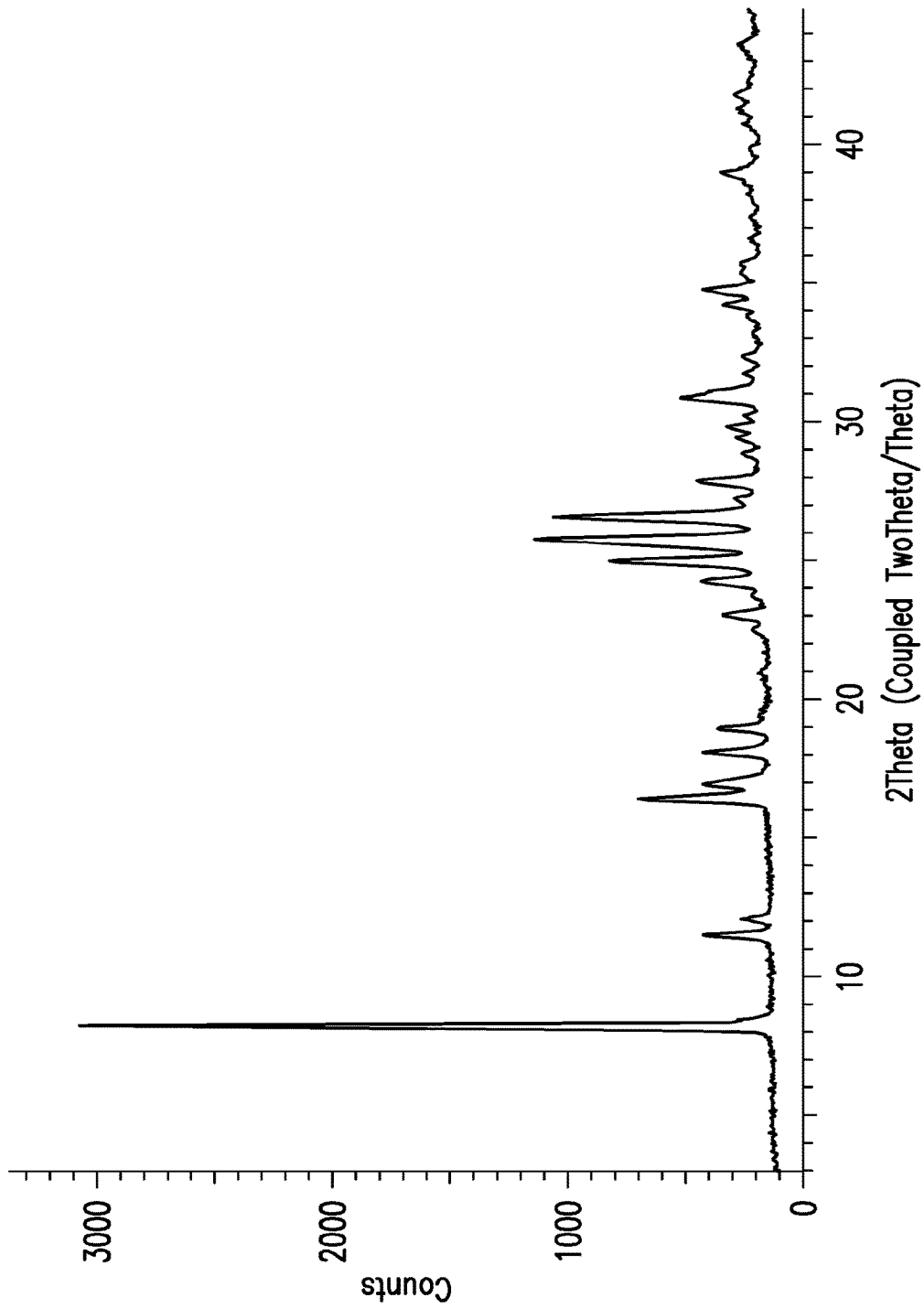
FIG. 11 provides an illustrative XRPD spectrum for the free form of the compound of Formula I (modification 1), designated herein as Form F, showing degrees 2θ (2-theta) on the X-axis and relative intensity on the Y-axis.

In yet another aspect of embodiment 6, a crystalline form 1 of the free form of the compound of Formula I has an XRPD pattern substantially as shown in FIG. 11.

The crystalline form 1 of the free form of 5-bromo-2,6-di(1H-pyrazol-1-yl)-pyrimidin-4-amine may be characterized thermally. In one embodiment, a crystalline form 1 of the free form of the compound of Formula I has a differential thermogravimetric profile comprising an endothermic peak starting at about 212.62° C. with an enthalpy ΔH of 104.22 J/g.

Figure 12:
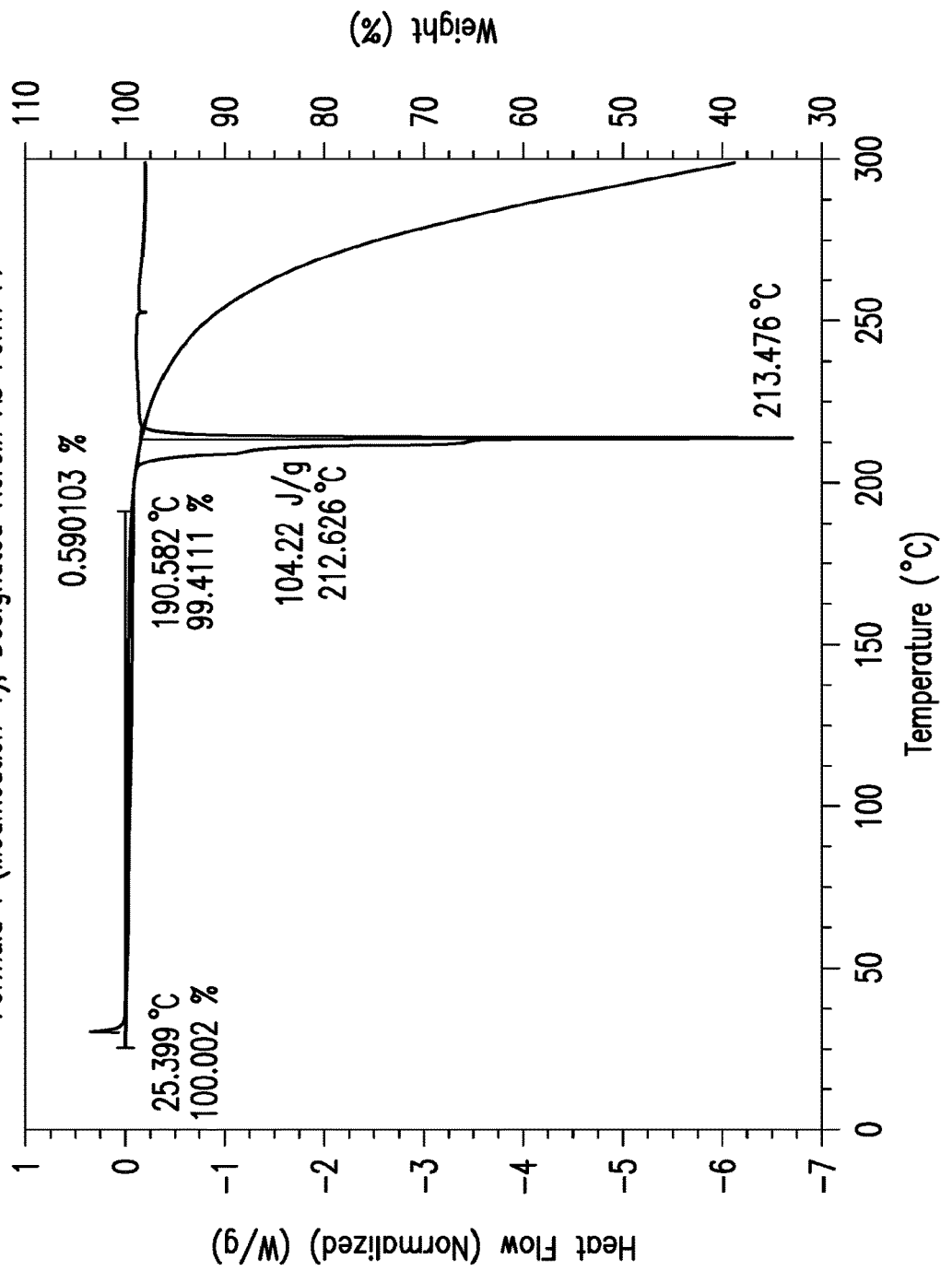
FIG. 12 provides an illustrative DSC/TGA for the free form of the compound of Formula I (modification 1), designated herein as Form F.

In another aspect of embodiment 6, a crystalline form 1 of the free form of the compound of Formula I has a DSC thermogram that is substantially as shown in FIG. 12. It should be understood that hydrated forms may yield different thermograms (in terms of peak shape and profile) depending on instrument parameters, thus the same material may have thermograms that look substantially different from each other when the data is generated on two different instruments.

In another aspect of embodiment 6, a crystalline form 1 of the free form of the compound of Formula I has a thermo gravimetric analysis (TGA) diagram substantially the same as that shown in shown in FIG. 12. The weight loss by TGA is about 0.6% at 190° C.

In yet another embodiment, the crystalline form F is substantially phase pure.

In embodiment 7, the present disclosure provides a crystalline form of 5-bromo-2,6-di(1H-pyrazol-1-yl)pyrimidin-4-amine in its free form (modification 2=Form G) having an X-ray powder diffraction (XRPD) pattern comprising a representative peak, in terms of °2θ, at 21.8±0.2°2θ. In another embodiment, the XRPD pattern further comprises one or more additional representative peaks chosen from 8.3±0.2°2θ, 25.2±0.2°2θ and 26.8±0.2°2θ. Accordingly, the XRPD pattern for the crystalline form 2 (also referred to as modification 2) of the free form of the compound of Formula I may comprise one, two, three or four representative peaks above.

In another embodiment, the crystalline form 2 of the free form of the compound of Formula I has an XRPD pattern that may further include one or more additional representative peaks chosen from 14.0±0.2°2θ, 16.7±0.2°2θ, and 30.7±0.2°2θ. Thus, the XRPD pattern for the crystalline form 2 of the free form of the compound of Formula I may comprise one, two, three, four, five or six representative peaks disclosed above or disclosed in table 7.

In another aspect of embodiment 7, the crystalline form 2 of the free form is characterized by a x-ray powder diffraction pattern comprising four or more 2θ values (CuKα λ=1.54184 Å) selected from the group consisting of 8.3±0.2°, 10.4±0.2°, 14.0±0.2°, 16.7±0.2°, 21.8±0.2°, 24.6±0.2°, 25.1±0.2°, 26.8±0.2°, 30.7±0.2°, 32.8±0.2°, and 42.5±0.2°2θ measured at a temperature of about 25° C. and an x-ray wavelength, λ, of 1.54184 Å.

Figure 13:
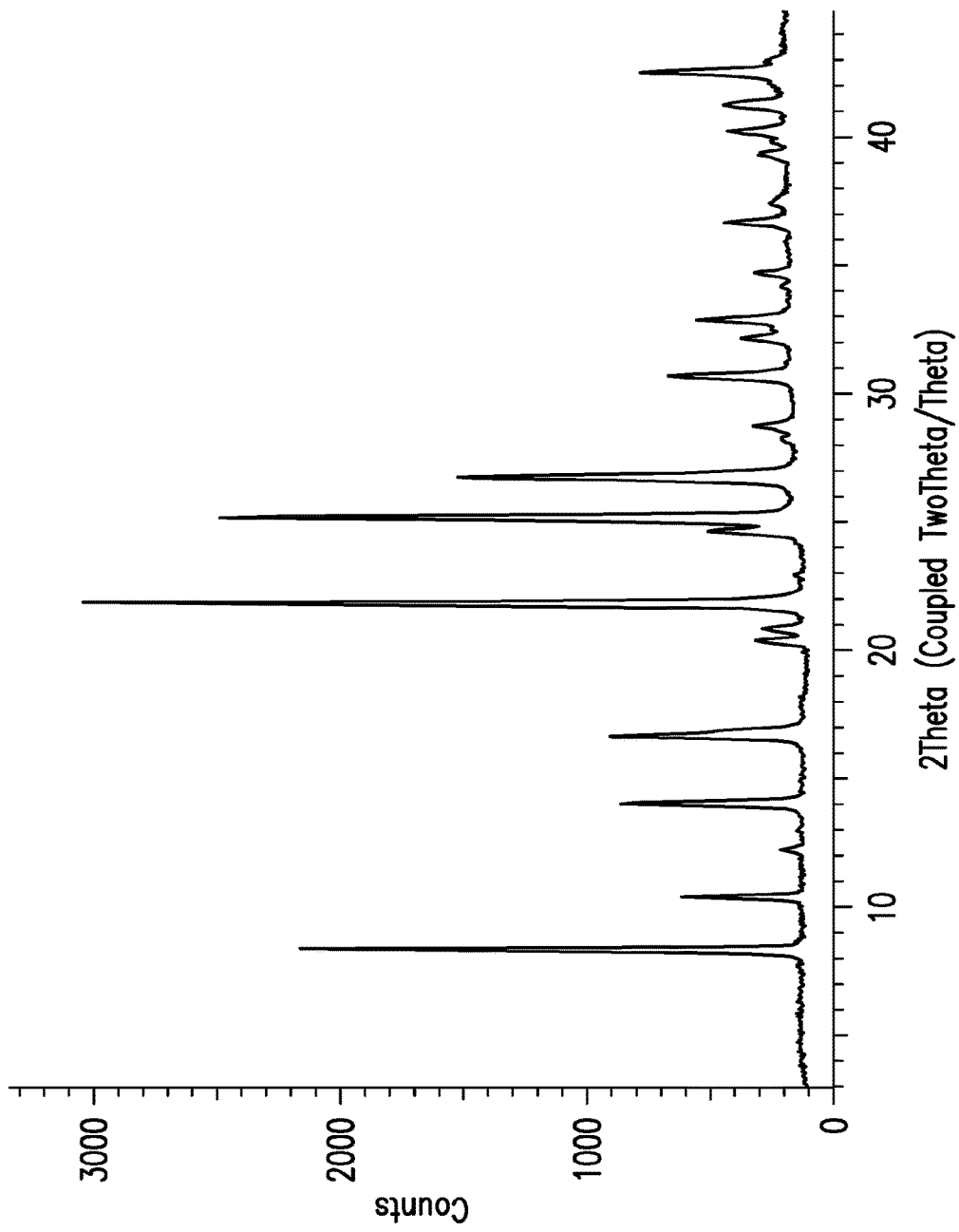
FIG. 13 provides an illustrative XRPD spectrum for the free form of the compound of Formula I (modification 2), designated herein as Form G, showing degrees 2θ (2-theta) on the X-axis and relative intensity on the Y-axis.

In yet another of embodiment 7, a crystalline form 2 of the free form of the compound of Formula I has an XRPD pattern substantially as shown in FIG. 13.

The crystalline form 2 of the free form of 5-bromo-2,6-di(1H-pyrazol-1-yl)-pyrimidin-4-amine may be characterized thermally. In one embodiment, a crystalline form of the free form 2 of the compound of Formula I has a differential thermogravimetric profile comprising an endothermic peak starting at about 202.95° C. with enthalpy ΔH of 14.84 J/g, and an endothermic peak starting at about 212.96° C. with enthalpy ΔH of 91.99 J/g.

Figure 14:
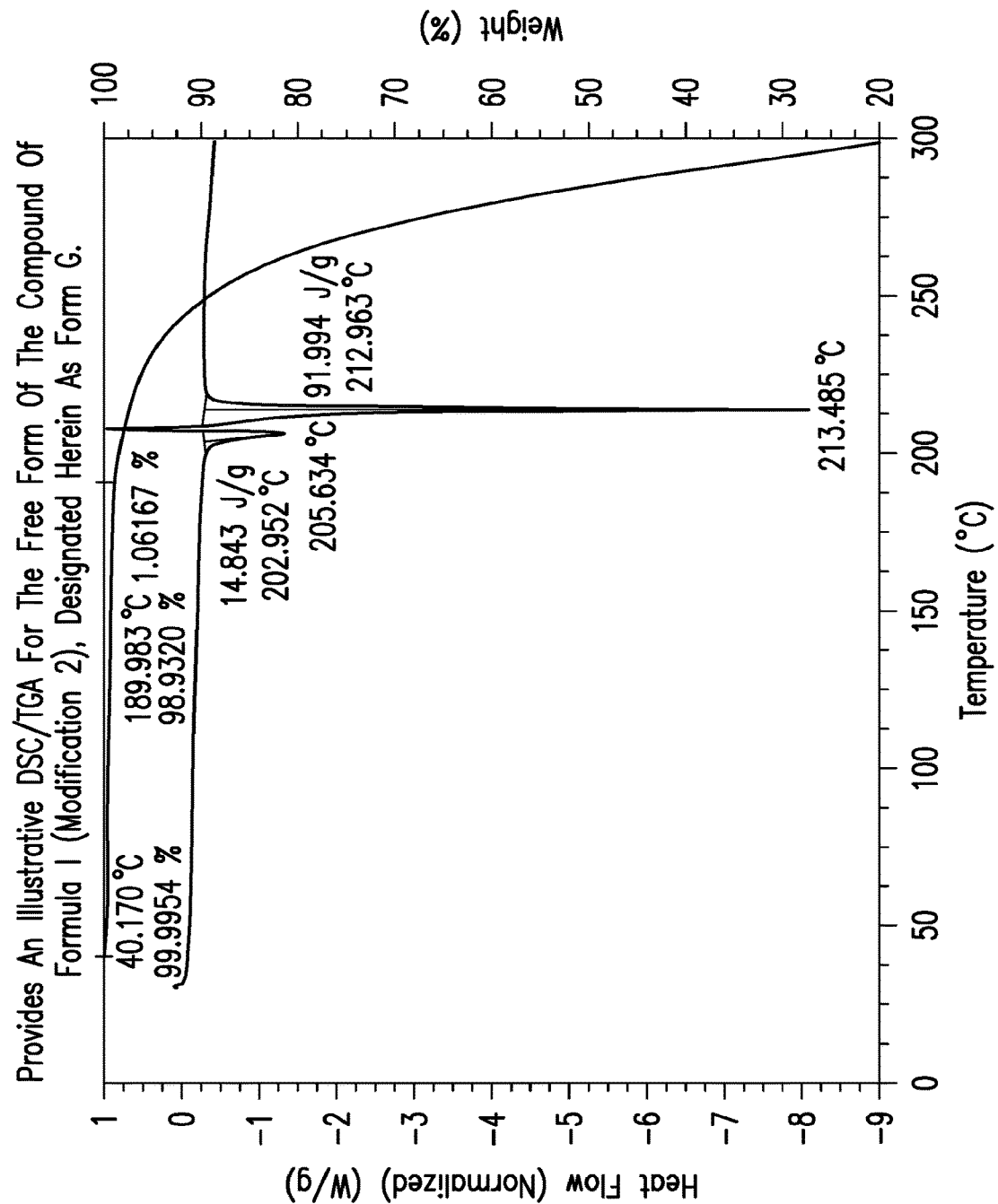
FIG. 14 provides an illustrative DSC/TGA for the free form of the compound of Formula I (modification 2), designated herein as Form G.

In another aspect of embodiment 7, a crystalline form 2 of the free form of the compound of Formula I has a DSC thermogram that is substantially as shown in FIG. 14. It should be understood that hydrated forms may yield different thermograms (in terms of peak shape and profile) depending on instrument parameters, thus the same material may have thermograms that look substantially different from each other when the data is generated on two different instruments.

In another aspect of embodiment 7, a crystalline form 2 of the free form of the compound of Formula I has a thermo gravimetric analysis (TGA) diagram substantially the same as that shown in shown in FIG. 14. The weight loss by TGA is about 1.06% at 190° C.

In embodiment 8, the invention relates to a pharmaceutical composition comprising a therapeutically effective amount of a crystalline form of 5-bromo-2,6-di(1H-pyrazol-1-yl)pyrimidin-4-amine (any one of forms A to G according to any one of embodiments 1 to 7 and any sub embodiments thereof), and at least one pharmaceutically acceptable excipient. In a particular embodiment, the invention relates to a pharmaceutical composition comprising crystalline form F, and a pharmaceutically acceptable excipient. In yet another aspect of embodiment 8, the invention relates to a pharmaceutical composition comprising crystalline form F in substantially pure phase. In yet another embodiment, the invention relates to a pharmaceutical formulation comprising crystalline form F and further comprising at least one other solid state form of 5-bromo-2,6-di(1H-pyrazol-1-yl)pyrimidin-4-amine. In one aspect of this embodiment, the other solid state form is crystalline form G. In yet another embodiment, the other solid state form is an amorphous form of 5-bromo-2,6-di(1H-pyrazol-1-yl)pyrimidin-4-amine. In a further embodiment, the amorphous form is a non-salt (free base) of 5-bromo-2,6-di(1H-pyrazol-1-yl)pyrimidin-4-amine.

In embodiment 9, the invention relates to a combination, in particular a pharmaceutical combination, comprising a therapeutically effective amount of a crystalline form of 5-bromo-2,6-di(1H-pyrazol-1-yl)pyrimidin-4-amine (any one of forms A to G, preferably form F), and one or more immunotherapeutic agents.

In embodiment 10, the invention relates to a method of treating cancer, in a subject in need thereof, the method comprising: administering to a subject in need thereof, a therapeutically effective amount of a crystalline form of 5-bromo-2,6-di(1H-pyrazol-1-yl)pyrimidin-4-amine (any one of forms A to G according to any one of embodiments 1 to 7 and any sub embodiments thereof, preferably form F), or a pharmaceutical composition according to embodiment 8, alone or in combination with one or more immunotherapeutic agents.

In embodiment 11, the invention relates to the use of a crystalline form of 5-bromo-2,6-di(1H-pyrazol-1-yl)pyrimidin-4-amine (any one of forms A to G according to any one of embodiments 1 to 7 and any sub embodiments thereof, preferably form F), or the use of a pharmaceutical composition according to embodiment 8, alone or in combination with one or more immunotherapeutic agents, for the treatment of cancer.

In embodiment 12, the invention pertains to a crystalline form of 5-bromo-2,6-di(1H-pyrazol-1-yl)pyrimidin-4-amine (any one of forms A to G according to any one of embodiments 1 to 7 and any sub embodiments thereof, preferably form F), or a pharmaceutical composition according to embodiment 8, for use in the treatment of cancer.

In embodiment 13, the invention pertains to a combination of a crystalline form of 5-bromo-2,6-di(1H-pyrazol-1-yl)pyrimidin-4-amine (any one of forms A to G according to any one of embodiments 1 to 7 and any sub embodiments thereof, preferably form F), and one or more immunotherapeutic agents, for use in the treatment of cancer.

In embodiment 14, the invention relates to a method of inhibiting adenosine A2a receptor, in a subject in need thereof comprising: administering to a subject a therapeutically effective amount of a crystalline form of 5-bromo-2,6-di(1H-pyrazol-1-yl)pyrimidin-4-amine (any one of forms A to G according to any one of embodiments 1 to 7 and any sub embodiments thereof, preferably form F), or a pharmaceutical composition according to embodiment 8.

In embodiment 15, the invention relates to a method according to embodiment 10, a use according to embodiment 11, a compound for use according to embodiment 12, or a combination for use according to embodiment 13, wherein the cancer is selected from wherein the cancer is selected from a lung cancer, a melanoma, a renal cancer, a liver cancer, a myeloma, a prostate cancer, a breast cancer, a colorectal cancer, a pancreatic cancer, a head and neck cancer, anal cancer, gastro-esophageal cancer, thyroid cancer, cervical cancer, a lymphoproliferative disease or a hematological cancer, T-cell lymphoma, B-cell lymphoma, a non-Hogdkin lymphoma, or a leukemia.

In embodiment 16, the invention relates to the method, use, crystalline form or combination for use of embodiment 15 wherein the cancer is carcinomas, specifically lung cancer and more specifically non-small cell lung cancer.

In embodiment 17, the invention relates to the method of embodiment 10, 15 or 16, a use according to embodiment 11, 15 or 16, or the combination for use according to embodiment 13, 15 or 16, wherein one or more immunotherapeutic agents are selected from the group consisting of anti-CTLA4 antibodies, anti-PD-1 antibodies and anti-PD-L1 antibodies.

In embodiment 18, the invention relates to the method of embodiment 10, 15 or 16, a use according to embodiment 11, 15 or 16, or the combination for use according to embodiment 13, 15 or 16, wherein the immunotherapeutic agent is selected from the group consisting of: Ipilimumab, Tremelimumab, Nivolumab, Pembrolizumab, Pidilizumab (CT-011), AMP-224, AMP-514 (MEDI0680-Medimmune), MPDL3280A (Genentech Roche), MEDI4736, MSB0010718C (Merck Serono), YW243.55.S70 and MDX-1105.

In embodiment 19, the invention relates to the method of embodiment 10, 15 or 16, a use according to embodiment 11, 15 or 16, or the combination for use according to embodiment 13, 15 or 16, wherein the immunotherapeutic agents is an anti-PD-1 antibody.

In embodiment 19A, the invention relates to the method of embodiment 10, 15 or 16, a use according to embodiment 11, 15 or 16, or the combination for use according to embodiment 13, 15 or 16, wherein the immunotherapeutic agents is an anti-PD-1 antibody selected from Nivulomab, Pembrolizumab, Pidilizumab, MEDI680 (AMP514 Medimmune), AMP224 (Medimmune), and antibodies described in US 2015/0210769)

In embodiment 20, the invention relates to the method, the use or the combination for use according to embodiment 19, wherein the anti-PD-1 antibody comprises:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

(c) a VH comprising a VHCDR1 amino acid sequence of SEQ ID NO: 41, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or (d) a VH comprising a VHCDR1 amino acid sequence of SEQ ID NO: 41; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In embodiment 21, the invention pertains to the method, the use or the combination for use according to embodiment 19, wherein the anti-PD-1 comprises a VH comprising the amino acid sequence of SEQ ID NO: 6 and a VL comprising the amino acid sequence of SEQ ID NO: 20.

In embodiment 22, the invention pertains to the method, the use or the combination for use according to embodiment 19, wherein the anti-PD-1 antibody comprises a heavy chain comprising the amino acid sequence of SEQ ID NO: 8 and a light chain comprising the amino acid sequence of SEQ ID NO: 22.

In embodiment 23, the invention pertains to the method, the use or the combination for use according to embodiment 19, wherein the anti-PD-1 antibody comprises a VH comprising the amino acid sequence of SEQ ID NO: 6 and a VL comprising the amino acid sequence of SEQ ID NO: 16.

In embodiment 24, the invention pertains to the method, the use or the combination for use according to embodiment 19, wherein the anti-PD-1 antibody comprises a heavy chain comprising the amino acid sequence of SEQ ID NO: 8 and a light chain comprising the amino acid sequence of SEQ ID NO: 18.

In embodiment 25, the invention pertains to the method, the use or the combination for use according to any one of embodiments 19-24, wherein the anti-PD-1 antibody molecule is administered at a dose of about 300 mg once every three weeks.

In embodiment 26, the invention pertains to the method, the use or the combination for use according to any one of embodiments 19-24, wherein the anti-PD-1 antibody molecule is administered at a dose of about 400 mg once every four weeks.

In embodiment 27, the invention relates to the method of embodiment 10, 15 or 16, a use according to embodiment 11, 15 or 16, or the combination for use according to embodiment 13, 15 or 16, wherein the immunotherapeutic agents is an anti-PD-L1 antibody.

In embodiment 27A, the invention relates to the method, the use or the combination for use according to embodiment 27, wherein the anti PD-L1 antibody molecule is selected from YW243.55.S70, MPDL3280A, MEDI-4736, MSB-0010718C, MDX-1105 and an anti PD-L1 antibody described in US 2016/0108123.

In embodiment 28, the invention relates to the method, the use or the combination for use according to embodiment 27, wherein the anti PD-L1 antibody molecule comprises:

(a) a heavy chain variable region (VH) comprising a VHCDR1 amino acid sequence of SEQ ID NO: 47, a VHCDR2 amino acid sequence of SEQ ID NO: 48, and a VHCDR3 amino acid sequence of SEQ ID NO: 46; and a light chain variable region (VL) comprising a VLCDR1 amino acid sequence of SEQ ID NO: 52, a VLCDR2 amino acid sequence of SEQ ID NO: 53, and a VLCDR3 amino acid sequence of SEQ ID NO: 54;

(b) a VH comprising a VHCDR1 amino acid sequence of SEQ ID NO: 44; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51;

(c) a VH comprising a VHCDR1 amino acid sequence of SEQ ID NO: 63, a VHCDR2 amino acid sequence of SEQ ID NO: 48, and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54; or (d) a VH comprising a VHCDR1 amino acid sequence of SEQ ID NO: 63; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51.

In embodiment 29, the invention relates to the method, the use or the combination for use according to embodiment 27, wherein the anti PD-L1 antibody molecule comprises a heavy chain variable domain comprising the amino acid sequence of SEQ ID NO: 55 and a light chain variable domain comprising the amino acid sequence of SEQ ID NO: 58.

In embodiment 30, the invention relates to the method, the use or the combination for use according to any one of embodiments 17-29, wherein immunotherapeutic agent is administered together in a single composition or administered separately in two or more different compositions forms.

In embodiment 31, the invention pertains to the method the method, the use or the combination for use according to any one of embodiments 17-29 wherein the immunotherapeutic agent is administered concurrently with, prior to, or subsequent to, a crystalline form of 5-bromo-2,6-di(1H-pyrazol-1-yl)pyrimidin-4-amine.

The crystalline forms described herein have been found to have advantageous properties. The criteria for selection are toxicological considerations, crystallinity, monomorphism, melting point, hygroscopicity, stability in bulk, compatibility with excipients, pH of aqueous solution, solubility in water and aqueous media, morphology, handling and polymorphism behaviors. Free form F has demonstrated superior behaviors.

Two crystalline forms of the free form of 5-bromo-2,6-di(1H-pyrazol-1-yl)pyrimidin-4-amine were identified, which included the crystalline form F and a crystalline form G, as discussed herein. Among the different free forms identified, crystalline Form F is the more thermodynamically stable as compared to the other free form G.

Competitive slurry experiments using 1:1 mixture of modification F and modification G were carried out at room temperature. The mixture of modification F and modification G completely converted to Modification F after equilibrium for 5 days. Modification G upon melting recrystallizes into modification F, thus indicating that Form F is more stable than form G.

Moreover, crystalline Form F was shown to have better chemical stability properties than crystalline Form G. In particular, Form F was shown to be physically and chemically stable in bulk when exposed for one week at 80° C. at ambient relative humidity (RH). Specifically, analysis of the crystalline Form F drug substance indicated that there was less than 1% degradation of the Form F material under these conditions. Form F also proved to be physically and chemically stable in bulk for one to two weeks at 50° C. at ambient relative humidity as well as at 50° C. at 75% relative humidity. Specifically, analysis of the crystalline Form F drug substance indicated that there was less than 1% degradation of the Form F material under both sets of conditions. Furthermore, Form F was physically and chemically stable under light stressed exposure.

In a pH stability study, 0.1% suspension/solution of Form F showed less than 0.5% degradation in buffer solutions of various pHs at 50° C. for one week, except at pH 1.2, where 1% degradation resulted. Additionally, form F shows superior property over the sulfate form C in term of stability in organic solvents. Therefore the crystalline form F has shown chemical stability in both solution and solid states.

Crystalline form F was shown to have better thermal stability properties than other disclosed crystalline forms A-E and G. After heating to 220° C. (melt) then cooling to 30° C., the crystalline form F remains unchanged. XRPD was carried out to study the stability of the crystalline form upon heating and cooling, and the results did not indicate a form change except some peaks shifted at high temperature.

Crystalline Form F was shown to have better physical stability properties than other disclosed crystalline forms (A-E and G). The crystallinity of form F was evaluated by XRPD after compression for 5 minutes at 0.5 ton with 0.8 cm diameter disc. The XRPD indicated no form change after compression.

The physical stability of crystalline form F was also evaluated in granulation simulation experiments. In these experiments granulating solvent was added dropwise to the crystalline form F until the solid is wetted sufficiently. The mixture was then ground in a mortar/pestle at room temperature (25° C. for 2-3 minutes) between each addition. The crystallinity of the material (post-grinding) was re-evaluated by XRPD and DSC. Under the aforementioned conditions using water or ethanol as the granulation solvent, XRPD results indicated no form change.

Both the free form F and the sulfate form C exhibited good stability when blended with four selected excipients, which are 1.Gelatin, 2 HPMC, 3 wet granulation mixture [MCC PH101 (45%); lactose monohydrate (44%); PVP K30 (4%), Crospovidone XL (5%), Aerosil (0.5%); Mg-Stearate (1.5%) and 20% w/w water added to the mixture)] and 4 dry blended mixture [Lactose USP (73%), Starch 1500 (20%), Explotab (5 wt %), Aerosil (0.5 wt %); Mg-Stearate (1.5 wt)] under 50° C./75% RH where about 1% degradation was observed.

The crystalline 5-bromo-2,6-di(1H-pyrazol-1-yl)pyrimidin-4-amine (Form F) exists primarily as a highly crystalline material.

Crystalline form F is non-hygroscopic. Water sorption-desorption isotherm recorded on a DVS (dynamic vapor sorption) instrument, 50%-90%-0% (cycle 1) and 0%-90%-50% (cycle 2) relative humidity (RH) at 25° C. in steps of 10% RH, dm/dt=0.002%/min showed that the crystalline form F absorbs less than 0.2% moisture up to 90% relative humidity.

Form F shows little to no phase change on exposure to humidity.

Form F shows solubility in aqueous buffers across pH 1 to pH 10 and bio-relevant media, of about 0.1 mg/mL in all tested media.

The free form F showed a slow intrinsic dissolution in 0.01N HCl pH=2 (0.0115 mg/cm$^2$/min), acetate buffer pH 4.7 (0.0085 mg/cm$^2$/min) and phosphate buffer pH 6.8 (0.0084 mg/cm$^2$/min).

The sulfate salt Form C is very hygroscopic when the relative humidity is above 70%.

It was further determined that the intrinsic dissolution rate of the sulfate salt (Form C) is slightly greater than that of the free form F in 0.01N HCl pH=2 (0.0592 mg/cm$^2$/min), acetate buffer pH 4.7 (0.0264 mg/cm$^2$/min) and phosphate buffer pH 6.8 (0.0277 mg/cm$^2$/min).

The sulfate salt (Form C) shows better morphology and therefore improve flow-ability but does not show any better solubility than the free form F since it dissociates in aqueous media.

DEFINITION

As used herein, the terms "about" and "substantially" indicate with respect to features such as endotherms, endothermic peak, exotherms, baseline shifts, etc., that their values can vary. With reference to X-ray diffraction peak positions, "about" or "substantially" means that typical peak position and intensity variability are taken into account. For example, one skilled in the art will appreciate that the peak positions (2θ) will show some inter-apparatus variability, typically as much as 0.2°. Occasionally, the variability could be higher than 0.2° depending on apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only. For DSC, variation in the temperatures observed will depend upon the rate of temperature change as well as sample preparation technique and the particular instrument employed. Thus, the endotherm/melting point values reported herein relating to DSC/TGA thermograms can vary 2° C. (and still be considered to be characteristic of the particular crystalline form described herein). When used in the context of other features, such as, for example, percent by weight (% by weight) the term "about" indicates a variance of ±3%.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Alternatively, solvates may occur as dimers or oligomers comprising more than one molecule or within the crystalline lattice structure.

As used herein "amorphous" refers to a solid form of a molecule, atom, and/or ions that is not crystalline. An amorphous solid does not display a definitive X-ray diffraction pattern.

As used herein, "substantially phase pure," when used in reference to any crystalline form of the compound of Formula I, means a compound having a phase purity of greater than about 90% by weight, including greater than about 90, 91, 92, 93, 94, 95, 96, 97, 98, and about 99% by weight, and also including equal to about 100% by weight of the compound of Formula I, based on the weight of the compound on an anhydrous basis. The term "phase pure" or "phase purity" herein refers to phase homogeneity with respect to a particular solid state form of the compound of Formula I and does not necessarily imply a high degree of chemical purity absent an express statement to that effect. Phase purity may be determined according to methods known in the art, for example, using XRPD to do quantitative phase analysis using one or more approaches known in the art, for example, via an external standard method, direct comparisons of line (peak) characteristics which are attributed to different phases in a particular spectra, or via an internal standard method. However XRPD quantification of phase purity can be complicated by the presence of amorphous material. Accordingly, other methods that may be useful for determining phase purity include, for example, solid state NMR spectroscopy, Raman and/or infrared spectroscopy. One of skilled in the art would readily understand these methods and how to employ these additional (or alternative) methods for determining phase purity.

As used herein, "substantially chemically pure" when used in reference to any crystalline form of the compound of Formula I, means a compound having a chemical purity greater than about 90% by weight, including greater than about 90, 91, 92, 93, 94, 95, 96, 97, 98, and about 99% by weight, and also including equal to about 100% by weight of the compound of Formula I, based on the weight of the salt (on an anhydrous basis). The remaining material generally comprises other compounds, such as for example, other stereoisomers of the compound of Formula I, reaction impurities, starting materials, reagents, side products, and/or other processing impurities arising from the preparation and/or isolation and/or purification of the particular crystalline form. For example, a crystalline form of the compound of Formula I may be deemed to be substantially chemically pure if it has been determined to have a chemical purity of greater than about 90% by weight, as measured by standard and generally accepted methods known in the art, where the remaining less than about 10% by weight constitutes other materials such as other stereoisomers of the compound of Formula I, reaction impurities, starting materials, reagents, side products, and/or processing impurities. Chemical purity may be determined according to methods known in the art, for example, high performance liquid chromatography (HPLC), LC-MS (liquid chromatography-mass spectrometry), nuclear magnetic resonance (NMR) spectroscopy, or infrared spectroscopy. One of skill in the art would readily understand these methods and how to employ these additional (or alternative) methods for determining chemical purity.

The term "a therapeutically effective amount" of a compound of the present invention refers to an amount of the compound of the present invention that will elicit a biological or medical response in a subject, for example, reduction or inhibition of an enzyme or a protein activity, or ameliorate symptoms, alleviate conditions, or slow or delay disease progression, etc. In one non-limiting embodiment, the term "a therapeutically effective amount" refers to the amount of the compound of the present invention that, when administered to a subject, is effective to (1) at least partially alleviating, inhibiting, and/or ameliorating a condition, or a disorder or a disease (i) mediated by adenosine A2a receptor, or (ii) associated with adenosine or the activity of adenosine A2a receptor, or (iii) characterized by activity (normal or abnormal) of adenosine A2a receptor; or (2) reducing or inhibiting the activity of adenosine A2a receptor. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of adenosine A2a receptor; or at least partially reducing or inhibiting the expression of adenosine A2a receptor.

As used herein, the term "subject" refers to an animal. Preferably, the animal is a mammal. A subject refers to for example, primates (e.g. humans), cows, sheep, goats, horses, dogs, cats, rabbits, rats, mice, fish, birds and the like. In a preferred embodiment, the subject is a human.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

As used herein, the term "inhibit", "inhibition" or "inhibiting" refers to the reduction or suppression of a given condition, symptom, or disorder, or disease, or a significant decrease in the baseline activity of a biological activity or process.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In one embodiment, "treat" or "treating" refers to delaying the progression of the disease or disorder.

As used herein, the term "prevent", "preventing" or "prevention" of any disease or disorder refers to the prophylactic treatment of the disease or disorder; or delaying the onset of the disease or disorder.

As used in the present document the term "cancer" is used to designate a group of diseases involving abnormal cell growth with the potential to invade or spread to other parts of the body. Cancers are classified by the type of cell that the tumor cells resemble and is therefore presumed to be the origin of the tumor. These types include carcinoma, sarcoma, lymphoma and leukemia, germ cell tumor and blastoma.

As used in the present document the term carcinoma is used to designate cancers derived from epithelial cells. This group includes many of the most common cancers, particularly in the aged, and include nearly all those developing in the breast, prostate, lung, pancreas, and colon.

For example the term "cancer" includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, B-cell lymphoma, a non-Hogkin lymphoma, or a leukemia (e.g., a myeloid leukemia or a lymphoid leukemia).

In another embodiment, the cancer can be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer (e.g., differentiated or undifferentiated metastatic or locally recurrent nasopharyngeal carcinoma), or breast cancer.

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer or small cell lung cancer.

As used in the present document the term lung cancer (also known as carcinoma of the lung or pulmonary carcinoma) is used to designate malignant lung tumors characterized by uncontrolled cell growth in tissues of the lung.

As used in the present document the term non-small-cell lung carcinoma (NSCLC) is used to designate any type of lung cancer other than small cell lung carcinoma (SCLC).

As used in the present document the term immunotherapeutic treatment refers to a broad class of therapies designated to elicit immune-mediated destruction of tumor cells. In said therapies are used immunotherapeutic agents.

As used in the present document the term immunotherapeutic agents refer to compounds useful to carrying out immunotherapeutic treatment of cancer, such as agent selected from the group consisting of anti-CTLA4 antibodies, such as Ipilimumab and Tremelimumab, anti-PD-1 antibodies such as MDX-1106, MK3475, CT-011, AMP-224 or an anti-PD-1 antibody molecule as described in WO2015/112900; and anti-PD-L1 antibodies such as MEDI4736, MDX-1105 or an anti-PD-L1 antibody described in US 2016/0108123.

As used herein, the term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

As used herein, the term "Programmed Death Ligand 1" or "PD-L" include isoforms, mammalian, e.g., human PD-L1, species homologs of human PD-1, and analogs comprising at least one common epitope with PD-L1. The amino acid sequence of PD-L1, e.g., human PD-1, is known in the art, e.g., Dong et al. (1999) *Nat Med.* 5(12):1365-9; Freeman et al. (2000) *J Exp Med.* 192(7):1027-34).

As used herein the term "combination" refers to either a fixed combination in one dosage unit form, or a combined administration where a crystalline form of compound of Formula I and a combination partner (i.e. an immunotherapeutic agent) may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" and "combination product" are used interchangeably and refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that a crystalline form of the compound of Formula I and a combination partner (i.e. immunotherapeutic agent), are both administered to a patient simultaneously in the form of a single entity or dosage. The term "non-fixed combination" means that a crystalline form of the compound of Formula I and a combination partner (i.e. the immunotherapeutic agent), are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. In a preferred embodiment, the pharmaceutical combination is a non-fixed combination.

The term "combination therapy" refers to the administration of two or more therapeutic agents to treat a cancer as described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Pharmaceutical Composition, Combination, Dosage and Administration

In some embodiments the crystalline forms of 5-bromo-2,6-di(1H-pyrazol-1-yl)pyrimidin-4-amine described herein can be used alone or they can be formulated into a pharmaceutical composition that also contains at least one pharmaceutically acceptable excipient, and often contains at least two or more pharmaceutically acceptable excipients. Some suitable excipients are disclosed herein. Other excipients may be used that are known in the art without departing from the intent and scope of the present application.

In some embodiments, the present invention utilizes a pharmaceutical composition comprising a compound of the present invention and a pharmaceutically acceptable excipient. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, carriers or buffering agents, as well as adjuvants, such as solvents, preservatives, stabilizers, wetting agents, emulsifiers and bulking agents, etc.

Typically, the pharmaceutical compositions are tablets or capsules comprising the active ingredient together with at least one excipient, such as:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired;

d) carriers such as an aqueous vehicle containing a co-solvating material such as captisol, PEG, glycerin, cyclodextrin, or the like;

e) disintegrants, e.g., starches, agar, alginic acid or its sodium salt, or effervescent mixtures; and/or f) absorbents, colorants, flavors and sweeteners.

Tablets may be either film coated or enteric coated according to methods known in the art.

Preferably, the compound or composition is prepared for oral administration, such as a tablet or capsule, for example, and optionally packaged in a multi-dose format suitable for storing and/or dispensing unit doses of a pharmaceutical product. Examples of suitable packaging include, but are not limited to, hermetically sealed foils, unit dose containers (e. g., vials), blister packs, and strip packs.

Tablets may contain the active ingredient in admixture with nontoxic, pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about 103 molar and 10-9 molar concentrations. A therapeutically effective amount in vivo may range depending on the route of administration, between about 0.1-500 mg/kg, or between about 1-100 mg/kg.

In other embodiments, a pharmaceutical composition is provided which comprises at least one compound according to the embodiments supra and at least one carrier.

The crystalline forms of 5-bromo-2,6-di(1H-pyrazol-1-yl)pyrimidin-4-amine described herein are also useful as active pharmaceutical ingredients (APIs) as well as materials for preparing formulations that incorporate one or more pharmaceutically acceptable excipients and are suitable for administration to human subjects. In some embodiments these formulations will be a pharmaceutical product, such as, for example, a solid oral dosage form such as tablets and/or capsules. In the preparation of these formulations it may be the case that the crystalline form of 5-bromo-2,6-di(1H-pyrazol-1-yl)pyrimidin-4-amine is not detectable in any sufficient amount. Such is the case where a crystalline API is contacted with one or more pharmaceutically acceptable excipients in the presence of a solvent such as, for example, water, in an amount sufficient to promote dissolution of the API such that its crystalline character is lost and therefore is absent in the final pharmaceutical product.

As used herein, the term "pharmaceutically acceptable excipients" includes any and all solvents, carriers, diluents, dispersion media, coatings, surfactants, antioxidants, preservatives (e.g., antibacterial agents, antifungal agents, antioxidants), isotonic agents, absorption delaying agents, salts, drug stabilizers, binders, additives, bulking agents, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). It should be understood that unless a conventional excipient is incompatible with the active ingredient, the use of any conventional excipient in any therapeutic or pharmaceutical compositions is contemplated by the present application.

Accordingly, in an embodiment of the disclosure, a crystalline form of 5-bromo-2,6-di(1H-pyrazol-1-yl)pyrimidin-4-amine (any of Form A to G) is provided in a substantially phase pure form. This crystalline form of a 5-bromo-2,6-di (1H-pyrazol-1-yl)pyrimidin-4-amine (any of Form A to G) in substantially phase pure form may be used to prepare pharmaceutical compositions which may further comprising one or more pharmaceutically acceptable excipients. In some embodiments the crystalline form of 5-bromo-2,6-di (H-pyrazol-1-yl)pyrimidin-4-amine may not retain its crystallinity in the pharmaceutical composition. For example, in some embodiments crystalline Form A, B, C, D, E, F or G may be used in a process to prepare a pharmaceutical composition that, for example, involves spray drying or wet granulation; thus it is expected that little to no crystalline Form A, B, C, D, E, F or G will be detected in the resulting pharmaceutical composition. It should be understood that the term "contacting" as used herein expressly includes methods of combining the crystalline forms of the compound of Formula I described herein where the crystallinity of the API is maintained or the crystallinity of the API is lost as a result of the process of preparing the pharmaceutical composition or pharmaceutical product.

Therapeutic Kits

In one embodiment, the invention provides a kit comprising two or more separate pharmaceutical compositions, at least one of which contains a crystalline form of the compound of formula (I) (any one of Form A to G). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, a crystalline form of a compound of Formula (I) (i.e. any one of Form A through G) and the other immunotherapeutic agent may be manufactured and/or formulated by the same or different manufacturers. Moreover, a crystalline form of the compound of Formula (I) and the other therapeutic may be brought together into a combination therapy: (i) prior to release of the combination product to physicians (e.g. in the case of a kit comprising a crystalline form of compound of Formula (I) and the other therapeutic agent); (ii) by the physician themselves (or under the guidance of the physician) shortly before administration; (iii) in the patient themselves, e.g. during sequential administration of a crystalline form of the compound of Formula (I) and the other therapeutic agent.

Accordingly, the invention provides the use of a crystalline form according to any one of embodiments 1 to 7 (any one of form A to G), for treating cancer, wherein the medicament is prepared for administration with another immunotherapeutic agent. The invention also provides the use of an immunotherapeutic agent for treating cancer, wherein the medicament is administered with a crystalline form of the compound of Formula (I).

The invention also provides a crystalline form of the compound of Formula (I) (i.e. any one of Form A to G), for use in a method of treating cancer, wherein the crystalline form of compound of Formula (I) is prepared for administration with another immunotherapeutic agent. The invention also provides another immunotherapeutic agent for use in a method of treating cancer, wherein the other immunotherapeutic agent is prepared for administration with a crystalline form of compound of Formula (I). The invention also provides crystalline form of compound of Formula (I), for use in a method of treating cancer, wherein the crystalline form of compound of Formula (I) is administered with another immunotherapeutic agent. The invention also provides another immunotherapeutic agent for use in a method of treating cancer, wherein the other therapeutic agent is administered with a crystalline form of compound of Formula (I).

The invention also provides the use of a crystalline form of compound of Formula (1), for treating cancer, wherein the patient has previously (e.g. within 24 hours) been treated with another immunotherapeutic agent. The invention also provides the use of another immunotherapeutic agent for treating cancer, wherein the patient has previously (e.g. within 24 hours) been treated with a crystalline form of compound of Formula (I).

Combination Therapy:

In one embodiment, a pharmaceutical combination (or combination product) comprises a crystalline form according to any one of embodiments 1 to 7, and one or more immunotherapeutic agents selected from the group consisting of anti-CTLA4 antibodies, such as Ipilimumab and Tremelimumab, anti-PD-1 antibodies such as MDX-1106 (Nivolumab), MK3475 (Pembrolizumab), CT-011 (Pidilizumab), AMP-224, AMP-514 (MEDI0680 Medimmune) or an anti-PD-1 antibody molecule as described in WO2015/112900 (US2015/0210769); and anti-PD-L1 antibodies such as MPDL3280A, MEDI4736, MSB0010718C (Merch Sorono), YW243.55.S70, MDX-1105 or an anti-PD-L1 antibody molecules are disclosed in US 2016/0108123, filed Oct. 13, 2015, entitled "Antibody Molecules to PD-L1 and Uses Thereof".

The components of the combination product are in the same formulation or in separate formulations.

In a preferred embodiment the combination product comprises a crystalline form according to any one of embodiments 1 to 7, and one or more immunotherapeutic agent useful in the treatment of cancer, specifically in immunotherapeutic treatment of cancer, such agent is selected from the group consisting of anti-PD-1 PD-1 antibodies such as MDX-1106, MK3475, CT-011, AMP-224 or an anti-PD-1 antibody molecule as described in WO2015/112900 (US2015/0210769); and anti-PD-L1 antibodies such as MPDL3280A, MEDI4736, MDX-1105 or an anti-PD-L1 antibody molecules are disclosed in US 2016/0108123.

Examples of Anti PD-1 Antibody Molecule

In a preferred embodiment, the combination product comprises a crystalline form according to any one of embodiments 1 to 7, and an anti-PD-1 antibody molecule such as those described herein.

PD-1 is a CD28/CTLA-4 family member expressed, e.g., on activated CD4+ and CD8+ T cells, $T_{regs}$, and B cells. It negatively regulates effector T cell signaling and function. PD-1 is induced on tumor-infiltrating T cells, and can result in functional exhaustion or dysfunction (Keir et al. (2008) Annu. Rev. Immunol. 26:677-704; Pardoll et al. (2012) Nat Rev Cancer 12(4):252-64). PD-1 delivers a coinhibitory signal upon binding to either of its two ligands, Programmed Death-Ligand 1 (PD-L1) or Programed Death-Ligand 2 (PD-L2). PD-L1 is expressed on a number of cell types, including T cells, Natural killer (NK) cells, macrophages, dendritic cells (DCs), B cells, epithelial cells, vascular endothelial cells, as well as many types of tumors. High expression of PD-L1 on murine and human tumors has been linked to poor clinical outcomes in a variety of cancers (Keir et al. (2008) Annu. Rev. Immunol. 26:677-704; Pardoll et al. (2012) Nat Rev Cancer 12(4):252-64). PD-L2 is expressed on dendritic cells, macrophages, and some tumors. Blockade of the PD-1 pathway has been pre-clinically and clinically validate for cancer immunotherapy. Both preclinical and clinical studies have demonstrated that anti-PD-1 blockade can restore activity of effector T cells and results in robust anti-tumor response. For example, blockade of PD-1 pathway can restore exhausted/dysfunctional effector T cell function (e.g. proliferation, IFN-g secretion, or cytolytic function) and/or inhibit $T_{reg}$ cell function (Keir et al. (2008) Annu. Rev. Immunol. 26:677-704; Pardoll et al. (2012) Nat Rev Cancer 12(4):252-64). Blockade of the PD-1 pathway can be effected with an antibody, an antigen binding fragment thereof, an immunoadhesin, a fusion protein, or oligopeptide of PD-1, PD-L and/or PD-L2.

In one embodiment, the PD-1 inhibitor is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In one embodiment, the anti-PD-1 antibody molecule comprises at least one, two, three, four, five or six complementarity determining regions (CDRs) (or collectively all of the CDRs) from a heavy and light chain variable region comprising an amino acid sequence shown in Table A (e.g., from the heavy and light chain variable region sequences of BAP049-Clone-E or BAP049-Clone-B disclosed in Table A), or encoded by a nucleotide sequence shown in Table A. In some embodiments, the CDRs are according to the Kabat definition (e.g., as set out in Table A). In some embodiments, the CDRs are according to the Chothia definition (e.g., as set out in Table A). In some embodiments, the CDRs are according to the combined CDR definitions of both Kabat and Chothia (e.g., as set out in Table A). In one embodiment, the combination of Kabat and Chothia CDR of VH CDR1 comprises the amino acid sequence GYTFTTYWMH (SEQ ID NO: 41). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table A, or encoded by a nucleotide sequence shown in Table A.

In one embodiment, the anti-PD-1 antibody molecule comprises a heavy chain variable region (VH) comprising a VHCDR1 amino acid sequence of SEQ ID NO: 1, a VHCDR2 amino acid sequence of SEQ ID NO: 2, and a VHCDR3 amino acid sequence of SEQ ID NO: 3; and a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 12, each disclosed in Table A.

In one embodiment, the antibody molecule comprises a VH comprising a VHCDR1 encoded by the nucleotide sequence of SEQ ID NO: 24, a VHCDR2 encoded by the nucleotide sequence of SEQ ID NO: 25, and a VHCDR3 encoded by the nucleotide sequence of SEQ ID NO: 26; and a VL comprising a VLCDR1 encoded by the nucleotide sequence of SEQ ID NO: 29, a VLCDR2 encoded by the nucleotide sequence of SEQ ID NO: 30, and a VLCDR3 encoded by the nucleotide sequence of SEQ ID NO: 31, each disclosed in Table A.

In one embodiment, the anti-PD-1 antibody molecule comprises a VH comprising the amino acid sequence of SEQ ID NO: 6, or an amino acid sequence at least 85%, 90%, 95%, or 99% identical or higher to SEQ ID NO: 6. In one embodiment, the anti-PD-1 antibody molecule comprises a VL comprising the amino acid sequence of SEQ ID NO: 20, or an amino acid sequence at least 85%, 90%, 95%, or 99% identical or higher to SEQ ID NO: 20. In one embodiment, the anti-PD-1 antibody molecule comprises a VL comprising the amino acid sequence of SEQ ID NO: 16, or an amino acid sequence at least 85%, 90%, 95%, or 99% identical or higher to SEQ ID NO: 16. In one embodiment, the anti-PD-1 antibody molecule comprises a VH comprising the amino acid sequence of SEQ ID NO: 6 and a VL comprising the amino acid sequence of SEQ ID NO: 20. In one embodiment, the anti-PD-1 antibody molecule comprises a VH comprising the amino acid sequence of SEQ ID NO: 6 and a VL comprising the amino acid sequence of SEQ ID NO: 16.

In one embodiment, the antibody molecule comprises a VH encoded by the nucleotide sequence of SEQ ID NO: 7, or a nucleotide sequence at least 85%, 90%, 95%, or 99% identical or higher to SEQ ID NO: 7. In one embodiment, the antibody molecule comprises a VL encoded by the nucleotide sequence of SEQ ID NO: 21 or 17, or a nucleotide sequence at least 85%, 90%, 95%, or 99% identical or higher to SEQ ID NO: 21 or 17. In one embodiment, the antibody molecule comprises a VH encoded by the nucleotide sequence of SEQ ID NO: 7 and a VL encoded by the nucleotide sequence of SEQ ID NO: 21 or 17.

In one embodiment, the anti-PD-1 antibody molecule comprises a heavy chain comprising the amino acid sequence of SEQ ID NO: 8, or an amino acid sequence at least 85%, 90%, 95%, or 99% identical or higher to SEQ ID NO: 8. In one embodiment, the anti-PD-1 antibody molecule comprises a light chain comprising the amino acid sequence of SEQ ID NO: 22, or an amino acid sequence at least 85%, 90%, 95%, or 99% identical or higher to SEQ ID NO: 22. In one embodiment, the anti-PD-1 antibody molecule comprises a light chain comprising the amino acid sequence of SEQ ID NO: 18, or an amino acid sequence at least 85%, 90%, 95%, or 99% identical or higher to SEQ ID NO: 18. In one embodiment, the anti-PD-1 antibody molecule comprises a heavy chain comprising the amino acid sequence of SEQ ID NO: 8 and a light chain comprising the amino acid sequence of SEQ ID NO: 22. In one embodiment, the anti-PD-1 antibody molecule comprises a heavy chain comprising the amino acid sequence of SEQ ID NO: 8 and a light chain comprising the amino acid sequence of SEQ ID NO: 18.

In one embodiment, the antibody molecule comprises a heavy chain encoded by the nucleotide sequence of SEQ ID NO: 9, or a nucleotide sequence at least 85%, 90%, 95%, or 99% identical or higher to SEQ ID NO: 9. In one embodiment, the antibody molecule comprises a light chain encoded by the nucleotide sequence of SEQ ID NO: 23 or 19, or a nucleotide sequence at least 85%, 90%, 95%, or 99% identical or higher to SEQ ID NO: 23 or 19. In one embodiment, the antibody molecule comprises a heavy chain encoded by the nucleotide sequence of SEQ ID NO: 9 and a light chain encoded by the nucleotide sequence of SEQ ID NO: 23 or 19.

The antibody molecules described herein can be made by vectors, host cells, and methods described in US 2015/0210769, incorporated by reference in its entirety.

Definitions

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia CDRs, e.g., described in Table A. In one embodiment, the following definitions are used for the anti-PD-1 antibody molecules described in Table A: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid molecule of the invention.

BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See www.ncbi.nlm-.nih.gov.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

TABLE A

Amino acid and nucleotide sequences of exemplary anti-PD-1 antibody molecules

BAP049-Clone-B HC

| | | |
|---|---|---|
| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 6 | VH | EVQLVQSGAEVKKPGESLRISCKGSG YTFTTYWMHWVRQATGQGLEWMG NIYPGTGGSNFDEKFKNRVTITADKS TSTAYMELSSLRSEDTAVYYCTRWT TGTGAYWGQGTTVTVSS |
| SEQ ID NO: 7 | DNA VH | GAGGTGCAGCTGGTGCAGTCAGGC GCCGAAGTGAAGAAGCCCGGCGAG TCACTGAGAATTAGCTGTAAAGGT TCAGGCTACACCTTCACTACCTACT GGATGCACTGGGTCCGCCAGGCTA CCGGTCAAGGCCTCGAGTGGATGG GTAATATCTACCCCGGCACCGGCG GCTCTAACTTCGACGAGAAGTTTA AGAATAGAGTGACTATCACCGCCG ATAAGTCTACTAGCACCGCCTATAT GGAACTGTCTAGCCTGAGATCAGA GGACACCGCCGTCTACTACTGCACT AGGTGGACTACCGGCACAGGCGCC TACTGGGGTCAAGGCACTACCGTG ACCGTGTCTAGC |
| SEQ ID NO: 8 | HC | EVQLVQSGAEVKKPGESLRISCKGSG YTFTTYWMHWVRQATGQGLEWMG NIYPGTGGSNEDEKFKNRVTITADKS TSTAYMELSSLRSEDTAVYYCTRWT |

TABLE A-continued

Amino acid and nucleotide sequences of exemplary
anti-PD-1 antibody molecules

|  |  |  |
|---|---|---|
|  |  | TGTGAYWGQGTTVTVSSASTKGPSV<br>FPLAPCSRSTSESTAALGCLVKDYFP<br>EPVTVSWNSGALTSGVHTFPAVLQS<br>SGLYSLSSVVTVPSSSLGTKTYTCNV<br>DHKPSNTKVDKRVESKYGPPCPPCP<br>APEFLGGPSVFLFPPKPKDTLMISRTP<br>EVTCVVVDVSQEDPEVQFNWYVDG<br>VEVHNAKTKPREEQFNSTYRVVSVL<br>TVLHQDWLNGKEYKCKVSNKGLPS<br>SIEKTISKAKGQPREPQVYTLPPSQEE<br>MTKNQVSLTCLVKGFYPSDIAVEWE<br>SNGQPENNYKTTPPVLDSDGSFFLYS<br>RLTVDKSRWQEGNVFSCSVMHEAL<br>HNHYTQKSLSLSLG |
| SEQ ID NO: 9 | DNA HC | GAGGTGCAGCTGGTGCAGTCAGGC<br>GCCGAAGTGAAGAAGCCCGGCGAG<br>TCACTGAGAATTAGCTGTAAAGGT<br>TCAGGCTACACCTTCACTACCTACT<br>GGATGCACTGGGTCCGCCAGGCTA<br>CCGGTCAAGGCCTCGAGTGGATGG<br>GTAATATCTACCCCGGCACCGGCG<br>GCTCTAACTTCGACGAGAAGTTTA<br>AGAATAGAGTGACTATCACCGCCG<br>ATAAGTCTACTAGCACCGCCTATAT<br>GGAACTGTCTAGCCTGAGATCAGA<br>GGACACCGCCGTCTACTACTGCACT<br>AGGTGGACTACCGGCACAGGCGCC<br>TACTGGGGTCAAGGCACTACCGTG<br>ACCGTGTCTAGCGCTAGCACTAAG<br>GGCCCGTCCGTGTTCCCCCTGGCAC<br>CTTGTAGCGGAGCACTAGCGAAT<br>CCACCGCTGCCCTCGGCTGCCTGGT<br>CAAGGATTACTTCCCGGAGCCCGT<br>GACCGTGTCCTGGAACAGCGGAGC<br>CCTGACCTCCGGAGTGCACACCTTC<br>CCCGCTGTGCTGCAGAGCTCCGGG<br>CTGTACTCGCTGTCGTCGGTGGTCA<br>CGGTGCCTTCATCTAGCCTGGGTAC<br>CAAGACCTACACTTGCAACGTGGA<br>CCACAAGCCTTCCAACACTAAGGT<br>GGACAAGCGCGTCGAATCGAAGTA<br>CGGCCCACCGTGCCCGCCTTGTCCC<br>GCGCCGGAGTTCCTCGGCGGTCCCT<br>CGGTCTTTCTGTTCCCACCGAAGCC<br>CAAGGACACTTTGATGATTTCCCGC<br>ACCCCTGAAGTGACATGCGTGGTC<br>GTGGACGTGTCACAGGAAGATCCG<br>GAGGTGCAGTTCAATTGGTACGTG<br>GATGGCGTCGAGGTGCACAACGCC<br>AAAACCAAGCCGAGGGAGGAGCA<br>GTTCAACTCCACTTACCGCGTCGTG<br>TCCGTGCTGACGGTGCTGCATCAG<br>GACTGGCTGAACGGGAAGGAGTAC<br>AAGTGCAAAGTGTCCAACAAGGGA<br>CTTCCTAGCTCAATCGAAAAGACC<br>ATCTCGAAAGCCAAGGGACAGCCC<br>CGGGAACCCCAAGTGTATACCCTG<br>CCACCGAGCCAGGAAGAAATGACT<br>AAGAACCAAGTCTCATTGACTTGC<br>CTTGTGAAGGGCTTCTACCCATCGG<br>ATATCGCCGTGGAATGGGAGTCCA<br>ACGGCCAGCCGGAAAACAACTACA<br>AGACCACCCCTCCGGTGCTGGACT<br>CAGACGGATCCTTCTTCCTCTACTC<br>GCGGCTGACCGTGGATAAGAGCAG<br>ATGGCAGGAGGGAAATGTGTTCAG<br>CTGTTCTGTGATGCATGAAGCCCTG<br>CACAACCACTACACTCAGAAGTCC<br>CTGTCCCTCTCCCTGGGA |

BAP049-Clone-B LC

| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 12 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |

TABLE A-continued

Amino acid and nucleotide sequences of exemplary anti-PD-1 antibody molecules

| SEQ ID NO: 15 (Chothia) | LCDR3 | DYSYPY |
| SEQ ID NO: 16 | VL | EIVLTQSPATLSLSPGERATLSCKSSQ SLLDSGNQKNFLTWYQQKPGKAPKL LIYWASTRESGVPSRFSGSGSGTDFT FTISSLQPEDIATYYCQNDYSYPYTFG QGTKVEIK |
| SEQ ID NO: 17 | DNA VL | GAGATCGTCCTGACTCAGTCACCC GCTACCCTGAGCCTGAGCCCTGGC GAGCGGGCTACACTGAGCTGTAAA TCTAGTCAGTCACTGCTGGATAGCG GTAATCAGAAGAACTTCCTGACCT GGTATCAGCAGAAGCCCGGTAAAG CCCCTAAGCTGCTGATCTACTGGGC CTCTACTAGAGAATCAGGCGTGCC CTCTAGGTTTAGCGGTAGCGGTAGT GGCACCGACTTCACCTTCACTATCT CTAGCCTGCAGCCCGAGGATATCG CTACCTACTACTGTCAGAACGACTA TAGCTACCCCTACACCTTCGGTCAA GGCACTAAGGTCGAGATTAAG |
| SEQ ID NO: 18 | LC | EIVLTQSPATLSLSPGERATLSCKSSQ SLLDSGNQKNFLTWYQQKPGKAPKL LIYWASTRESGVPSRFSGSGSGTDFT FTISSLQPEDIATYYCQNDYSYPYTFG QGTKVEIKRTVAAPSVFIFPPSDEQLK SGTASVVCLLNNFYPREAKVQWKV DNALQSGNSQESVTEQDSKDSTYSLS STLTLSKADYEKHKVYACEVTHQGL SSPVTKSFNRGEC |
| SEQ ID NO: 19 | DNA LC | GAGATCGTCCTGACTCAGTCACCC GCTACCCTGAGCCTGAGCCCTGGC GAGCGGGCTACACTGAGCTGTAAA TCTAGTCAGTCACTGCTGGATAGCG GTAATCAGAAGAACTTCCTGACCT GGTATCAGCAGAAGCCCGGTAAAG CCCCTAAGCTGCTGATCTACTGGGC CTCTACTAGAGAATCAGGCGTGCC CTCTAGGTTTAGCGGTAGCGGTAGT GGCACCGACTTCACCTTCACTATCT CTAGCCTGCAGCCCGAGGATATCG CTACCTACTACTGTCAGAACGACTA TAGCTACCCCTACACCTTCGGTCAA GGCACTAAGGTCGAGATTAAGCGT ACGGTGGCCGCTCCCAGCGTGTTC ATCTTCCCCCCCAGCGACGAGCAG CTGAAGAGCGGCACCGCCAGCGTG GTGTGCCTGCTGAACAACTTCTACC CCCGGGAGGCCAAGGTGCAGTGGA AGGTGGACAACGCCCTGCAGACG GCAACAGCCAGGAGAGCGTCACCG AGCAGGACAGCAAGGACTCCACCT ACAGCCTGAGCAGCACCCTGACCC TGAGCAAGGCCGACTACGAGAAGC ATAAGGTGTACGCCTGCGAGGTGA CCCACCAGGGCCTGTCCAGCCCCG TGACCAAGAGCTTCAACAGGGGCG AGTGC |

BAP049-Clone-E HC

| SEQ ID NO: 1 (Kabat) | HCDR1 | TYWMH |
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 6 | VH | EVQLVQSGAEVKKPGESLRISCKGSG YTFTTYWMHWVRQATGQGLEWMG NIYPGTGGSNFDEKFKNRVTITADKS TSTAYMELSSLRSEDTAVYYCTRWT TGTGAYWGQGTTVTVSS |
| SEQ ID NO: 7 | DNA VH | GAGGTGCAGCTGGTGCAGTCAGGC GCCGAAGTGAAGAAGCCCGGCGAG TCACTGAGAATTAGCTGTAAAGGT TCAGGCTACACCTTCACTACCTACT GGATGCACTGGGTCCGCCAGGCTA CCGGTCAAGGCCTCGAGTGGATGG |

TABLE A-continued

Amino acid and nucleotide sequences of exemplary anti-PD-1 antibody molecules

| | | |
|---|---|---|
| | | GTAATATCTACCCCGGCACCGGCG GCTCTAACTTCGACGAGAAGTTTA AGAATAGAGTGACTATCACCGCCG ATAAGTCTACTAGCACCGCCTATAT GGAACTGTCTAGCCTGAGATCAGA GGACACCGCCGTCTACTACTGCACT AGGTGGACTACCGGCACAGGCGCC TACTGGGGTCAAGGCACTACCGTG ACCGTGTCTAGC |
| SEQ ID NO: 8 | HC | EVQLVQSGAEVKKPGESLRISCKGSG YTFTTYWMHWVRQATGQGLEWMG NIYPGTGGSNFDEKFKNRVTITADKS TSTAYMELSSLRSEDTAVYYCTRWT TGTGAYWGQGTTVTVSSASTKGPSV FPLAPCSRSTSESTAALGCLVKDYFP EPVTVSWNSGALTSGVHTFPAVLQS SGLYSLSSVVTVPSSSLGTKTYTCNV DHKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKGLPS SIEKTISKAKGQPREPQVYTLPPSQEE MTKNQVSLTCLVKGFYPSDIAVEWE SNGQPENNYKTTPPVLDSDGSFFLYS RLTVDKSRWQEGNVFSCSVMHEAL HNHYTQKSLSLSLG |
| SEQ ID NO: 9 | DNA HC | GAGGTGCAGCTGGTGCAGTCAGGC GCCGAAGTGAAGAAGCCCGGCGAG TCACTGAGAATTAGCTGTAAAGGT TCAGGCTACACCTTCACTACCTACT GGATGCACTGGGTCCGCCAGGCTA CCGGTCAAGGCCTCGAGTGGATGG GTAATATCTACCCCGGCACCGGCG GCTCTAACTTCGACGAGAAGTTTA AGAATAGAGTGACTATCACCGCCG ATAAGTCTACTAGCACCGCCTATAT GGAACTGTCTAGCCTGAGATCAGA GGACACCGCCGTCTACTACTGCACT AGGTGGACTACCGGCACAGGCGCC TACTGGGGTCAAGGCACTACCGTG ACCGTGTCTAGCGCTAGCACTAAG GGCCCGTCCGTGTTCCCCCTGGCAC CTTGTAGCCGGAGCACTAGCGAAT CCACCGCTGCCCTCGGCTGCCTGGT CAAGGATTACTTCCCGGAGCCCGT GACCGTGTCCTGGAACAGCGGAGC CCTGACCTCCGGAGTGCACACCTTC CCCGCTGTGCTGCAGAGCTCCGGG CTGTACTCGCTGTCGTCGGTGGTCA CGGTGCCTTCATCTAGCCTGGGTAC CAAGACCTACACTTGCAACGTGGA CCACAAGCCTTCCAACACTAAGGT GGACAAGCGCGTCGAATCGAAGTA CGGCCCACCGTGCCCGCCTTGTCCC GCGCCGGAGTTCCTCGGCGGTCCCT CGGTCTTTCTGTTCCCACCGAAGCC CAAGGACACTTTGATGATTTCCCGC ACCCCTGAAGTGACATGCGTGGTC GTGGACGTGTCACAGGAAGATCCG GAGGTGCAGTTCAATTGGTACGTG GATGGCGTCGAGGTGCACAACGCC AAAACCAAGCCGAGGGAGGAGCA GTTCAACTCCACTTACCGCGTCGTG TCCGTGCTGACGGTGCTGCATCAG GACTGGCTGAACGGGAAGGAGTAC AAGTGCAAAGTGTCCAACAAGGGA CTTCCTAGCTCAATCGAAAAGACC ATCTCGAAAGCCAAGGGACAGCCC CGGGAACCCCAAGTGTATACCCTG CCACCGAGCCAGGAAGAAATGACT AAGAACCAAGTCTCATTGACTTGC CTTGTGAAGGGCTTCTACCCATCGG ATATCGCCGTGGAATGGGAGTCCA ACGGCCAGCCGGAAAACAACTACA AGACCACCCCTCCGGTGCTGGACT CAGACGGATCCTTCTTCCTCTACTC |

TABLE A-continued

Amino acid and nucleotide sequences of exemplary
anti-PD-1 antibody molecules

|  |  |  |
|---|---|---|
|  |  | GCGGCTGACCGTGGATAAGAGCAG |
|  |  | ATGGCAGGAGGGAAATGTGTTCAG |
|  |  | CTGTTCTGTGATGCATGAAGCCCTG |
|  |  | CACAACCACTACACTCAGAAGTCC |
|  |  | CTGTCCCTCTCCCTGGGA |

BAP049-Clone-E LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 12 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPY |
| SEQ ID NO: 20 | VL | EIVLTQSPATLSLSPGERATLSCKSSQ SLLDSGNQKNFLTWYQQKPGQAPRL LIYVVASTRESGVPSRFSGSGSGTDFT FTISSLEAEDAATYYCQNDYSYPYTF GQGTKVEIK |
| SEQ ID NO: 21 | DNA VL | GAGATCGTCCTGACTCAGTCACCC GCTACCCTGAGCCTGAGCCCTGGC GAGCGGGCTACACTGAGCTGTAAA TCTAGTCAGTCACTGCTGGATAGCG GTAATCAGAAGAACTTCCTGACCT GGTATCAGCAGAAGCCCGGTCAAG CCCCTAGACTGCTGATCTACTGGGC CTCTACTAGAGAATCAGGCGTGCC CTCTAGGTTTAGCGGTAGCGGTAGT GGCACCGACTTCACCTTCACTATCT CTAGCCTGGAAGCCGAGGACGCCG CTACCTACTACTGTCAGAACGACTA TAGCTACCCCTACACCTTCGGTCAA GGCACTAAGGTCGAGATTAAG |
| SEQ ID NO: 22 | LC | EIVLTQSPATLSLSPGERATLSCKSSQ SLLDSGNQKNFLTWYQQKPGQAPRL LIYVVASTRESGVPSRFSGSGSGTDFT FTISSLEAEDAATYYCQNDYSYPYTF GQGTKVEIKRTVAAPSVFIFPPSDEQL KSGTASVVCLLNNFYPREAKVQWK VDNALQSGNSQESVTEQDSKDSTYS LSSTLTLSKADYEKHKVYACEVTHQ GLSSPVTKSFNRGEC |
| SEQ ID NO: 23 | DNA LC | GAGATCGTCCTGACTCAGTCACCC GCTACCCTGAGCCTGAGCCCTGGC GAGCGGGCTACACTGAGCTGTAAA TCTAGTCAGTCACTGCTGGATAGCG GTAATCAGAAGAACTTCCTGACCT GGTATCAGCAGAAGCCCGGTCAAG CCCCTAGACTGCTGATCTACTGCTGC CTCTACTAGAGAATCAGGCGTGCC CTCTAGGTTTAGCGGTAGCGGTAGT GGCACCGACTTCACCTTCACTATCT CTAGCCTGGAAGCCGAGGACGCCG CTACCTACTACTGTCAGAACGACTA TAGCTACCCCTACACCTTCGGTCAA GGCACTAAGGTCGAGATTAAGCGT ACGGTGGCCGCTCCCAGCGTGTTC ATCTTCCCCCCCAGCGACGAGCAG CTGAAGAGCGGCACCGCCAGCGTG GTGTGCCTGCTGAACAACTTCTACC CCCGGGAGGCCAAGGTGCAGTGGA AGGTGGACAACGCCCTGCAGAGCG GCAACAGCCAGGAGAGCGTCACCG AGCAGGACAGCAAGGACTCCACCT ACAGCCTGAGCAGCACCCTGACCC TGAGCAAGGCCGACTACGAGAAGC ATAAGGTGTACGCCTGCGAGGTGA CCCACCAGGGCCTGTCCAGCCCCG TGACCAAGAGCTTCAACAGGGGCG AGTGC |

BAP049-Clone-B HC

| SEQ ID NO: 24 (Kabat) | HCDR1 | ACCTACTGGATGCAC |
|---|---|---|
| SEQ ID NO: 25 (Kabat) | HCDR2 | AATATCTACCCCGGCACCGGCGG TCTAACTTCGACGAGAAGTTTAAG AAT |

TABLE A-continued

Amino acid and nucleotide sequences of exemplary anti-PD-1 antibody molecules

| | | | |
|---|---|---|---|
| SEQ ID NO: 26 | (Kabat) | HCDR3 | TGGACTACCGGCACAGGCGCCTAC |
| SEQ ID NO: 27 | (Chothia) | HCDR1 | GGCTACACCTTCACTACCTAC |
| SEQ ID NO: 28 | (Chothia) | HCDR2 | TACCCCGGCACCGGCGGC |
| SEQ ID NO: 26 | (Chothia) | HCDR3 | TGGACTACCGGCACAGGCGCCTAC |

BAP049-Clone-B LC

| | | | |
|---|---|---|---|
| SEQ ID NO: 29 | (Kabat) | LCDR1 | AAATCTAGTCAGTCACTGCTGGATAGCGGTAATCAGAAGAACTTCCTGACC |
| SEQ ID NO: 30 | (Kabat) | LCDR2 | TGGGCCTCTACTAGAGAATCA |
| SEQ ID NO: 31 | (Kabat) | LCDR3 | CAGAACGACTATAGCTACCCCTACACC |
| SEQ ID NO: 32 | (Chothia) | LCDR1 | AGTCAGTCACTGCTGGATAGCGGTAATCAGAAGAACTTC |
| SEQ ID NO: 33 | (Chothia) | LCDR2 | TGGGCCTCT |
| SEQ ID NO: 34 | (Chothia) | LCDR3 | GACTATAGCTACCCCTAC |

BAP049-Clone-E HC

| | | | |
|---|---|---|---|
| SEQ ID NO: 24 | (Kabat) | HCDR1 | ACCTACTGGATGCAC |
| SEQ ID NO: 25 | (Kabat) | HCDR2 | AATATCTACCCCGGCACCGGCGGCTCTAACTTCGACGAGAAGTTTAAGAAT |
| SEQ ID NO: 26 | (Kabat) | HCDR3 | TGGACTACCGGCACAGGCGCCTAC |
| SEQ ID NO: 27 | (Chothia) | HCDR1 | GGCTACACCTTCACTACCTAC |
| SEQ ID NO: 28 | (Chothia) | HCDR2 | TACCCCGGCACCGGCGGC |
| SEQ ID NO: 26 | (Chothia) | HCDR3 | TGGACTACCGGCACAGGCGCCTAC |

BAP049-Clone-E LC

| | | | |
|---|---|---|---|
| SEQ ID NO: 29 | (Kabat) | LCDR1 | AAATCTAGTCAGTCACTGCTGGATAGCGGTAATCAGAAGAACTTCCTGACC |
| SEQ ID NO: 30 | (Kabat) | LCDR2 | TGGGCCTCTACTAGAGAATCA |
| SEQ ID NO: 31 | (Kabat) | LCDR3 | CAGAACGACTATAGCTACCCCTACACC |
| SEQ ID NO: 32 | (Chothia) | LCDR1 | AGTCAGTCACTGCTGGATAGCGGTAATCAGAAGAACTTC |
| SEQ ID NO: 33 | (Chothia) | LCDR2 | TGGGCCTCT |
| SEQ ID NO: 34 | (Chothia) | LCDR3 | GACTATAGCTACCCCTAC |

Other Exemplary PD-1 Inhibitors

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab, e.g., as disclosed in Table B.

In one embodiment, the anti-PD-1 antibody molecule is Pembrolizumab (Merck & Co), also known as Lambrolizumab, MK-3475, MK03475, SCH-900475, or KEYTRUDA®. Pembrolizumab and other anti-PD-1 antibodies are disclosed in Hamid, O. et al. (2013) New England Journal of Medicine 369 (2): 134-44, U.S. Pat. No. 8,354,509, and WO 2009/114335, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab, e.g., as disclosed in Table B.

In one embodiment, the anti-PD-1 antibody molecule is Pidilizumab (CureTech), also known as CT-011. Pidilizumab and other anti-PD-1 antibodies are disclosed in Rosenblatt, J. et al. (2011) J Immunotherapy 34(5): 409-18, U.S. Pat. Nos. 7,695,715, 7,332,582, and 8,686,119, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab, e.g., as disclosed in Table B.

In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of MEDI0680.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

TABLE B

Amino acid sequences of other exemplary anti-PD-1 antibody molecules

Nivolumab

| SEQ ID NO: 35 | HC | QVQLVESGGGVVQPGRSLRLDCKAS GITFSNSGMHWVRQAPGKGLEWVA VIWYDGSKRYYADSVKGRFTISRDN SKNTLFLQMNSLRAEDTAVYYCATN DDYWGQGTLVTVSSASTKGPSVFPL APCSRSTSESTAALGCLVKDYFPEPV TVSWNSGALTSGVHTFPAVLQSSGL YSLSSVVTVPSSSLGTKTYTCNVDHK PSNTKVDKRVESKYGPPCPPCPAPEF LGGPSVFLFPPKPKDTLMISRTPEVTC VVVDVSQEDPEVQFNWYVDGVEVH NAKTKPREEQFNSTYRVVSVLTVLH QDWLNGKEYKCKVSNKGLPSSIEKTI SKAKGQPREPQVYTLPPSQEEMTKN QVSLTCLVKGFYPSDIAVEWESNGQ PENNYKTTPPVLDSDGSFFLYSRLTV DKSRWQEGNVFSCSVMHEALHNHY TQKSLSLSLGK |
| SEQ ID NO: 36 | LC | EIVLTQSPATLSLSPGERATLSCRASQ SVSSYLAWYQQKPGQAPRLLIYDAS NRATGIPARFSGSGSGTDFTLTISSLE PEDFAVYYCQQSSNWPRTFGQGTKV EIKRTVAAPSVFIFPPSDEQLKSGTAS VVCLLNNFYPREAKVQWKVDNALQ SGNSQESVfTEQDSKDSTYSLSSTLTL SKADYEKHKVYACEVTHQGLSSPVT KSFNRGEC |

Pembrolizumab

| SEQ ID NO: 37 | HC | QVQLVQSGVEVKKPGASVKVSCKAS GYTFTNYYMYWVRQAPGQGLEWM GGINPSNGGTNFNEKFKNRVTLTTDS STTTAYMELKSLQFDDTAVYYCARR DYRFDMGFDYWGQGTTVTVSSAST KGPSVFPLAPCSRSTSESTAALGCLV KDYFPEPVTVSWNSGALTSGVHTFP AVLQSSGLYSLSSVVTVPSSSLGTKT YTCNVDHKPSNTKVDKRVESKYGPP CPPCPAPEFLGGPSVFLFPPKPKDTL MISRTPEVTCVVVDVSQEDPEVQFN WYVDGVEVHNAKTKPREEQFNSTY RVVSVLTVLHQDWLNGKEYKCKVS NKGLPSSIEKTISKAKGQPREPQVYT LPPSQEEMTKNQVSLTCLVKGFYPSD IAVEWESNGQPENNYKTTPPVLDSD GSFFLYSRLTVDKSRWQEGNVFSCS VMHEALHNHYTQKSLSLSLGK |
| SEQ ID NO: 38 | LC | EIVLTQSPATLSLSPGERATLSCRASK GVSTSGYSYLHWYQQKPGQAPRLLI YLASYLESGVPARFSGSGSGTDFTLTI SSLEPEDFAVYYCQHSRDLPLTFGGG TKVEIKRTVAAPSVFIFPPSDEQLKSG TASVVCLLNNFYPREAKVQWKVDN ALQSGNSQESVTEQDSKDSTYSLSST LTLSKADYEKHKVYACEVTHQGLSS PVTKSFNRGEC |

TABLE B-continued

Amino acid sequences of other exemplary anti-PD-1 antibody molecules

Pidilizumab

| SEQ ID NO: 39 | HC | QVQLVQSGSELKKPGASVKISCKAS GYTFTNYGMNWVRQAPGQGLQWM GWINTDSGESTYAEEFKGRFVFSLDT SVNTAYLQITSLTAEDTGMYFCVRV GYDALDYWGQGTLVTVSSASTKGPS VFPLAPSSKSTSGGTAALGCLVKDYF PEPVTVSWNSGALTSGVHTFPAVLQ SSGLYSLSSVVTVPSSSLGTQTYICNV NHKPSNTKVDKRVEPKSCDKTHTCP PCPAPELLGGPSVFLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFF LYSKLTVDKSRWQQGNVESCSVMH EALHNHYTQKSLSLSPGK |
| SEQ ID NO: 40 | LC | EIVLTQSPSSLSASVGDRVTITCSARS SVSYMHWFQQKPGKAPKLWIYRTS NLASGVPSRFSGSGSGTSYCLTINSLQ PEDFATYYCQQRSSFPLTFGGGTKLE IKRTVAAPSVFIFPPSDEQLKSGTASV VCLLNNFYPREAKVQWKVDNALQS GNSQESVIEQDSKDSTYSLSSTLTLS KADYEKHKVYACEVTHQGLSSPVTK SFNRGEC |

Example of Anti PD-L1 Antibody Molecule

In one embodiment, the combination product comprises a crystalline form according to any one of embodiments 1 to 7, and an anti-PD-L1 antibody molecule such as those described herein.

Programmed Death Ligand 1 (PD-L1) has been described as a ligand for the immunoinhibitory receptor Programmed Death 1 (PD-1). Binding of PD-L1 to PD-1 leads to the inhibition of T cell receptor-mediated lymphocyte proliferation and cytokine secretion (Freeman et al. (2000) *J Exp Med* 192:1027-34). Thus, blocking of PD-L1 can lead to enhancement of antitumor immunity.

Several cell types express PD-L1. For example, PD-L1 is expressed on activated T cells, dendritic cells (DCs), natural killer (NK) cells, macrophages, B cells, monocytes, and vascular endothelium cells. PD-L1 is expressed in many cancers, including human lung, ovarian and colon carcinoma and various myelomas, (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 expression strongly correlates with unfavorable prognosis in various types of cancer including kidney, ovarian, bladder, breast, gastric and pancreatic cancer.

Many tumor infiltrating T lymphocytes predominantly express PD-1 compared to T lymphocytes in normal tissues and peripheral blood T lymphocytes. This indicates that up-regulation of PD-1 on tumor-reactive T cells can contribute to impaired antitumor immune responses (Ahmadzadeh et al. (2009) *Blood* 114:1537-44). Thus, PD-L1 signaling mediated by PD-L1 expressing tumor cells interacting with PD-1 expressing T cells may lead to attenuation of T cell activation and evasion of immune surveillance (Sharpe et al. (2002) *Nat Rev Imnunol.* 2:116-26; Keir et al. (2008) *Annu Rev Immunol.* 26:677-704). PD-1 blockade can inhibit hematogenous spread of poorly immunogenic tumor cells by enhanced recruitment of effector T cells (Iwai et al. (2005) *Int. Immunol.* 17:133-144).

Anti-PD-L1 can enhance T-cell immunity, e.g., through blocking both its inhibitory interactions with PD-1 and B7-1. Anti-PD-1 can also allow for immune regulation via PD-L2/PD-1. Both PD-1 and B7-1 are expressed on T cells, B cells, DCs, and macrophages, which provides potential for bidirectional interactions between B7-1 and PD-L1 on these cell types. PD-L1 on non-hematopoietic cells may interact with B7-1 as well as PD-1 on T cells.

In some embodiments, the anti-PD-L1 antibody molecule is chosen from YW243.55.S70, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain (SEQ ID NO: 24 as disclosed in WO2013/
079174)
                                         (SEQ ID NO: 42)
EVQLLESGGGLVQPGGSLRLSCAASGFTFSSYIMMWVRQAPGKGLEWVSSI

YPSGGITFYADKGRFTISRDNSKNTLYLQMNSLRAEDTAVYYCARIKLGTV

TTVDYWGQGTLVTVSS

Light chain (SEQ ID NO: 25 as disclosed in WO2013/
079174)
                                         (SEQ ID NO: 43)
QSALTQPASVSGSPGQSITISCTGTSSDVGGYNYVSWYQQHPGKAPKLMIY

DVSNRPSGVSNRFSGSKSGNTASLTISGLQAEDEADYYCSSYTSSSTRVFG

TGTKVTVL
```

In one embodiment, the PD-L1 inhibitor is YW243.55.S70. The YW243.55.S70 antibody is an anti-PD-L1 described in WO 2010/077634 (heavy and light chain variable region sequences shown in SEQ ID NOs. 20 and 21, respectively), and having a sequence disclosed therein (or a sequence substantially identical or similar thereto, e.g., a sequence at least 85%, 90%, 95% identical or higher to the sequence specified).

In one embodiment, the PD-L inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906.

In another embodiment, the PD-L1 inhibitor is an anti-PD-L antibody molecule disclosed in US 2016/0108123, filed Oct. 13, 2015, entitled "Antibody Molecules to PD-L1 and Uses Thereof," incorporated by reference in its entirety.

In one embodiment, the anti-PD-L1 antibody molecule includes at least one or two heavy chain variable domains (optionally including a constant region), at least one or two light chain variable domains (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 of US 2016/0108123; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123.

In one embodiment, the anti-PD-L1 antibody molecule includes at least one, two or three CDRs or hypervariable loops from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, according to the Kabat and Chothia definition (e.g., at least one, two or three CDRs or hypervariable loops according to the Kabat and Chothia definition as set out in Table 1 of US 2016/0108123); or encoded by the nucleotide sequence in Table 1 of US 2016/0108123; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1 of US 2016/0108123.

In one embodiment, the anti-PD-L1 antibody molecule can include VH CDR according to Kabat et al. ((1991), "Sequences of Proteins of Immunological Interest," 5th Ed. Public Health Service, National Institutes of Health, Bethesda, Md.) or VH hypervariable loop 1 according to Chothia et al. (1992) *J. Mot. Biol.* 227:799-817, or a combination thereof, e.g., as shown in Table 1 of US 2016/0108123. In one embodiment, the combination of Kabat and Chothia CDR of VH CDR1 comprises the amino acid sequence GYTFTSYWMY (SEQ ID NO: 63), or an amino acid sequence substantially identical thereto (e.g., having at least one amino acid alteration, but not more than two, three or four alterations (e.g., substitutions, deletions, or insertions, e.g., conservative substitutions)). The anti-PD-L1 antibody molecule can further include, e.g., VH CDRs 2-3 according to Kabat et al. and VL CDRs 1-3 according to Kabat et al., e.g., as shown in Table 1 of US 2016/0108123.

In a preferred embodiment, the anti PD-L1 antibody molecule for use in the invention comprises:

(a) a heavy chain variable region (VH) comprising a VHCDR1 amino acid sequence of SEQ ID NO: 47, a VHCDR2 amino acid sequence of SEQ ID NO: 48, and a VHCDR3 amino acid sequence of SEQ ID NO: 46; and a light chain variable region (VL) comprising a VLCDR1 amino acid sequence of SEQ ID NO: 52, a VLCDR2 amino acid sequence of SEQ ID NO: 53, and a VLCDR3 amino acid sequence of SEQ ID NO: 54;

(b) a VH comprising a VHCDR1 amino acid sequence of SEQ ID NO: 44; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51;

(c) a VH comprising a VHCDR1 amino acid sequence of SEQ ID NO: 63, a VHCDR2 amino acid sequence of SEQ ID NO: 48, and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54; or (d) a VH comprising a VHCDR1 amino acid sequence of SEQ ID NO: 63; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54.

In one aspect of the previous embodiment, the anti-PD-L1 antibody molecule for use in the invention comprises a heavy chain variable domain comprising the amino acid sequence of SEQ ID NO: 55 and a light chain variable domain comprising the amino acid sequence of SEQ ID NO: 58.

In one aspect of the previous embodiment, the anti-PD-L1 antibody molecule for use in the invention comprises a heavy chain comprising the amino acid sequence of SEQ ID NO: 62 and a light chain comprising the amino acid sequence of SEQ ID NO: 60. Table C. Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

TABLE C

BAP058-hum13-HC

| | | |
|---|---|---|
| SEQ ID NO: 63 (Chothia and Kabat combined) | HCDR1 | GYTFTSYWMY |
| SEQ ID NO: 44 (Kabat) | HCDR1 | SYWMY |
| SEQ ID NO: 45 (Kabat) | HCDR2 | RIDPNSGSTKYNEKFKN |
| SEQ ID NO: 46 (Kabat) | HCDR3 | DYRKGLYAMDY |
| SEQ ID NO: 47 (Chothia) | HCDR1 | GYTFTSY |
| SEQ ID NO: 48 (Chothia) | HCDR2 | DPNSGS |
| SEQ ID NO: 46 (Chothia) | HCDR3 | DYRKGLYA1VIDY |
| SEQ ID NO: 55 | VH | EVQLVQSGAEVKKPGATVKISCKVSGYTFTSYWMYMVRQARGQRLEWIGRIDPNSGSTKYNEKFKNRFTISRDNSKNTLYLQMNSLRAEDTAVYYCARDYRKGLYAMDYWGQGTTVTVSS |
| SEQ ID NO: 56 | DNA VH | GAGGTCCAGCTGGTACAGTCTGGGGCTGAGGTGAAGAAGCCTGGGGCTACAGTGAAAATCTCCTGCAAGGTTTCTGGCTACACCTTCACCAGTTACTGGATGTACTGGGTGCGACAGGCTCGTGGACAACGCCTTGAGTGGATAGGTAGGATTGATCCTAATAGTGGGAGTACTAAGTACAATGAGAAGTTCAAGAACAGATTCACCATCTCCAGAGACAATTCCAAGAACACGCTGTATCTTCAAATGAACAGCCTGAGAGCCGAGG |

TABLE C-continued

| | | |
|---|---|---|
| | | ACACGGCCGTGTATTACTGTGCAAGGG ACTATAGAAAGGGGCTCTATGCTATGG ACTACTGGCTGCCAGCTGCACCACCGTGA CCGTGTCCTCC |
| SEQ ID NO: 62 | Heavy Chain | EVQLVQSGAEVKKPGATVKISCKVSGYT FTSYWMYWVRQARGQRLEWIGRIDPNS GSTKYNEKFKNRFTISRDNSKNTLYLQM NSLRAEDTAVYYCARDYRKGLYAMDY WGQGTTVTVSSASTKGPSVFPLAPCSRST SESTAALGCLVKDYFPEPVTVSWNSGAL TSGVHTFPAVLQSSGLYSLSSVVTVPSSS LGTKTYTCNVDHKPSNTKVDKRVESKY GPPCPPCPAPEFLGGPSVFLFPPKPKDTL MISRTPEVTCVVVDVSQEDPEVQFNWYV DGVEVHNAKTKPREEQFNSTYRVVSVLT VLHQDWLNGKEYKCKVSNKGLPSSIEKT ISKAKGQPREPQVYTLPPSQEEMTKNQV SLTCLVKGFYPSDIAVEWESNGQPENNY KTTPPVLDSDGSFFLYSRLTVDKSRWQE GNVFSCSVMHEALHNHYTQKSLSLSLGK |
| SEQ ID NO: 57 | DNA Heavy Chain | GAGGTCCAGCTGGTACAGTCTGGGGCT GAGGTGAAGAAGCCTGGGGCTACAGT GAAAATCTCCTGCAAGGTTTCTGGCTA CACCTTCACCAGTTACTGGATGTACTG GGTGCGACAGGCTCGTGGACAACCCT TGAGTGGATAGGTAGGATTGATCCTAA TAGTGGGAGTACTAAGTACAATGAGAA GTTTCAAGAACAGATTCACCATCTCCAG AGACAATTCCAAGAACACGCTGTATCT TCAAATGAACAGCCTGAGAGCCGAGG ACACGGCCGTGTATTACTGTGCAAGGG ACTATAGAAAGGGGCTCTATGCTATGG ACTACTGGGGCCAGGGCACCACCGTGA CCGTGTCCTCCGCTTCCACCAAGGGCC CATCCGTCTTCCCCCTGGCGCCCTGCTC CAGGAGCACCTCCGAGAGCACAGCCGC CCTGCTGCTGCTGGTCAAGGACTACTT CCCCGAACCGGTGACGGTGTCGTGGAA CTCAGGCGCCCTGACCAGCGGCGTGCA CACCTTCCCGGCTGTCCTACAGTCCTCA GGACTCTACTCCCTCAGCAGCGTGGTG ACCGTGCCCTCCAGCAGCTTGGGCACG AAGACCTACACCTGCAACGTAGATCAC AAGCCCAGCAACACCAAGGTGGACAA GAGAGTTGAGTCCAAATATGGTCCCCC ATGCCCACCGTGCCCAGCACCTGAGTT CCTGGGGGGACCATCAGTCTTCCTGTT CCCCCCAAAACCCAAGGACACTCTCAT GATCTCCCGGACCCCTGAGGTCACGTG CGTGGTGGTGGACGTGAGCCAGGAAG ACCCCGAGGTCCAGTTCAACTGGTACG TGGATGGCGTGGAGGTGCATAATGCCA AGACAAAGCCGCGGGAGGAGCAGTTC AACAGCACGTACCGTGTGGTCAGCGTC CTCACCGTCCTGCACCAGGACTGGCTG AACGGCAAGGAGTACAAGTGCAAGGT GTCCAACAAAGGCCTCCCGTCCTCCAT CGAGAAAACCATCTCCAAAGCCAAAG GGCAGCCCCGAGAGCCACAGGTGTACA CCCTGCCCCCATCCCAGGAGGAGATGA CCAAGAACCAGGTCAGCCTGACCTGCC TGGTCAAAGGCTTCTACCCCAGCGACA TCGCCGTGGAGTGGGAGAGCAATGGGC AGCCGGAGAACAACTACAAGACCACG CCTCCCGTGCTGGACTCCGACGGCTCC TTCTTCCTCTACAGCAGGCTAACCGTG GACAAGAGCAGGTGGCAGGAGGGGAA TGTCTTCTCATGCTCCGTGATGCATGAG GCTCTGCACAACCACTACACACAGAAG AGCCTCTCCCTGTCTCTGGGTAAA |

BAP058-hum13-LC

| | | |
|---|---|---|
| SEQ ID NO: 49 (Kabat) | LCDR1 | KASQDVGTAVA |
| SEQ ID NO: 50 (Kabat) | LCDR2 | WASTRHT |
| SEQ ID NO: 51 (Kabat) | LCDR3 | QQYNSYPLT |
| SEQ ID NO: 52 (Chothia) | LCDR1 | SQDVGTA |
| SEQ ID NO: 53 (Chothia) | LCDR2 | WAS |
| SEQ ID NO: 54 (Chothia) | LCDR3 | YNSYPL |
| SEQ ID NO: 58 | VL | AIQLTQSPSSLSASVGDRVTITCKASQDV |

TABLE C-continued

| | | |
|---|---|---|
| SEQ ID NO: 59 | DNA VL | GTAVAWYLQKPGQSPQLLIYWASTRHT GVPSRFSGSGSGTDFTFTISSLEAEDAATY YCQQYNSYPLTFGQGTKVEIK GCCATCCAGTTGACCCAGTCTCCATCCT CCCTGTCTGCATCTGTAGGAGACAGAG TCACCATCACTTGCAAGGCCAGTCAGG ATGTGGGTACTGCTGTAGCCTGGTACC TGCAGAAGCCAGGGCAGTCTCCACAGC TCCTGATCTATTGGGCATCCACCCGGC ACACTGGGGTCCCCTCGAGGTTCAGTG GCAGTGGATCTGGGACAGATTTCACCT TTACCATCAGTAGCCTGGAAGCTGAAG ATGCTGCAACATATTACTGTCAGCAGT ATAACAGCTATCCTCTCACGTTCGGCC AAGGGACCAAGGTGGAAATCAAA |
| SEQ ID NO: 60 | Light Chain | AIQLTQSPSSLSASVGDRVTITCKASQDV GTAVAWYLQKPGQSPQLLIYWASTRHT GVPSRFSGSGSGTDFTFTISSLEAEDAATY YCQQYNSYPLTFGQGTKVEIKRTVAAPS VFIFPPSDEQLKSGTASVVCLLNNFYPRE AKVQWKVDNALQSGNSQESVTEQDSKD STYSLSSTLTLSKADYEKHKVYACEVTH QGLSSPVTKSFNRGEC |
| SEQ ID NO: 61 | DNA Light Chain | GCCATCCAGTTGACCCAGTCTCCATCCT CCCTGTCTGCATCTGTAGGAGACAGAG TCACCATCACTTGCAAGGCCAGTCAGG ATGTGGGTACTGCTGTAGCCTGGTACC TGCAGAAGCCAGGGCAGTCTCCACAGC TCCTGATCTATTGGGCATCCACCCGGC ACACTGGGGTCCCCTCGAGGTTCAGTG GCAGTGGATCTGGGACAGATTTCACCT TTACCATCAGTAGCCTGGAAGCTGAAG ATGCTGCAACATATTACTGTCAGCAGT ATAACAGCTATCCTCTCACGTTCGGCC AAGGGACCAAGGTGGAAATCAAACGT ACGGTGGCTGCACCATCTGTCTTCATCT TCCCGCCATCTGATGAGCAGTTGAAAT CTGGAACTGCCTCTGTTGTGTGCCTGCT GAATAACTTCTATCCCAGAGAGGCCAA AGTACAGTGGAAGGTGGATAACGCCCT CCAATCGGGTAACTCCCAGGAGAGTGT CACAGAGCAGGACAGCAAGGACAGCA CCTACAGCCTCAGCAGCACCCTGACGC TGAGCAAAGCAGACTACGAGAAACAC AAAGTCTACGCCTGCGAAGTCACCCAT CAGGGCCTGAGCTCGCCCGTCACAAAG AGCTTCAACAGGGGAGAGTGT |

Dosage and Administration of the Immunotherapeutic Agent.

The immunotherapeutic agent (Such as an anti-PD-1 antibody molecule or an anti-PD-L1 molecule antibody) can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the immunotherapeutic agent (e.g. anti-PD-1 antibody molecule or anti PD-L1 antibody molecule) can be determined by a skilled artisan. In certain embodiments, the immunotherapeutic agent (e.g. anti-PD-1 antibody molecule) is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week. In another embodiment, the anti-PD-1 antibody molecule is administered at a dose from about 1 to 10 mg/Kg, or from about 1 to 5 mg/Kg or about 3 mg/kg every 4 weeks.

For example, the anti-PD-1 antibody molecule is administered or used at a flat or fixed dose. In some embodiments, the anti-PD-1 antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. The dosing schedule (e.g., flat dosing schedule) can vary from e.g., once a week to once every 2, 3, 4, 5, or 6 weeks. In one embodiment, the anti-PD-1 antibody molecule is administered at a dose from about 300 mg to 400 mg once every three weeks or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

In another embodiment, the anti-PD-1 antibody molecule is administered at a flat dose of about 300 mg to 400 mg once every three weeks or once every four weeks. In a subset of this embodiment, the anti-PD-1 antibody molecule is administered at a flat dose of about 400 mg every four weeks. In yet another subset of this embodiment, the anti-PD-1 antibody molecule is administered at a flat dose of about 300 mg every three weeks.

Preparation of Crystalline Form of

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. Exemplary methods of preparing the crystalline forms described herein are set forth in detail below.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvents, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature. This may also be referred to as a suspension.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971,26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Alternatively, crystalline forms may be prepared directly from the reaction medium of the final process for preparing 5-bromo-2,6-di(1H-pyrazol-1-yl)pyrimidin-4-amine. This may be achieved, for example, by employing in the final process step a solvent or a mixture of solvents from which 5-bromo-2,6-di(1H-pyrazol-1-yl)pyrimidin-4-amine or salt thereof may be crystallized. In addition, crystalline forms may be obtained by distillation or solvent addition techniques.

In addition to the methods discussed briefly below, it should be understood that various analytical methods may be used for the characterization of any of the materials described herein.

The following non-limiting examples are illustrative of the disclosure.

EXAMPLES

The various crystalline forms of 5-bromo-2,6-di(1H-pyrazol-1-yl)pyrimidin-4-amine described herein were prepared as follows. It should be understood that these examples are illustrative and that these materials may be prepared according to other methods described herein or via methods known in the art.

(Form F) Free Form 5-bromo-2,6-di(1H-pyrazol-1-yl)pyrimidin-4-amine (Modification 1)

The solid was analyzed by XRPD after isolation.

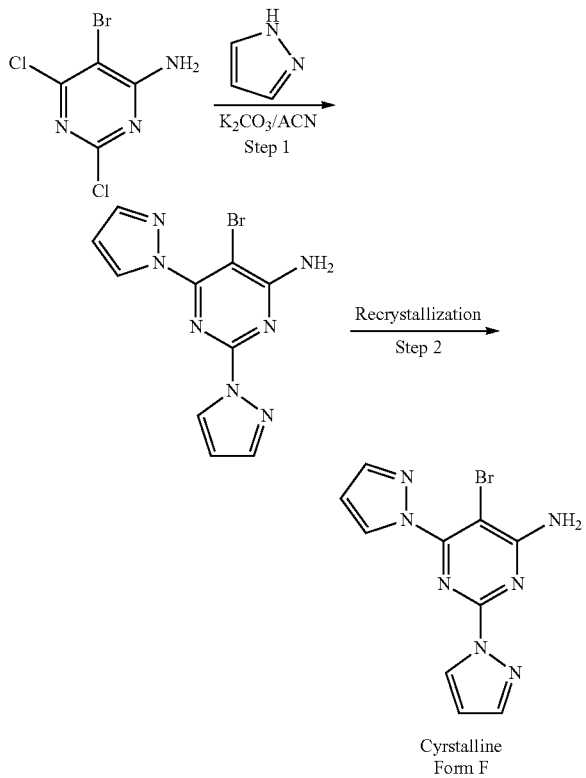

Cyrstalline Form F

Procedure of Step 1

To a reactor, were charged pyrazole (252 g, 9.0 eq.), acetonitrile (5 L) and potassium carbonate (860 g, 3.02 eq.). The mixture was heated at 65-75° C. for 30 minutes. The reaction mixture was cooled to 35-45° C., when 5-bromo-2,6-dichloropyrimidin-4-amine (500 g, 1.0 eq.) was added under $N_2$ protection. The resulting mixture was heated at 72-78° C. for 24 h. The reaction mixture was cooled to 40-50° C. and deemed complete by HPLC analysis. Water (20.2 kg) was added over a period of 2 hours. The temperature was controlled at 20° C. for 2 hours. The crude product was collected by filtration and washed with water (5.0 kg). The crude material was slurred with acetonitrile (0.8 kg) and water (4 kg) at 50-60° C. for 1 hour. Wet cake was obtained by filtration and washing with water (2.0 kg). The wet cake was dissolved in acetonitrile (153.0 kg) and water (2.3 kg) at 47° C., and active carbon (0.075 kg) was added. The mixture was stirred at 42-52° C. for 1.5 hours. Solid was filtered off through microcrystalline cellulose. The filtrate was concentrated under vacuum at 55° C. till the total volume left was around 2.7 L. Water (4.0 kg) was added to the solution. The mixture was concentrated under vacuum at 55° C. till the total volume left was around 6.0 L. To the mixture acetonitrile (0.4 kg) and process water (4.0 kg) were added. And temperature was controlled at 47° C. for 3 hour and at 20° C. for 2 hours sequentially. The product was collected by filtration and washed with process water (1.5 kg). The wet cake was dried under vacuum for 20 hours at 50° C. to give 450 g of 5-bromo-2,6-di(1H-pyrazol-1-yl)pyrimidin-4-amine (71.2% yield) as an off white solid.

Alternative Procedure for Step 1:

To a reactor, was charged 5-bromo-2,6-dichloropyrimidin-4-amine (50 g, 1.0 eq.), pyrazole (126.1 g, 9 eq.) and DMSO (350 mL). To the mixture was charged KOH (26 g, 2.25 eq.) with internal temperature kept under 35° C. The reaction was stirred for additional 30 min with internal temperature maintained under 35° C. by adjusting the jacket temperature. The reaction was then stirred at 35° C. for 2 hr, followed by stirring at 50° C. for 3 hr, and deemed complete by HPLC analysis. To the mixture, was added 0.5% KOH solution (60 mL) dropwise at 50° C. The solution was cooled to 45° C., added by 5-bromo-2,6-di(1H-pyrazol-1-yl)pyrimidin-4-amine seeds (0.02 g) and aged for 30 min. To the suspension, was added 540 mL 0.5% KOH over 2 hr with the internal temperature kept at 45° C. Upon completion of addition, the suspension was cooled to 23° C. over 90 min. The solid was collected by filtration, rinsed with 200 mL $H_2O$, and dried in a full vacuum oven at 60° C. for 16 hr to give 56.6 g 5-bromo-2,6-di(1H-pyrazol-1-yl)pyrimidin-4-amine (89.8% yield) as a white solid.

Step 2: Recrystallization Procedure:

To a reactor was added the crude 5-bromo-2,6-di(1H-pyrazol-1-yl)pyrimidin-4-amine (5 g) from the above step, methanol (140 g, 28×) and water (20 g, 4×). The mixture was heated at 50° C. to obtain a clear solution and filtered. The filtrate was concentrated under vacuum to the total weight of around 110 g (22×). The suspension was heated to reflux until all solid was dissolved. The solution was cooled slowly to 42° C. over a 1 h period. Solid precipitated out. Water (160 g, 32×) was added slowly at 42° C. Stirred for 2 hours and cooled to 20° C. After holding at 20° C. for 2 hours with stirring, the product was collected by filtration and washed with water (6 g). The wet cake was dried under vacuum for 20 hours at 55° C. to give 4.55 g of crystalline 5-bromo-2,6-di(1H-pyrazol-1-yl)pyrimidin-4-amine (91% yield). Polymorph of solid was characterized with XRPD FIG. 11, table 6 (Form F).

(Form A) Mono-Hydrochloride Hydrate Salt of 5-bromo-2,6-di(1H-pyrazol-1-yl)pyrimidin-4-amine To a suspension of 50 mg (0.1633 mmol) of 5-bromo-2,6-di(1H-pyrazol-1-yl)-pyrimidin-4-amine (Form F) in 1 mL acetonitrile was added 27.2 uL HCl aqueous solution (6M, 0.1633 mmol) dropwise. The mixture was stirred at 50 degree C. for 20 hours. The mixture was cooled to room temperature within 2 hours and stirring was kept for another 1 hour. The solid was collected with vacuum filtration and dried at r.t overnight. 5-bromo-2,6-di(1H-pyrazol-1-yl)pyrimidin-4-a mono-hydrochloride hydrate was obtained as a crystalline Form A. The solid was analyzed by XRPD after isolation.

(Form B) Di-Hydrochloride Hydrate Salt of 5-bromo-2,6-di(H-pyrazol-1-yl)pyrimidin-4-amine To a suspension of 50 mg (0.1633 mmol) of 5-bromo-2,6-di(1H-pyrazol-1-yl)-pyrimidin-4-amine (Form F) in 1 mL ethyl acetate was added 54.5 uL HCl aqueous solution (6M, 0.3266 mmol) dropwise. The mixture was stirred at 50 degree C. for 20 hours. The mixture was cooled to room temperature within 2 hours and the stirring was maintained for another 1 hour. The solid was collected with vacuum filtration and dried at r.t overnight. 5-bromo-2,6-di(1H-pyrazol-1-yl)-pyrimidin-4-amine di-hydrochloride hydrate was obtained as a crystalline Form B. The solid was analyzed by XRPD after isolation.

(Form C) Sulfate Salt of 5-bromo-2,6-di(1H-pyrazol-1-yl)pyrimidin-4-amine

To a suspension of 3.06 g (10 mmol) of 5-bromo-2,6-di(1H-pyrazol-1-yl)-pyrimidin-4-amine (Form F) in 60 mL acetone at 50° C. was added 1.83 mL (6 mol/L, 11 mmol) sulfuric acid aqueous solution gradually. The resulting mixture was stirred at 50° C. for 10 hours, then cooled to 25 degree C. within 5 hours and stirred for another 1 hour. The solid was separated via suction filtration and dried under vacuum at 40° C. for 4 hours. 5-bromo-2,6-di(1H-pyrazol-1-yl)-pyrimidin-4-amine sulfate salt (2.5 g, 6.2 mmol) was obtained as yellow crystalline solid (Form C) (62% yield). The solid was analyzed by XRPD after isolation.

(Form D) Mesylate Salt of 5-bromo-2,6-di(1H-pyrazol-1-yl)pyrimidin-4-amine

To a suspension of 50 mg (0.1633 mmol) of 5-bromo-2,6-di(1H-pyrazol-1-yl)-pyrimidin-4-amine (Form F) in 1 mL iso-propyl acetate was added methanesulfonic acid (0.1633 mmol) IPAc solution dropwise. The mixture was stirred at 25 degree C. for 20 hours. The mixture was cooled down to room temperature within 2 hours and the stirring was maintained for another 1 hour. The solid was collected with vacuum filtration and dried at r.t overnight. 5-bromo-2,6-di(1H-pyrazol-1-yl)-pyrimidin-4-amine mesylate salt was obtained as a crystalline white solid (Form D). The solid was analyzed by XRPD after isolation.

(Form E) Mesylate Salt of 5-bromo-2,6-di(1H-pyrazol-1-yl)pyrimidin-4-amine

To a suspension of 50 mg (0.1633 mmol) of 5-bromo-2,6-di(1H-pyrazol-1-yl)-pyrimidin-4-amine (Form F) in 1 mL acetone was added methanesulfonic acid (0.1633 mmol) acetone solution dropwise. The mixture was stirred at 25 degree C. for 20 hours. The mixture was cooled to room temperature within 2 hours and stirring was maintained for another 1 hour. The solid was collected with vacuum filtration and dry at r.t overnight. 5-bromo-2,6-di(1H-pyrazol-1-yl)-pyrimidin-4-amine mesylate salt was obtained as a crystalline white solid (Form E). The solid was analyzed by XRPD after isolation.

(Form G) Free form of 5-bromo-2,6-di(1H-pyrazol-1-yl)pyrimidin-4-amine (modification 2)

A saturated ethanol solution of 5-bromo-2,6-di(1H-pyrazol-1-yl)-pyrimidin-4-amine (Form F) (300 mg) was prepared at 60° C., then fast cooled to 4° C. with 400 r/s stir speed in easy-max for several hours. The resulting solid was collected via vacuum filtration and dry at r.t overnight. Free form of 5-bromo-2,6-di(1H-pyrazol-1-yl)-pyrimidin-4-amine (modification 2) was obtained as a crystalline white solid (Form G) with 42% yield. The solid was analyzed by XRPD after isolation.

Powder X-Ray Diffraction

X-ray powder diffraction (XRPD) data were obtained using a Brucker™ D8 Discover Diffractometer. The method is summarized below:

| XRPD | |
|---|---|
| Instrument | Bruker D8 Discover with XYZ stage |
| Detector | VANTEC-500 including controller 19" |
| Radiation | CuKα (0.15406 nm) |
| X-ray generator power | 40 kV, 1 mA (Micro source) |
| Step size, resolution | 0.02 degrees |
| Measuring slice | 0.3 mm and 0.2 mm |
| Scan range | 4° to 45° (2 theta value) |
| Scan time | 2 mm |
| X-ray optics | I μs MONTEL optic for Cu |
| Source slit | Fixed, 1 mm |
| Detector distance | ~30 cm |

TABLE 1

X-ray powder diffraction data for Form A

| Angle (°2θ) | d value (Å) | Rel. Intensity (%) | Intensity |
|---|---|---|---|
| 10.045 | 8.799 | 100.00 | 2436.91 |
| 15.605 | 5.674 | 18.40 | 448.40 |
| 19.609 | 4.523 | 6.25 | 152.27 |
| 20.796 | 4.268 | 21.18 | 516.18 |
| 22.588 | 3.933 | 15.30 | 372.87 |
| 24.455 | 3.637 | 9.79 | 238.61 |
| 24.501 | 3.630 | 10.64 | 259.17 |
| 25.290 | 3.519 | 18.82 | 458.67 |
| 26.520 | 3.358 | 5.23 | 127.39 |
| 28.529 | 3.126 | 20.89 | 509.13 |
| 29.097 | 3.066 | 30.91 | 753.18 |
| 30.723 | 2.908 | 13.08 | 318.75 |
| 33.459 | 2.676 | 6.12 | 149.18 |

TABLE 2

X-ray powder diffraction data for Form B

| Angle (°2θ) | d value (Å) | Rel. Intensity (%) | Intensity |
|---|---|---|---|
| 7.803 | 11.321 | 12.25 | 91.72 |
| 8.225 | 10.742 | 5.81 | 43.48 |
| 9.569 | 9.235 | 38.43 | 287.72 |
| 14.437 | 6.130 | 11.24 | 84.15 |
| 14.891 | 5.944 | 8.37 | 62.65 |

TABLE 2-continued

X-ray powder diffraction data for Form B

| Angle (°2θ) | d value (Å) | Rel. Intensity (%) | Intensity |
|---|---|---|---|
| 16.126 | 5.492 | 16.34 | 122.33 |
| 19.350 | 4.583 | 13.30 | 99.61 |
| 21.512 | 4.127 | 14.57 | 109.10 |
| 22.110 | 4.017 | 85.16 | 637.67 |
| 22.369 | 3.971 | 30.47 | 228.17 |
| 23.113 | 3.845 | 17.02 | 127.47 |
| 23.134 | 3.842 | 17.22 | 128.93 |
| 24.260 | 3.666 | 12.74 | 95.42 |
| 26.435 | 3.369 | 100.00 | 748.79 |
| 27.384 | 3.254 | 34.63 | 259.30 |
| 27.951 | 3.190 | 29.22 | 218.80 |
| 28.440 | 3.136 | 47.62 | 356.55 |
| 29.749 | 3.001 | 10.75 | 80.48 |
| 30.653 | 2.914 | 37.99 | 284.43 |
| 31.710 | 2.819 | 7.40 | 55.43 |
| 34.761 | 2.579 | 14.83 | 111.03 |
| 35.529 | 2.525 | 9.77 | 73.17 |
| 39.179 | 2.297 | 8.89 | 66.56 |

TABLE 3

X-ray powder diffraction data for Form C

| Angle (°2θ) | d value (Å) | Rel. Intensity (%) | Intensity |
|---|---|---|---|
| 9.406 | 9.395 | 100.00 | 1251.30 |
| 12.291 | 7.196 | 32.11 | 401.76 |
| 12.722 | 6.953 | 19.50 | 244.04 |
| 17.124 | 5.174 | 37.36 | 467.54 |
| 18.811 | 4.714 | 12.49 | 156.34 |
| 19.323 | 4.590 | 14.78 | 184.98 |
| 20.498 | 4.329 | 17.70 | 221.53 |
| 23.237 | 3.825 | 70.62 | 883.63 |
| 24.843 | 3.581 | 55.71 | 697.07 |
| 26.063 | 3.416 | 27.38 | 342.63 |
| 26.465 | 3.365 | 32.55 | 407.35 |
| 26.820 | 3.321 | 92.28 | 1154.66 |
| 29.916 | 2.984 | 22.10 | 276.54 |
| 31.739 | 2.817 | 16.38 | 204.98 |
| 44.701 | 2.026 | 10.29 | 128.79 |

TABLEd

X-ray powder diffraction data for Form D

| Angle (°2θ) | d value (Å) | Rel. Intensity (%) | Intensity |
|---|---|---|---|
| 9.092 | 9.719 | 4.98 | 67.76 |
| 10.132 | 8.723 | 15.25 | 207.61 |
| 17.925 | 4.945 | 11.28 | 153.59 |
| 20.282 | 4.375 | 18.02 | 245.40 |
| 24.005 | 3.704 | 100.00 | 1361.52 |
| 25.025 | 3.555 | 5.77 | 78.53 |
| 26.427 | 3.370 | 10.79 | 146.84 |
| 33.355 | 2.684 | 12.52 | 170.50 |

TABLE 5

X-ray powder diffraction data for Form E

| Angle (°2θ) | d value (Å) | Rel. Intensity (%) | Intensity |
|---|---|---|---|
| 9.055 | 9.758 | 19.44 | 139.69 |
| 16.606 | 5.334 | 34.78 | 249.84 |
| 18.024 | 4.918 | 13.69 | 98.34 |
| 21.045 | 4.218 | 27.71 | 199.08 |
| 22.075 | 4.024 | 41.39 | 297.37 |
| 23.447 | 3.791 | 34.55 | 248.21 |
| 24.089 | 3.691 | 20.97 | 150.64 |

TABLE 5-continued

X-ray powder diffraction data for Form E

| Angle (°2θ) | d value (Å) | Rel. Intensity (%) | Intensity |
|---|---|---|---|
| 25.031 | 3.555 | 15.49 | 111.25 |
| 26.669 | 3.340 | 100.00 | 718.44 |
| 29.899 | 2.986 | 17.59 | 126.34 |

TABLE 6

X-ray powder diffraction data for Form F

| Angle (°2θ) | d value (Å) | Rel. Intensity (%) | Intensity |
|---|---|---|---|
| 8.212 | 10.758 | 100.00 | 2929.96 |
| 8.463 | 10.440 | 4.58 | 134.11 |
| 11.512 | 7.681 | 9.24 | 270.69 |
| 12.079 | 7.322 | 4.00 | 117.10 |
| 12.140 | 7.285 | 2.91 | 85.26 |
| 16.403 | 5.400 | 18.10 | 530.40 |
| 16.928 | 5.233 | 8.92 | 261.31 |
| 18.076 | 4.904 | 8.88 | 260.30 |
| 18.930 | 4.684 | 6.76 | 197.96 |
| 23.008 | 3.862 | 5.46 | 160.05 |
| 24.200 | 3.675 | 7.31 | 214.19 |
| 24.957 | 3.565 | 20.47 | 599.90 |
| 25.662 | 3.469 | 25.22 | 738.79 |
| 25.748 | 3.457 | 30.82 | 902.92 |
| 26.550 | 3.355 | 28.17 | 825.48 |
| 27.851 | 3.201 | 8.17 | 239.45 |
| 30.820 | 2.899 | 10.56 | 309.47 |
| 34.738 | 2.580 | 7.01 | 205.34 |

TABLE 7

X-ray powder diffraction data for Form G

| Angle (°2θ) | d value (Å) | Rel. Intensity (%) | Intensity |
|---|---|---|---|
| 8.334 | 10.601 | 69.72 | 2025.02 |
| 10.405 | 8.495 | 16.42 | 476.97 |
| 14.034 | 6.305 | 24.70 | 717.44 |
| 16.671 | 5.313 | 26.31 | 764.23 |
| 20.365 | 4.357 | 6.10 | 177.13 |
| 20.838 | 4.260 | 5.48 | 159.14 |
| 21.815 | 4.071 | 100.00 | 2904.53 |
| 24.650 | 3.609 | 11.86 | 344.60 |
| 25.164 | 3.536 | 79.43 | 2307.10 |
| 26.774 | 3.327 | 46.46 | 1349.57 |
| 28.759 | 3.102 | 5.30 | 153.82 |
| 30.689 | 2.911 | 16.17 | 469.55 |
| 32.864 | 2.723 | 12.43 | 360.90 |
| 34.693 | 2.584 | 4.52 | 131.33 |
| 36.671 | 2.449 | 8.06 | 234.05 |
| 41.283 | 2.185 | 7.96 | 231.32 |
| 42.552 | 2.123 | 18.79 | 545.88 |

Thermal Analysis (TA):
The crystalline forms were analyzed using TA instrument Discovery (DSC) and thermogravimetric analysis (TGA): Discovery (DSC) and Discovery (TGA) with aluminum pan (T150603); heating rate 10° C./min, temperature range: 30 to 300° C.

DSC:
Accurately weigh 10 mg of test substance into the closed sample pan with pinhole. An empty sample pan is used as reference. The DSC thermogram is recorded as follow: the temperature of the apparatus is adjusted to about 30° C., and heated to 300° C. at a heating rate of 10° C./min, under a nitrogen flow of 20 mL/min. The instrument is calibrated for temperature and enthalpy with Indium, at least 99.9999% pure. The accuracy of the measured sample temperature with this method is within about ±1° C., and the heat of fusion can be measured within a relative error of about ±5%.

TGA:
Accurately weigh 10 mg of test substance into the open sample pan. The TGA thermogram is recorded as follows: the sample is loaded into the furnace, and heated to 300° C. at a heating rate of 10° C./min, under a flow of nitrogen at 20 mL/min.

The instrument is calibrated for temperature with nickel, and calibrated for weight with a 100 mg standard.

Illustrative DSC/TGA traces generated using crystalline Forms A, B, C, D, E, F and G are shown in FIGS. 2, 4, 6, 8, 10, 12 and 14, respectively.

Form A: Melting endotherm: $T_{onset}$=78.16° C., ΔH=300.87 J/g; small initial weigh loss of 14.91% before melt onset; and $T_{onset}$=212.48° C., ΔH=86.83 J/g.

Form B: Melting endotherm: $T_{onset}$=78.92° C., ΔH=399.81 J/g; small initial weigh loss of 24.47% before melt onset; and $T_{onset}$=212.18° C., ΔH=81.02 J/g Form C: Melting endotherm: $T_{onset}$=188.44° C., ΔH=117.42 J/g; small initial weigh loss of 0.38% before melt onset.

Form D: Melting endotherm: $T_{onset}$=177.11° C., ΔH=122.19 J/g; small initial weigh loss of 1.72% before melt onset.

Form E: Melting endotherm: $T_{onset}$=188.44° C., ΔH=117.4 J/g; small initial weigh loss of 0.69% before melt onset.

Form F: Melting endotherm: $T_{onset}$=212.63° C., ΔH=104.22 J/g; small initial weigh loss of 0.59% before melt onset.

Form G: Melting endotherm: $T_{onset}$=202.95° C., ΔH=14.84 J/g; small initial weigh loss of 1.06% before melt onset; and $T_{onset}$=212.96° C., ΔH=91.99 J/g.

The invention claimed is:

1. A crystalline form of the sulfate salt of 5-bromo-2,6-di(1H-pyrazol-1-yl)pyrimidin-4-amine characterized by an X-ray powder diffraction (XRPD) pattern comprising peaks, in terms of °2θ, at 9.4±0.2°2θ, 23.2±0.2°2θ, 24.8±0.2°2θ and 26.8±0.2°2θ when measured using CuKα radiation with a wavelength of 1.5418 Å and at a temperature of about 22° C.

2. The crystalline form according to claim 1, wherein the X-ray powder diffraction pattern comprises one or more peaks chosen from 12.3±0.2°2θ, 17.1±0.2°2θ, 26.5 0.2°2θ and 26.1±0.2°2θ, when measured using CuKα radiation with a wavelength of 1.5418 Å and at a temperature of about 22° C.

3. The crystalline form according to claim 1 wherein said crystalline form is Form C.

4. The crystalline form according to claim 3 wherein said Form C is substantially phase pure.

5. The pharmaceutical composition comprising a crystalline form according to claim 1, and a pharmaceutically acceptable excipient.

6. The pharmaceutical combination comprising a therapeutically effective amount of a crystalline form according to claim 1, and one or more immunotherapeutic agents.

7. A method of treating cancer, in a subject in need thereof, comprising: administering to a subject in need thereof, a therapeutically effective amount of a crystalline form according to claim 1, alone or in combination with one or more immunotherapeutic agents.

8. A method according to claim 7, wherein the cancer is selected from wherein the cancer is selected from a lung cancer, a melanoma, a renal cancer, a liver cancer, a myeloma, a prostate cancer, a breast cancer, a colorectal cancer, a pancreatic cancer, a head and neck cancer, anal cancer, gastro-esophageal cancer, thyroid cancer, cervical cancer, a lymphoproliferative disease or a hematological cancer, T-cell lymphoma, B-cell lymphoma, a non-Hogdkin lymphoma, or a leukemia.

9. The method of claim 8, wherein the cancer is lung cancer.

10. The method of claim 9, wherein the lung cancer is non-small cell lung cancer.

11. The method of claim 7, wherein one or more immunotherapeutic agents are selected from the group consisting of anti-CTLA4 antibodies, anti-PD-1 antibodies and anti-PD-L1 antibodies.

12. The method of claim 11, wherein the immunotherapeutic agent is selected from the group consisting of: Ipilimumab, Tremelimumab, Nivolumab, Pembrolizumab, Pidilizumab AMP-224, AMP-514 MPDL3280A, MEDI4736, MSB0010718C, YW24355S70 and MDX-1105.

13. The method of claim 11, wherein the immunotherapeutic agents is an anti-PD-1 antibody.

14. The method according to claim 13, wherein the anti-PD-1 antibody comprises:
   (a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;
   (b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;
   (c) a VH comprising a VHCDR1 amino acid sequence of SEQ ID NO: 41, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or
   (d) a VH comprising a VHCDR1 amino acid sequence of SEQ ID NO: 41; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

15. The method according to claim 13, wherein the anti-PD-1 comprises a VH comprising the amino acid sequence of SEQ ID NO: 6 and a VL comprising the amino acid sequence of SEQ ID NO: 20.

16. The method according to claim 13, wherein the anti-PD-1 antibody comprises a heavy chain comprising the amino acid sequence of SEQ ID NO: 8 and a light chain comprising the amino acid sequence of SEQ ID NO: 22.

17. The method according to claim 13, wherein the anti-PD-1 antibody comprises a VH comprising the amino acid sequence of SEQ ID NO: 6 and a VL comprising the amino acid sequence of SEQ ID NO: 16.

18. The method according to claim 13, wherein the anti-PD-1 antibody comprises a heavy chain comprising the amino acid sequence of SEQ ID NO: 8 and a light chain comprising the amino acid sequence of SEQ ID NO: 18.

19. The method according to claim 13, wherein the anti-PD-1 antibody molecule is administered at a dose of about 300 mg once every three weeks.

20. The method, according to claim 13, wherein the anti-PD-1 antibody molecule is administered at a dose of about 400 mg once every four weeks.

21. The method of claim 11, wherein the immunotherapeutic agents is an anti-PD-L1 antibody.

22. The method according to claim 21, wherein the anti PD-L1 antibody molecule comprises:
   (a) a heavy chain variable region (VH) comprising a VHCDR1 amino acid sequence of SEQ ID NO: 47, a VHCDR2 amino acid sequence of SEQ ID NO: 48, and a VHCDR3 amino acid sequence of SEQ ID NO: 46; and a light chain variable region (VL) comprising a VLCDR1 amino acid sequence of SEQ ID NO: 52, a VLCDR2 amino acid sequence of SEQ ID NO: 53, and a VLCDR3 amino acid sequence of SEQ ID NO: 54;
   (b) a VH comprising a VHCDR1 amino acid sequence of SEQ ID NO: 44; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51;
   (c) a VH comprising a VHCDR1 amino acid sequence of SEQ ID NO: 63, a VHCDR2 amino acid sequence of SEQ ID NO: 48, and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54; or
   (d) a VH comprising a VHCDR1 amino acid sequence of SEQ ID NO: 63; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51.

23. The method according to claim 7, wherein immunotherapeutic agent is administered together in a single composition or administered separately in two or more different compositions forms.

24. The method according to claim 7, wherein the immunotherapeutic agent is administered concurrently with, prior to, or subsequent to, the crystalline form sulfate salt of claim 1.

25. The method according to claim 22, wherein the anti PD-L1 antibody molecule comprises a heavy chain variable domain comprising the amino acid sequence of SEQ ID NO: 55 and a light chain variable domain comprising the amino acid sequence of SEQ ID NO: 58.

* * * * *